US007622461B2

(12) United States Patent
Ek et al.

(10) Patent No.: US 7,622,461 B2
(45) Date of Patent: *Nov. 24, 2009

(54) AMINO SUBSTITUTED DIARYL[A,D]CYCLOHEPTENE ANALOGS AS MUSCARINIC AGONISTS AND METHODS OF TREATMENT OF NEUROPSYCHIATRIC DISORDERS

(75) Inventors: Fredrik Ek, Lund (SE); Roger Olsson, Bunkeflostrand (SE); Jörgen Ohlsson, Sandby (SE)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/733,476

(22) Filed: Apr. 10, 2007

(65) Prior Publication Data

US 2007/0197502 A1 Aug. 23, 2007

Related U.S. Application Data

(63) Continuation of application No. 11/019,555, filed on Dec. 21, 2004.

(60) Provisional application No. 60/531,927, filed on Dec. 22, 2003, provisional application No. 60/548,090, filed on Feb. 24, 2004, provisional application No. 60/548,604, filed on Feb. 27, 2004.

(51) Int. Cl.
*A61P 25/00* (2006.01)
*A61K 31/553* (2006.01)
*C07D 267/02* (2006.01)

(52) U.S. Cl. .................. 514/211.13; 500/551
(58) Field of Classification Search ............ 514/211.13; 540/551
See application file for complete search history.

(56) References Cited

U.S. PATENT DOCUMENTS

| 3,389,139 | A | 6/1968 | Schmutz et al. |
| 3,412,193 | A | 11/1968 | Coppola |
| 3,444,169 | A | 5/1969 | Howell et al. |
| 3,501,483 | A | 3/1970 | Howell et al. |
| 3,532,702 | A | 10/1970 | Howell et al. |
| 3,539,573 | A | 11/1970 | Schmutz et al. |
| 3,546,226 | A | 12/1970 | Hunziker et al. |
| 3,660,406 | A | 5/1972 | Howell et al. |
| 3,663,696 | A | 5/1972 | Howell et al. |
| 3,751,415 | A | 8/1973 | Schmutz et al. |
| 3,758,479 | A | 9/1973 | Schmutz et al. |
| 3,761,481 | A | 9/1973 | Nakanishi et al. |
| 3,811,026 | A | 5/1974 | Kaplan et al. |
| 3,884,920 | A | 5/1974 | Schmutz et al. |
| 3,852,446 | A | 12/1974 | Schmutz et al. |
| 3,908,010 | A | 9/1975 | Schmutz et al. |
| 3,962,248 | A | 6/1976 | Schneider |
| 3,983,234 | A | 9/1976 | Sayers |
| 4,045,445 | A | 8/1977 | Hardy, Jr. et al. |
| 4,096,261 | A | 6/1978 | Horrom et al. |
| 4,097,597 | A | 6/1978 | Horrom et al. |
| 4,191,760 | A | 3/1980 | Horrom et al. |
| 4,243,805 | A | 1/1981 | Protiva et al. |
| 4,263,207 | A | 4/1981 | Rokach et al. |
| 4,308,207 | A | 12/1981 | Hunziker et al. |
| 4,404,137 | A | 9/1983 | Chakrabarti et al. |
| 4,406,900 | A | 9/1983 | Hunziker et al. |
| 4,663,453 | A | 5/1987 | Glamkowski et al. |
| 4,764,616 | A | 8/1988 | Glamkowski et al. |
| 5,300,422 | A | 4/1994 | Gerson et al. |
| 5,344,828 | A | 9/1994 | Sawanishi et al. |
| 5,354,747 | A | 10/1994 | Hansen, Jr. et al. |
| 5,393,752 | A | 2/1995 | Liegeois et al. |
| 5,538,965 | A | 7/1996 | Tehim et al. |
| 5,602,120 | A | 2/1997 | Fu et al. |
| 5,602,121 | A | 2/1997 | Fu |
| 5,602,124 | A | 2/1997 | Tehim et al. |
| 5,700,445 | A | 12/1997 | Fu et al. |
| 5,707,798 | A | 1/1998 | Brann |
| 5,814,628 | A | 9/1998 | Fu et al. |
| 5,817,655 | A | 10/1998 | Chakrabarti et al. |
| 5,834,459 | A | 11/1998 | Fu |
| 5,962,664 | A | 10/1999 | Friedhoff et al. |
| 5,968,478 | A | 10/1999 | Fu et al. |
| 6,479,488 | B1 | 11/2002 | Di-Fabio et al. |
| 6,566,065 | B1 | 5/2003 | Rozen |
| 6,630,462 | B2 | 10/2003 | DeHaven et al. |
| 7,491,715 | B2 | 2/2009 | Ek et al. |
| 7,517,871 | B2 | 4/2009 | Ek et al. |
| 2002/0037886 | A1 | 3/2002 | Andersson et al. |
| 2004/0224942 | A1 | 11/2004 | Weiner et al. |
| 2005/0085463 | A1 | 4/2005 | Weiner et al. |
| 2005/0192268 | A1 | 9/2005 | Ek et al. |
| 2005/0250767 | A1 | 11/2005 | Weiner et al. |
| 2005/0282800 | A1 | 12/2005 | Tolf et al. |
| 2006/0063754 | A1 | 3/2006 | Edgar et al. |
| 2006/0063755 | A1 | 3/2006 | Edgar et al. |

(Continued)

FOREIGN PATENT DOCUMENTS

CH 240 228 A 12/1945

(Continued)

OTHER PUBLICATIONS

Alves-Rodrigues A, Leurs R, Willems E and Timmerman H (1996). Binding of clozapine metabolites and analogues to the histamine H3 receptor in rat brain cortex. *Archiv der Pharmazie*, 329: 413-416.

(Continued)

*Primary Examiner*—Brenda L Coleman
(74) *Attorney, Agent, or Firm*—Knobbe, Martens, Olson & Bear LLP

(57) ABSTRACT

Disclosed herein are analogs of clozapine and pharmaceutically acceptable salts, esters, amides, or prodrugs thereof, methods of synthesizing the analogs; and methods of using the analogs for treating neuropsychiatric disorders. In some embodiments, the analogs are amino substituted diaryl[a,d] cycloheptenes.

26 Claims, No Drawings

U.S. PATENT DOCUMENTS

| | | |
|---|---|---|
| 2006/0069083 A1 | 3/2006 | Steiner et al. |
| 2006/0111342 A1 | 5/2006 | Argentine et al. |
| 2006/0194784 A1 | 8/2006 | Ek et al. |
| 2006/0194831 A1 | 8/2006 | Weiner et al. |
| 2006/0199798 A1 | 9/2006 | Ek et al. |
| 2006/0199807 A1 | 9/2006 | Weiner et al. |
| 2006/0199808 A1 | 9/2006 | Tolf et al. |
| 2006/0205714 A1 | 9/2006 | Tolf et al. |
| 2006/0233843 A1 | 10/2006 | Conn et al. |
| 2006/0252744 A1 | 11/2006 | Burstein |
| 2007/0105836 A1 | 5/2007 | Pettersson et al. |
| 2007/0197502 A1 | 8/2007 | Ek et al. |
| 2007/0275957 A1 | 11/2007 | Weiner et al. |

FOREIGN PATENT DOCUMENTS

| | | |
|---|---|---|
| CH | 422 793 A | 10/1966 |
| CH | 436 297 | 5/1967 |
| CH | 476 753 A | 8/1969 |
| CH | 493 538 A | 7/1970 |
| CH | 499 539 A | 11/1970 |
| CH | 517 759 | 1/1972 |
| CH | 585 222 A5 | 2/1977 |
| CH | 601 288 A5 | 7/1978 |
| CS | 0179793 B | 11/1977 |
| DE | 2316438 | 10/1973 |
| DE | 24 13 610 | 10/1974 |
| DE | 26 25 258 A1 | 12/1976 |
| DE | 133 235 A1 | 12/1978 |
| EP | 0 240 228 A | 10/1987 |
| EP | 1 726 952 A1 | 11/2006 |
| FR | 870 763 A | 3/1942 |
| FR | 939 595 A | 11/1948 |
| FR | 1 334 944 A | 8/1963 |
| FR | 939 591 | 4/1964 |
| FR | 2 222 102 A | 10/1974 |
| GB | 1 006 156 | 9/1965 |
| GB | 1 164 360 | 9/1969 |
| GB | 1 177 956 A | 1/1970 |
| GB | 1 177 957 A | 1/1970 |
| GB | 1 216 523 A | 12/1970 |
| GB | 1 218 045 | 1/1971 |
| GB | 1 355 866 | 6/1974 |
| GB | 1 418 363 | 12/1975 |
| GB | 1 554 275 A | 10/1979 |
| GB | 2 292 685 | 3/1996 |
| WO | WO 93/07143 A1 | 4/1993 |
| WO | WO 95/17400 A1 | 6/1995 |
| WO | WO 96/18621 | 6/1996 |
| WO | WO 96/18623 | 6/1996 |
| WO | WO 96/18629 | 6/1996 |
| WO | WO 96/29316 A1 | 9/1996 |
| WO | WO 99/50247 A1 | 10/1999 |
| WO | WO 01/29036 A2 | 4/2001 |
| WO | WO 01/83472 A1 | 11/2001 |
| WO | WO 02/060870 A2 | 8/2002 |
| WO | WO 03/000670 A1 | 1/2003 |
| WO | WO 03/070249 A1 | 8/2003 |
| WO | WO 03/082877 A1 | 10/2003 |
| WO | WO 2004/026030 A2 | 4/2004 |
| WO | WO 2004/056182 A1 | 7/2004 |
| WO | WO 2004/064738 A3 | 8/2004 |
| WO | WO 2004/064753 A2 | 8/2004 |
| WO | WO 2004/073639 A2 | 9/2004 |
| WO | WO 2004/078216 A2 | 9/2004 |
| WO | WO 2005/002586 A1 | 1/2005 |
| WO | WO 2005/063254 A2 | 7/2005 |
| WO | WO 2005/103041 A2 | 11/2005 |
| WO | WO 2006/017614 | 2/2006 |
| WO | WO 2006/034414 A2 | 3/2006 |
| WO | WO 2006/049734 | 5/2006 |
| WO | WO 2006/081327 A2 | 8/2006 |
| WO | WO 2006/088786 A2 | 8/2006 |
| WO | WO 2006/107948 | 10/2006 |
| WO | WO 2007/062336 | 5/2007 |
| WO | WO 2007/062337 | 5/2007 |
| WO | WO 2007/062338 | 5/2007 |
| WO | WO 2007/062339 | 5/2007 |
| WO | WO 2008/002602 | 1/2008 |
| WO | WO 2008/066620 | 5/2008 |

OTHER PUBLICATIONS

Anonymous, Certificate of Analysis: N-Desmethylclozapine (2003), Internet article, Database accession No. 2003: 2066817, Order No. D292000.

Anonymous, Morphanthridine. Research Disclosure, 258:512-14 (1985).

Anonymous, Piperazinyldibenzazepine. Research Disclosure, 192:158-9 (1980).

Ashby, C.R. et al., Pharmacological actions of the atypical antipsychotic drug clozapine: A review, Synapse, 24:349-394 (1996).

Baldessarini RJ, Centorrino F, Flood JG, Volpicelli SA, Huston-Lyons D and Cohen BM (1993). Tissue concentrations of clozapine and its metabolite in the rat. *Neuropsychopharm*, 9:117-124.

Baldessarini, R., J., and Frankenburg, F., R. (1991) Clozapine. A novel antipsychotic agent. *New. Engl. J. Med.*, 324(11): 746-754.

Baumeister AA, Francis JL. Historical development of the dopamine hypothesis of schizophrenia. *J Hist Neurosci*. Sep. 2002;11(3):265-77.

Berkeley JL and Levey AI (2003). Cell-Specific Extracellular Signal-regulated Kinase Activation by Multiple G Protein-coupled receptor Families in Hippocampus. *Mol Pharm*, 63: 128-135.

Berkeley JL, Gomeza J, Wess J, Hamilton SE, Nathanson NM and Levey AI (2001). M1 Muscarinic Acetylcholine Receptors Activate Extracellular Signal-Regulated Kinase in CA1 Pyramidal Neurons in Mouse Hippocampal Slices. *Mol Cell Neurosci*, 18: 512-524.

Birdsall, N.J.M. et al., Subtype-selective positive cooperative interactions between brucine analogs and acetylcholine at muscarinic receptors: Functional studies, Molecular Pharmacology, 55(4):778-786 (1999).

Bodick NC, Offen WW, Levey AI, Cutler NR, Gauthier SG, Satlin A, Shannon HE, Tollefson GD, Rasmussen K, Bymaster FP, Hurley DJ, Potter WZ, Paul SM (1997) Effects of xanomeline, a selective muscarinic receptor agonist, on cognitive function and behavioral symptoms in Alzheimer disease. *Arch Neurol* 54:465-473.

Bolden C, Cusack B, Richelson E (1991) Clozapine is a potent and selective muscarinic antagonist at the five cloned human muscarinic acetylcholine receptors expressed in CHO-K1 cells. *Eur J Pharmacol* 192:205-206.

Bondesson U, Lindstrom LH (1988) Determination of clozapine and its N-demethylated metabolite in plasma by use of gas chromatography-mass spectrometry with single ion detection. *Psychopharmacology* 95:472-475.

Bonner TI, Buckley NJ, Young AC, Brann MR (1987) Identification of a family of muscarinic acetylcholine receptor genes. *Science* 237:527-532.

Bonner, T.I. et al., Cloning and expression of the human and rat m5 muscarinic acetylcholine receptor genes, Neuron, 1:403-410 (1988).

Bourin Michel et al., Cyamemazine as an anxiolytic drug on the elevated plus maze and light/dark paradigm in mice (2001), Behavioural Brain Research, 124(1):87-95.

Brauner-Osborne H, Ebert B, Brann MR, Falch E, Krogsgaard-Larsen P (1996) Functional partial agonism at cloned human muscarinic acetylcholine receptors. *Eur J Pharmacol* 313:145-150.

Brown, J., H., and Taylor, P., (1996) Muscarinic receptor agonists and antagonists, in The pharmacological basis of therapeutics. Hardiman, J., G., and Limbird, L., E., editors, Mcgraw-Hill, New York, pp. 141-161.

Buerki, H.R. et al., Effects of clozapine and other dibenzo-epines on central dopaminergic and cholinergic systems. Structure-activity relationships. Arzneimittel-Forschung, 27(8)1561-5 (1977).

Bun H, Disdier B, Aubert C and Catalin J (1999). Interspecies variability and drug interactions of clozapine metabolism by microsomes. *Fundam Clin Pharmacol.* 13: 577-581.

Burris KD, Molski TF, Xu C, Ryan E, Tottori K, Kikuchi T, Yocca FD, Molinoff PB. Aripiprazole, a novel antipsychotic, is a high-affinity partial agonist at human dopamine D2 receptors. *J Pharrnacol Exp Ther.* Jul. 2002;302(1):381-9.

Burstein et al., J. Pharmacol. Exp. Ther. 315(3)1278-1287 (2005).

Bymaster FB, Carter PA, Yamada M, Gomeza J, Wess J, Hamilton S, Nathanson NM, McKinzie DL, Felder CC (2003) Role of specific muscarinic receptor subtypes in cholinergic parasympathomimetic responses, in vivo phosphoinositide hydrolysis, and pilocarpine-induced seizure activity. *Eur J Neurosci* 17:1403-1410.

Bymaster FP, Felder C, Ahmned S and McKinzie D (2002). Muscarinic Receptors as a Target for Drugs Treating Schizophrenia. *Curr Drug Targ CNS Neural Dis*, 1: 163-181.

Bymaster, F.P., Potential role of muscarinic receptors in schizophrenia, Life Sciences, 64(6/7):527-534 (1999).

Capuano, Molecules 4:329-332 (1999).

Carlsson A (1978) Antipsychotic drugs, neurotransmitters, and schizophrenia. *Am J Psychiatry* 135(2):164-173.

Casey DE. Tardive dyskinesia: pathophysiology and animal models. *J Clin Psychiatry* 2000;61 Suppl 4:5-9.

Centorrino, F., Baldessarini, R., J., Kando, J., C., et. al. (1994) Clozapine and metabolites: concentrations in serum and clinical findings during treatment of chronically psychotic patients. *J. Clin. Psychopharmacol.* 14: 119-125.

Charfi F, Cohen D, Houeto JL, Soubrie C, Mazet P. Tardive dystonia induced by atypical neuroleptics: a case report with olanzapine. *J Child Adolesc Psychopharrnacol.* 2004 Spring;14(1)149-52.

Christopoulos, A., Allosteric binding sites on cell-surface receptors: Novel targets for drug discovery, Nature Reviews. Drug Discovery, 1:198-210 (2002).

Creese I, Burt DR and Snyder SH (1976) Dopamine receptor binding predicts clinical and pharmacological potencies of antischizophrenic drugs. *Science* 192: 481-483.

Daeffler L, Landry Y. Inverse agonism at heptahelical receptors: concept, experimental approach and therapeutic potential. *Fundam Clin Pharmacol.* Mar.-Apr. 2000;14(2):73-87.

Davis RE, Emmerling MR, Jaen JC, Moos WH, Spiegel K (1993) Therapeutic intervention in dementia. *Crit Rev Neurobiol* 7:41-83.

Davis, RE; Doyle, P D; Carroll, R T; Emmerling, M R; Jaen, J. Cholinergic therapies for Alzheimer's disease: Palliative or disease altering? Arzneimittel-Forschung, 45, 425-431, 1995.

Durif F. et al., Low-dose clozapine improves dyskinesias in Parkinson's disease, Neurology vol. 48, No. 3, 1997, pp. 658-662.

Eglen, R., M., Choppin, A., and Watson, N., (2001) Therapeutic opportunities from muscarinic receptor research. Trends Pharmacol. Sci. 22(8): 409-414.

Fabrazzo M, La Pia S, Monteleone P, Esposito G, Pinto A, De Simone L, Bencivenga R, Maj M (2002) Is time course of clozapine response correlated to the time course of plasma clozapine levels? A one- year prospective study in drug-resistant patients with schizophrenia. *Neuropsychopharmacology* 27:1050-1055.

Felder CC, Bymaster FP, Ward J and DeLapp N (2000). Therapeutic Opportunities for Muscarinic Receptors in the Central Nervous System, *J Med Chem*, 43: 4333-4353.

Felder, C.C. et al., Elucidating the role of muscarinic receptors in psychosis, Life Sciences, 68:2605-2613 (2001).

Frazier JA, Glassner Cohen L, Jacobsen L, Grothe D, Flood J, Baldessarini RJ, Piscitelli S, Kim GS, Rapoport JL (2003) Clozapine pharmacokinetics in children and adolescents with childhood-onset schizophrenia. *J Clin Psychopharmacol* 23(1):87-91.

Fritze J, Elliger T (1995) Pirenzepine for clozapine-induced hypersalivation. *Lancet* 346:1034.

Gauch R, Michaelis W (1971) The metabolism of 8-chloro-11-(4-methyl-1-piperazinyl)-5H-dibenzo [b,e] [1,4] diazepine (clozapine) in mice, dogs, and human subjects. Il Farmaco 26:667-681.

Gerber DJ, Sotnikova TD, Gainetdinov RR, Huang SY, Caron MG, Tonegawa S (2001) Hyperactivity, elevated dopaminergic transmission, and response to amphetamine in M1 muscarinic acetylcholine receptor-deficient mice. *Proc Natl Acad Sci USA* 98(26):15312-15371.

Gerlach J. et al, Intolerance to Neuroleptic Drugs: The art of avoiding extrapyramidal syndromes, European Psychiatry, vol. 10, No. Supp 1, (1994) pp. 27S-31S.

Gourzis Philippos et al., Quetiapine in the treatment of focal tardive dystonia induced by other atypical antipsychotics—A report of 2 cases, Clinical Neuropharmacology, vol. 28, No. 4, Jul. 2005, pp. 195-196.

Green MF (1996) What are the functional consequences of neurocognitive deficits in schizophrenia? *Am J Psychiatry* 153:321-330.

Hagger C, Buckley P, Kenny JT, Friedman L, Ubogy D, Meltzer HY (1993) Improvement in cognitive functions and psychiatric symptoms in treatment-refractory schizophrenic patients receiving clozapine. *Biol Pyschiatry* 34:702-712.

Hall DA, Strange PG Evidence that antipsychotic drugs are inverse agonists at D2 dopamine receptors. *Br J Pharmacol.* Jun. 1997;121(4):731-6.

Hamilton SE and Nathanson NM (2001). The M1 Receptor is required for Muscarinic Activation of Mitogen-activated Protein (MAP) Kinase in Murine Cerebral Cortical Neurons. *J Biol Chem*, 276: 15850-15853.

Harrison TS & Perry CM Aripirazole: A review of its use in schizophrenia and schizoaffective disorder. *Drugs* 2004 64(15):1715-1736.

Hasegawa M, Gutierrez-Esteinou R, Way L, Meltzer HY (1993) Relationship between clinical efficacy and clozapine concentrations in plasma in schizophrenia: effect of smoking. *J Clin Psychopharmacol* 13:383-390.

Heinrichs DW, Hanlon TE, Carpenter WT (1984) The Quality of Life Scale: an instrument for rating the schizophrenia deficit syndrome. *Schizophr Bull* 10:388-398.

Hunziker F. Fisher, E., and Scmutz, J. (1967) 11-amino-5H-dibenzo[b,e]-1,4-diazepine. Mitteilung uber siebenglienrige Heterocyclen. *Helv. Chim. Acta*, 50:1588-1599.

Inoue T, Domae M, Yamada K, Furukawa T. Effects of the novel antipsychotic agent 7-(4-[4-(2,3-dichlorophenyl)-1-piperazinyl]butyloxy)-3,4-dihydro -2(1H)-quinolinone (OPC-14597) on prolactin release from the rat anterior pituitary gland. *J Pharmacol Exp Ther.* Apr. 1996;277(1):137-43.

Jacobson, M.A. et al., Mapping the interaction site of M1 muscarinic receptor allosteric agonists, abstract, Society for Neuroscience Annual Meeting, San Diego, CA, Oct 23-27, 2004.

Jakubik, J. et al., Allosteric modulation by persistent binding of xanomeline of the interaction of competitive ligands with the M1 muscarinic acetylcholine receptor, Journal of Pharmacology and Experimental Therapeuties, 301(3):1033-1041 (2002).

Jann, M., W., Grimsley, S., R., Gray, E., C., and Chang, W. (1993) Pharmacokinetic and pharmacodynamics of clozapine. *Clin. Pharmacokinet.* 24(2): 161-176.

Jensen, A., A., Spalding, T., A., Burstein E., S., et. al. (2000) Functional importance of the Ala(116)-Pro(136) region in the calcium-sensing receptor. Constitutive activity and inverse agonism in a family C G-protein-coupled receptor. *J Biol Chem.* 275(38): 29547-55.

Kane J, Honigfeld G, Singer J, Meltzer H, Clozaril Collaborative Study Group (1988) Clozapine for the treatment-resistant schizophrenic. *Arch Gen Psychiatry* 45:789-796.

Kuoppamaki M, Syvalahti E, Hietala J (1993) Clozapine and N-desmethylclozapine are potent 5-HT1C receptor antagonists. *Eur J Pharmacol* 245:179-182.

Lammers et al., Coadministration of clozapine and fluvoxamine in psychotic patients —clinical experience (1999), Pharmacopsychiatry, 32(2):76-77.

Lawler CP, Prioleau C, Lewis MM, Mak C, Jiang D, Schetz JA, Gonzalez AM, Sibley DR, Mailman RB. Interactions of the novel antipsychotic aripiprazole (OPC-14597) with dopamine and serotonin receptor subtypes. *Neuropsychopharmacology.* Jun. 1999;20(6):612-27.

Lazareno, S. et al., Towards a high-affinity allosteric enhancer at muscarinic M1 receptors, J. of Molecular Neuroscience, 19:123-127 (2002).

Lee MA, Jayathilake K, Meltzer HY (1999) A comparison of the effect of clozapine with typical neuroleptics on cognitive function in neuroleptic-responsive schizophrenia. *Schizophr Res* 37:1-11.

Leucht S, Wahlbeck K, Hamann J, Kissling W (2003) New generation antipsychotics versus low-potency conventional antipsychotics: a systematic review and meta-analysis. *Lancet* 361(9369):1581-1589.

Liao et al. J. Med. Chem. 1997, 40, 4146-4153.

Liao et al. J. Med. Chem. 1999, 42, 2235-2244.

Lin, G., Characterization of metabolites of clozapine N-oxide in the rat by micro-column high performance liquid chromatography/mass spectrometry with electrospray interface (1996), J. Pharmaceutical and Biomedical Analysis, 14:1561-1577.

Lu, ML, Dosing Strategies of Clozapine-fluvoxamine cotreatment (2002), Journal of Clinical Psychopharmacology, Williams and Wilkins, 22(6):626-628.

Ma JN, Currier EA, Essex A, Feddock M, Spalding TA, Nash NR, Brann MR, Burstein ES. Discovery of novel peptide/receptor interactions: identification of PHM-27 as a potent agonist of the human calcitonin receptor. *Biochem Pharmacol.* Apr. 1, 2004;67(7):1279-84.

Mauri MC, Volonteri LS, Dell'Osso B, Regispani F, Papa P, Baldi M, Bareggi SR (2003) Predictors of clinical outcome in schizophrenic patients responding to clozapine. *J Clin Psychophannacol* 23(6):660-664.

Meltzer HY, Alphs L, Green AI, Altamura AC, Anand R, Bertoldi A, Bourgeois M, Chouinard G, Zahur Islam M, Kane J, Krishnan R, Lindenmayer JP, Potkin S (2003) Clozapine treatment for suicidality in schizophrenia. *Arch Gen Psychiatry* 60:82-91.

Meltzer HY, Matsubara S, Lee JC (1989) Classification of typical and atypical antipsychotic drugs on the basis of dopamine D-1, D-2 and serotonin2 pKi values. *J Pharmacol Exp Ther* 251:238-246.

Meltzer HY. What's atypical about atypical antipsychotic drugs? *Curr Opin Pharmacol.* 2004 4(1):53-7.

Merck Manual, The, seventeenth Edition (1999), Merck Research Laboratories, pp. 1563-1573.

Miller RJ, Hiley CR (1974) Anti-muscarinic properties of neuroleptics and drug-induced Parkinsonism. *Nature* 248:596-597.

Milligan G, MacEwan DJ, Mercouris M, Mullaney I. Inverse agonism at adrenergic and opioid receptors: studies with wild type and constitutively active mutant receptors. *Receptors Channels.* 1997;5(3-4):209-13.

Mirza NR, Peters D, Sparks RG (2003) Xanomeline and the antipsychotic potential of muscarinic receptor subtype selective agonists. *CNS Drug Rev* 9 (2):159-186.

Mosier KE, Song J, McKay G, Hubbard JW and Fang J (2003). Determination of clozapine, and its metabolites, N-desmethylclozapine and clozapine N-oxide in dog plasma using high-performance liquid chromatography. *J Chromat B*, 783: 377-382.

Nordin C, Alme B, Bondesson U (1995) CSF and serum concentrations of clozapine and its demethyl metabolite: a pilot study. *Psychopharmacology* 122 :104-107.

Olianas MC, Maullu C, Onali P (1999) Mixed agonist-antagonist properties of clozapine at different human cloned muscarinic receptor subtypes expressed in chinese hamster ovary cells. *Neuropsychopharmacology* 20(3):263-270.

Olianas, M.C. et al., Effects of clozapine on rat striatal muscarinic receptors coupled to inhibition of adenylyl cyclase activity and on the human cloned m4 receptor, Brit. J. Pharmacol., 122:401-408 (1997).

Özdemir, V., et al., "CYP1A2 Activity as Measured by a Caffeine Test Predicts Clozapine and Active Metabolite Norclozapine Steady-State Concentration in Patients With Schizophrenia," Journal of Clinical Psychopharmacology, 21:4(398-407), Aug. 2001.

Parkinson Study Group, The (1999) Low-dose clozapine for the treatment of drug-induced psychosis in Parkinson's Disease. *N. Engl J Med* 340:757-763.

Perry PJ, Miller DD, Arndt SV, Cadoret RJ (1991) Clozapine and norclozapine plasma concentrations and clinical response of treatment-refractory schizophrenic patients. *Am J Psychiatry* 148(2):231-135.

Pfeiffer CC, Jenney EH (1957) The inhibition of the conditioned response and the counteraction of schizophrenia by muscarinic stimulation of the brain. *Ann NY Acad Sci* 66:753-764.

Schaber, G. et al., Isolation and identification of clozapine metabolites in patient urine, Drug Metabolism and Disposition, 29(6):923-931 (2001).

Schlicker E and Marr I (1996). The moderate affinity of clozapine at H3 receptors is not shared by its two major metabolites and by structurally related and unrelated atypical neuroleptics. *Naunyn-Sch Arch Pharmacol*, 353: 290-294.

Schmutz, J, Neuroleptic Piperazinyl-dibenzo-azepines, Arzneimittel Forschung. Drug Research, 25(5):712-720 (1975).

Seeman P, Lee T, Chau-Wong M and Wong K (1976) Antipsychotic drug doses and neuroleptic/dopamine receptors. *Nature* 261: 717-719.

Serretti A, De Ronchi D, Lorenzi C, Berardi D. New antipsychotics and schizophrenia: a review on efficacy and side effects. *Curr Med Chem.* Feb. 2004;11(3):343-58.

Shannon HE, Bymaster FP, Calligaro DO, Greenwood B, Mitch CH, Sawyer BD, Ward JS, Wong DT, Olesen PH, Sheardown MJ, Swedberg MDB, Suzdak PD, Sauerberg P (1994) Xanomeline: a novel muscarinic receptor agonist with functional selectivity for M1 receptors. *J Pharmacol Exp Ther* 269(1):271-281.

Shannon HE, Rasmussen K, Bymaster FP, Hart JC, Peters SC, Swedberg MD, Jeppesen L, Sheardown MJ, Sauerberg P, Fink-Jensen A (2000) Xanomeline, an M(1)/M(4) preferring muscarinic cholinergic receptor agonist, produces antipsychotic-like activity in rats and mice. *Schizophr Res* 42:249-259.

Shapiro DA, Renock S, Arrington E, Chiodo LA, Liu LX, Sibley DR, Roth BL, Mailman R. Aripiprazole, a novel atypical antipsychotic drug with a unique and robust pharmacology. *Neuropsychopharmacology.* Aug 2003;28(8):1400-11.

Shapleske J, Mickay AP, Mckenna PJ. Successful treatment of tardive dystonia with clozapine and clonazepam. *Br J Psychiatry.* Apr. 1996;168(4):516-8.

Smits et al., Characterization of the histamine $H_4$ receptor binding site. Part 1. Synthesis and pharmacological evaluation of dibenzodiazepine derivatives (2006), J. Med. Chem. 49:4512-4516.

Snyder S, Greenberg D, Yamamura HI (1974) Anti-schizophrenic drugs and brain cholinergic receptors. Affinity for muscarinic sites predicts extrapyramidal effects. *Arch Gen Psychiatry* 31:58-61.

Spalding et al., Mol. Pharm. 70:1974-83 (2006).

Spalding TA, Trotter C, Skjaerbaek N, Messier TL, Currier EA, Burstein ES, Li D, Hacksell U, Brann MR (2002) Discovery of an ectopic activation site on the M(1) muscarinic receptor. *Mol Pharmacol* 61:1297-1302.

Spina E, Avenoso A, Facciola G, Salemi M, Scordo MG, Ancione M, Madia AG, Perucca E (2001) Relationship between plasma risperidone and 9-hydroxyrisperidone concentrations and clinical response in patients with schizophrenia. *Psychopharmacology* 153:238-243.

Spina, E., et al., "Effect of fluoxetine on the plasma concentrations of clozapine and its major metabolites in patients with schizophrenia," International Clinical Psychopharmacology, 13:141-145, 1998.

Sridhar, N, New promises for schizophrenia therapy, Drug Discovery Today, 7(4):215-216 (2002).

Stanhope, K.J., The muscarinic receptor agonist xanomeline has an antipsychotic-like profile in the rat, JPET, 299(2):782-792 (2001).

Steiner, Gerd et al., Tricyclic epines. Novel (E)- and (Z)-11H-dibenz[b,e]azepines as potential central nervous system agents. Variation of the basic side chain. Journal of Medicinal Chemistry, 29(10):1877-88 (1986).

Strange PG. Antipsychotic drugs: importance of dopamine receptors for mechanisms of therapeutic actions and side effects. *Pharmacol Rev.* Mar. 2001;53(1):119-33.

Sur C, Mallorga PJ, Wittmann M, Jacobsen MA, Pascarella D, Williams JB, Brandish PE, Pettibone DJ, Scolnick EM and Conn PJ (2003). N-desmethylclozapine, an allosteric agonist at muscarinic 1 receptor, potentiates N-methyl-d-aspartate receptor activity. *PNAS*, 100: 13674-13679.

Tamminga CA, Carlsson A. Partial dopamine agonists and dopaminergic stabilizers, in the treatment of psychosis. *Curr Drug Targets CNS Neurol Disord.* Apr. 2002;1(2):141-7.

Tamminga CA. Partial dopamine agonists in the treatment of psychosis. *J Neural Transm.* Mar. 2002;109(3):411-20.

Trugman JM, Leadbetter R, Zalis ME, Burgdorf RO, Wooten GF. Treatment of severe axial tardive dystonia with clozapine: case repor+A93t and hypothesis. *Mov Disord*. Jul. 1994;9(4):441-6.

Warawa E J. et al: Behavioral approach to nondyskinetic dopamine antagonists: Identification of Seroquel, Journal of Medicinal Chemistry, American Chemical Society, vol. 44, Feb. 2001 pp. 372- 389.

Weigmann H, Harter S, Fischer V, Dahmen N and Hiemke C (1999). Distribution of clozapine and desmethylclozapine between blood and brain in rats. *Eur Neuropsychopharm*, 9: 253-256.

Weigmann, H., et al., "Does the pharmacologically active N-demethylated metabolite of clozapine pass the blood-brain barrier?" Pharmacopsychiatry, and "20th Symposium of AGNP, Nuremberg, Germany," 30:5(233), Sep. 1997.

Weiner D M. et al., The role of M1 muscarinic receptor agonism of N-desmethylclozapine in the unique clinical effects of clozapine, Psychopharmacology, vol. 177, No. 1-2, Dec. 2004, pp. 207-216, published online Jul. 16, 2004.

Weiner DM, Burstein ES, Nash N, Croston GE, Currier EA, Vanover KE, Harvey SC, Donohue E, Hansen HC, Andersson CM, Spalding TA, Gibson DFC, Krebs-Thomson K, Powell, SB, Geyer MA, Hacksell U, Brann MR (2001)5-hydroxytryptamine2a receptor inverse agonists as antipsychotics. *J Pharmacol Exp Ther* 299:268-276.

Weiner DM, Levey AI, Brann MR (1990) Expression of muscarinic receptor acetylcholine and dopamine receptor mRNA's in rat basal ganglia. *Proc Natl Acad Sci USA*. 87:7050-7054.

Weissman JT, Ma J, Essex A, Gao Y, Burstein ES (2003) G-protein-coupled receptor-mediated activation of rap GTPases: characterization of a novel Gi regulated pathway. *Oncogene* 23(1):241-249.

Wellendorph P, Goodman MW, Burstein ES, Nash NR, Brann MR, Weiner DM (2002) Molecular cloning and pharmacology of functionally distinct isoforms of the human histamine H3 receptor. *Neuropharmacology* 42:929-940.

Wong AH, Van Tol HH (2003) Schizophrenia: from phenomenology to neurobiology. *Neurosci Biobehav Rev* 27(3):269-306.

Wong G, Kuoppamäki M, Hietala J, Lüddens H, Syvälahti E and Korpi ER (1996). Effects of clozapine metabolites and chronic clozapine treatment on rat brain GABAA receptors. *Eur J Pharm*, 314: 319-323.

Young CD, Meltzer HY and Deutch AY (1997). Effects of desmethylclozapine on Fos protein expression in the forebrain: In vivo biological activity of the clozapine metabolite. *Neuropsychopharm*, 19: 99-103.

Zeng, X.P., et al., Muscarinic m4 receptor activation by some atypical antipsychotic drugs, E. Journal of Pharmacol., 321:349-354 (1997).

Zorn SH, Jones SB, Ward KM, Liston DR (1994) Clozapine is a potent and selective muscarinic M4 receptor agonist. *Eur J Pharmacol* 269:R1-R2.

International Search Report, PCT/US2006/012463, dated Sep. 13, 2006.

International Search Report, PCT/US2004/001509 dated Oct. 8, 2004.

International Search Report, PCT/US2005/027645 dated Jan. 20, 2006.

International Search Report, PCT/US2005/010876, dated Dec. 16, 2005.

International Search Report, PCT/US2004/043224, dated Aug. 12, 2005.

International Search Report, PCT/US2006/042464, dated Mar. 8, 2007.

European Search Report, 04704073.8, dated Dec. 20, 2006. Form 2906.

European Search Report, 04704073.8, dated May 31, 2006 Form 1507.

U.S. Appl. No. 11/671,405, WO 2006/17614 Feb. 16, 2006.

U.S. Appl. No. 11/733,476, U.S. 2007/0197502 Aug. 23, 2007.

Bürki et al. " Dibenzo-epines: effect of the basic side-chain on neuroleptic activity", Eur J Med Chem.—Chimica Therapeutica (1978) 13(5): 479-485.

Cacchi et al. "A convenient synthesis of nitrogen-containing heterocycles bearing amino substituents from heteroaryl triflates", *Synlett* (1997) 12:1400-2.

Encyclopedia of Drugs, Moscow, (2001) RLS 421-422.

Konstantinova et al. "11-substituted oiktfkyiridubebenz [b,f][1,4] oxazepines", *Khimiya Geterotsiklicheskikh Soedinenii*, (1989) 4:451-454.

Meltzer et al "Plasma clozapine levels and the treatment of L-DOPA-Induced Psychosis in Parkinson's Disease" *Neuropsychopharma*. (1995) 12(1):39-45-7.

Mikhailov Handbook on Clinical Pharmacology S-Pb (2001) *Foliant* 425-429.

Moroi et al. "Ocular Pharmacology", The Pharmacological Basis of Therapeutics, McGraw-Hill, New York, (1996) 65: 1619-1647.

Moody et al. "Fungal transformation of the tricyclic antidpressant amoxapine: Identification of N-carbomethoxy compounds formed as artifacts by phosgene in chloroform used for the extraction of metabolites", *Biocatalysis and Biotransf.* (2001), 19: 155-161.

Nagarajan et al. "Piperazinylbenzonaphthoxazepines with CNS depressant properties", European J. of Medicinal Chemistry (1986), 21(1): 21-6.

Parnas et al. "Expression and localization of muscarinic receptors in P19-derived neurons", *J of Mol Neuroscience* (1998) 10:17-29.

Practical Handbook on Treatment of Schizophrenia, "Use of neuroleptics upon schizophrenia", Chapter, SMM Psychiatry (2004) 83-112.

Schmutz et al. "Über in 11-Stellung amino-substituierte Dibenzo[b,f]-1,4-thiazepine und -oxazepine—9. Mitteilung über siebengliedrige Heterocyclen", *Helvetica Chimica Acta* (1967), 50(1): 245-54. (Original German).

Schmutz et al. "Constitution chimique et action pharmacologique d'un nouveau groupe de neuroleptiques tricycliques", *Chimica Therapeutica* (1967), 2(6): 424-9 (Original French).

Silveira et al. "Shared psychotic discorder: A critical review of the literature", *Can J Psychiatry* (1995) 40:389-95.

Sindelar et al. "Neurotropic and psychotropic agents", Collection of Czechoslovak Chemical Communications (1978), 43(1): 309-15.

Sumner et al. "Testing the validity of c-fos expression profiling to aid the therapeutic classification of psychoactive drugs" Psychopharmacology (2004) 171:306-321.

Weber et al. "Analysis of the pharmacological properties of clozpine analogs using molecular electrostatic potential surfaces", J. of Molecular Graphics (1986) 4(1): 56-60, 38.

Office Action dated Aug. 10, 2007 in U.S. Appl. No. 11/417,069, filed May 3, 2006.

Office Action dated Oct. 18, 2007 in U.S. Appl. No. 11/417,859, filed May 3, 2006.

Office Action dated Oct. 22, 2007 in U.S. Appl. No. 10/761,787, filed Jan. 21, 2004.

Office Action dated Oct. 23, 2007 in U.S. Appl. No. 11/019,555, filed Dec. 21, 2004.

Office Action dated Dec. 31, 2007 in U.S. Appl. No. 11/417,441, filed May 3, 2006.

Office Action dated Jan. 10, 2008 in U.S. Appl. No. 11/096,756, filed Mar. 31, 2005.

Office Action dated Jan. 16, 2008 in U.S. Appl. No. 11/417,069, filed May 3, 2006.

Office Action dated Feb. 11, 2008 in U.S. Appl. No. 10/913,117, filed Aug. 5, 2004.

International Preliminary Report on Patentability dated Jan. 16, 2006 in PCT/US04/043224, filed Dec. 21, 2004.

International Preliminary Report on Patentability dated May 2, 2005 in PCT/US04/001509, filed Jan. 21, 2004.

International Preliminary Report on Patentability dated Jul. 3, 2006 in PCT/US05/010876, filed Mar. 31, 2005.

International Preliminary Report on Patentability dated Jul. 23, 2005 in PCT/US04/001509, filed Jan. 21, 2004.

International Preliminary Report on Patentability dated Jul. 27, 2007 in PCT/US2006/012463, filed Apr. 3, 2006.

International Preliminary Report on Patentability dated Feb. 6, 2007 in PCT/US05/027645, filed Aug. 4, 2005.

Written Opinion dated Jan. 9, 2008 in PCT/US2006/042464 filed Oct. 31, 2006 (Rule 66).

Russian Examination Report dated Oct. 18, 2007 in Russian Application No. 2005126614/04(029879), filed Aug. 22, 2005.

Acadia Pharmaceuticals announces results from ACP-104 phase lib schizophrenia trial, Press Release Jun. 16, 2008.

Office Action dated May 2, 2008 in U.S. Appl. No. 11/019,555, filed Dec. 21, 2004.

Office Action dated May 20, 2008 in U.S. Appl. No. 10/761,787, filed Jan. 21, 2004.

Office Action dated May 16, 2008 in U.S. Appl. No. 11/417,859, filed May 3, 2006.

Office Action dated Jun. 25, 2008 in U.S. Appl. No. 11/098,892, filed May 5, 2005.

Office Action dated Jul. 14, 2008 in U.S. Appl. No. 11/417,441, filed May 3, 2007.

Notice of Allowance dated Oct. 10, 2008 in U.S. Appl. No. 11/417,441, filed May 3, 2006.

Office Action dated Aug. 19, 2008 in U.S. Appl. No. 10/913,117, filed Aug. 5, 2004.

Notice of Allowance dated Oct. 10, 2008 in U.S. Appl. No. 11/096,756, filed Mar. 31, 2005.

Partial International Search dated Aug. 5, 2008 in PCT/US07/018201, filed Aug. 15, 2007.

International Search Report and Written Opinion dated Nov. 23, 2007 in PCT/US2007/014897 filed Jun. 26, 2007.

Anagnostaras et al., "Selective cognitive dysfunction in acetylcholine $M_1$ muscarinic receptor mutant mice", *Nat Neuroscience* (2003) 6(1): 51-58.

Fisher et al., "$M_1$ muscarinic agonist treatment reverses cognitive and cholinergic impairments of apolipoprotein e-deficient mice", *J Neurochem.* (1998) 70(5): 1991-1997.

Liao et al., "Association of muscarinic $M_1$ receptor genetic polymorphisms with psychiatric symptoms and cognitive function in schizophrenic patients", *Neuropsychobio.* (2003) 48: 72-76.

Terry et al., "Memory-related task performance by aged rhesus monkeys administered the muscarinic $M_1$-preferring agonist, talsaclidine", *Psychopharma.* 162: 292-300, 2002.

Zavitsanou, K., "$M_1$ Receptor agonism, a possible treatment for cognitive deficits in schizophrenia", *Neuropsychopharma.* (2004) 29: 1585-1586.

ACADIA Pharmaceuticals, "Piperizinyl-dibenzooxazepine Compounds", pp. 16, Oct. 27, 2008.

ACADIA Pharmaceuticals announces results from ACP-104 phase lib schizophrenia trial, Press Release Jun. 16, 2008.

Merriam-Webster's Collegiate Dictionary, Tenth Edition (1998), Merriam-Webster, Incorporated, p. 924.

Sunay et al. "Synthesis of carbon-14 and tritium labelled analogs of the novel antischizophrenic agent clozapine", J Label Comp Radiopharma. (1992) 31(12)1041-47.

The Merck Manual, seventeenth Edition (1999), Merck Research Laboratories, pp. 1464-1465.

Office Action dated May 2, 2008 in U.S. Appl. No. 11/019,555, filed Dec. 21, 2004.

Notice of Allowance dated Feb. 11, 2009 in U.S. Appl. No. 11/019,555, filed Dec. 21, 2004.

Notice of Allowance dated Dec. 3, 2008 in U.S. Appl. No. 11/417,859, filed May 3, 2006.

Office Action dated Mar. 27, 2009 in U.S. Appl. No. 11/416,673, filed May 3, 2006.

Office Action dated Feb. 2, 2009 in U.S. Appl. No. 11/590,559, filed Oct. 31, 2006.

AMINO SUBSTITUTED DIARYL[A,D]CYCLOHEPTENE ANALOGS AS MUSCARINIC AGONISTS AND METHODS OF TREATMENT OF NEUROPSYCHIATRIC DISORDERS

RELATED APPLICATIONS

This application is a continuation of U.S. application Ser. No. 11/019,555, filed Dec. 21, 2004, which claims the benefit of U.S. Provisional Application Nos. 60/531,927, filed Dec. 22, 2003; 60/548,090, filed Feb. 24, 2004; and 60/548,604, filed Feb. 27, 2004; all of which are incorporated herein by reference in their entirety.

BACKGROUND OF THE INVENTION

1. Field of the Invention

Certain aspects of the present disclosure relate to methods for treatment of neuropsychiatric disorders, pain and other disorders by compounds that modulate the activity of muscarinic receptors, in particular the subtypes M1, thereby modulating neuronal activities associated with the development of neuropsychiatric disorders. Aspects of the invention also relate to compounds that selectively interact with this receptor subtype and methods of identifying said compounds.

2. Description of the Related Art

Muscarinic cholinergic receptors mediate the actions of the neurotransmitter acetylcholine in the central and peripheral nervous systems, gastrointestinal system, heart, endocrine glands, lungs, and other tissues. Muscarinic receptors play a central role in the central nervous system for higher cognitive functions, as well as in the peripheral parasympathetic nervous system. Five distinct muscarinic receptor subtypes have been identified, m1-m5. The m1 subtype is the predominant subtype found in the cerebral cortex and is believed to be involved in the control of cognitive functions; m2 is the predominant subtype found in heart and is believed to be involved in the control of heart rate; m3 is believed to be involved in gastrointestinal and urinary tract stimulation as well as sweating and salivation; m4 is present in brain and may be involved in locomotion; and m5, present in brain, may be involved in certain functions of the central nervous system associated with the dopaminergic system.

Conditions associated with cognitive impairment, such as Alzheimer's disease, are accompanied by loss of acetylcholine in the brain. This is believed to be the result of degeneration of cholinergic neurons in the basal forebrain, which innervate areas of the association cortex, and hippocampus, which is involved in higher processes.

Efforts to increase acetylcholine levels have focused on increasing levels of choline, the precursor for acetylcholine synthesis, and on blocking acetylcholine esterase (AChE), the enzyme that metabolizes acetylcholine. Administration of choline or phosphatidylcholine has not been very successful. ACHE inhibitors have shown some therapeutic efficacy, but may cause cholinergic side effects due to peripheral acetylcholine stimulation, including abdominal cramps, nausea, vomiting, diarrhea, anorexia, weight loss, myopathy and depression. Gastrointestinal side effects have been observed in about a third of the patients treated. In addition, some ACHE inhibitors, such as tacrine, have also been found to cause significant hepatotoxicity, with elevated liver transaminases observed in about 30% of patients. The adverse effects of ACHE inhibitors have limited their clinical utility.

Known m1 muscarinic agonists such as arecoline have also been found to be weak agonists of m2 as well as m3 subtype and are not very effective in treating cognitive impairment, most likely because of dose-limiting side effects.

There is a need for compounds that increase acetylcholine signaling or effect in the brain. Specifically there is a need for muscarinic agonists that are active at various muscarinic receptor subtypes in the central and peripheral nervous system. Furthermore, there is a need for more highly selective muscarinic agonists, such as m1- or m4-selective agents, both as pharmacological tools and as therapeutic agents.

SUMMARY OF THE INVENTION

Disclosed herein is a compound of Formula I, II, or XV:

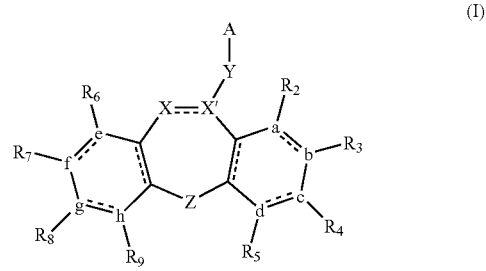

(I)

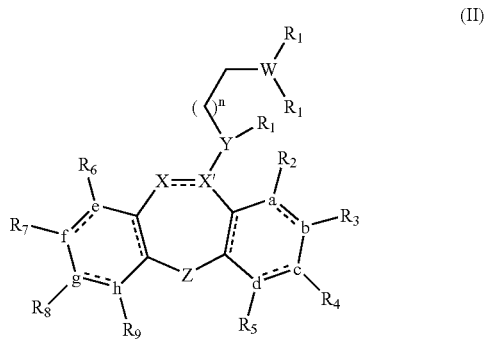

(II)

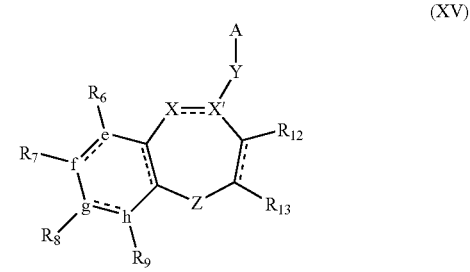

(XV)

or a pharmaceutically acceptable salt, ester, amide, or prodrug thereof, wherein A is selected from the group consisting of

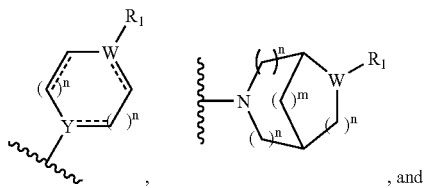

, and

-continued

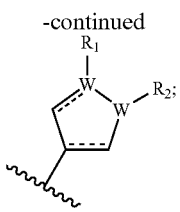

X is nitrogen, CH, or CH$_2$; X' is C or CH, wherein when X' is C, there is a double bond between X and X' and wherein when X' is CH, there is a single bond between X and X'; each Y is separately selected from the group consisting of nitrogen, oxygen, or CH; each W is separately selected from the group consisting of nitrogen, CH, oxygen, or sulfur; each n is separately selected from the group consisting of 0, 1, 2, 3, and 4; m is selected from the group consisting of 1, 2, and 3; each R$_1$ is separately absent or is separately selected from the group consisting of hydrogen, halogen, amine, optionally substituted C$_{1-20}$ alkyl, optionally substituted C$_{3-8}$ cycloalkyl, optionally substituted C$_{2-20}$ alkenyl, optionally substituted C$_{2-20}$ alkynyl, optionally substituted C$_{1-20}$-alkoxyalkyl, and optionally substituted aryl and arylalkyl; L is absent or is selected from the group consisting of —NH(CH$_2$)$_n$— and —(CH$_2$)$_n$—; a, b, c, and d are each independently selected from the group consisting of carbon, nitrogen, oxygen, and sulfur, or each is independently absent, provided that at least three of a, b, c, or d are present, provided that at least one of a, b, c, or d is carbon, and provided that no two adjacent a, b, c, or d are both oxygen or both sulfur; e, f, g, and h are each independently selected from the group consisting of carbon, nitrogen, oxygen, and sulfur, or each is independently absent, provided that at least three of e, f, g, or h are present, provided that at least one of e, f, g, or h is carbon, and provided that no two adjacent e, f, g, or h are both oxygen or both sulfur; R$_2$, R$_3$, R$_4$, and R$_5$, are each independently selected from the group consisting of hydrogen, halogen, optionally substituted C$_{1-6}$ alkyl, optionally substituted C$_{1-6}$ alkyloxy, optionally substituted C$_{2-6}$ alkenyl, optionally substituted C$_{2-6}$ alkynyl, optionally substituted C$_{1-6}$-alkoxyalkyl, optionally substituted C$_{1-6}$ alkylthio, perhaloalkyl, CN, COR$_{10}$, CONHR$_{10}$, NHCONHR$_{10}$, SO$_2$NHR$_{10}$, SO$_2$R$_{10}$, OSO$_2$R$_{10}$, heteroalkyl, NO$_2$, NHCOR$_{10}$, or R$_2$ and R$_3$, or R$_3$ and R$_4$, or R$_4$ and R$_5$ taken together, along with the ring carbons to which they are attached, form a five-membered or six-membered cycloalkyl, heterocyclyl or heteroaryl ring, or a six-membered aryl ring moiety; R$_6$, R$_7$, R$_8$, and R$_9$, are each independently selected from the group consisting of hydrogen, halogen, optionally substituted C$_{1-6}$ alkyl, optionally substituted C$_{1-6}$ alkyloxy, optionally substituted C$_{2-6}$ alkenyl, optionally substituted C$_{2-6}$ alkynyl, optionally substituted C$_{1-6}$-alkoxyalkyl, optionally substituted C$_{1-6}$ alkylthio, perhaloalkyl, CN, COR$_{10}$, CONHR$_{10}$, NHCONHR$_{10}$, SO$_2$NHR$_{10}$, SO$_2$R$_{10}$, OSO$_2$R$_{10}$, heteroalkyl, NO$_2$, NHCOR$_{10}$, or R$_6$ and R$_7$, or R$_7$ and R$_8$, or R$_8$ and R$_9$ taken together, along with the ring carbons to which they are attached, form a five-membered or six-membered cycloalkyl, heterocyclyl or heteroaryl ring, or a six-membered aryl ring moiety; Z is selected from the group consisting of NR$_{11}$, oxygen, sulfur, and CH$_2$; R$_{10}$ is selected from the group consisting of hydrogen, optionally substituted C$_{1-6}$ alkyl, optionally substituted C$_{3-8}$ cycloalkyl, optionally substituted C$_{2-6}$ alkenyl, optionally substituted C$_{2-6}$ alkynyl optionally substituted aryl, optionally substituted arylalkyl, and perhaloalkyl; and R$_{11}$ is selected from the group consisting of hydrogen, optionally substituted C$_{1-6}$ alkyl, optionally substituted C$_{3-8}$ cycloalkyl, optionally substituted C$_{2-6}$ alkenyl, optionally substituted C$_{2-6}$ alkynyl, and optionally substituted arylalkyl; R$_{12}$ and R$_{13}$ are separately selected from the group consisting of hydrogen, halogen, optionally substituted C$_{1-6}$ alkyl, optionally substituted C$_{1-6}$ alkyloxy, optionally substituted C$_{2-6}$ alkenyl, optionally substituted C$_{2-6}$ alkynyl, optionally substituted C$_{1-16}$-alkoxyalkyl, optionally substituted C$_{1-6}$ alkylthio, perhaloalkyl, CN, COR$_{10}$, CONHR$_{10}$, NHCONHR$_{10}$, SO$_2$NHR$_{10}$, SO$_2$R$_{10}$, OSO$_2$R$_{10}$, heteroalkyl, NO$_2$, NHCOR$_{10}$, or R$_{12}$ and R$_{13}$, taken together, along with the ring carbons to which they are attached, form a five-membered or six-membered cycloalkyl, heterocyclyl or heteroaryl ring, or a six-membered aryl ring moiety; and any bond represented by a dashed and solid line represents a bond selected from the group consisting of a carbon-carbon single bond and a carbon-carbon double bond; provided that the compound of Formulae I or XV are not clozapine or N-desmethylclozapine.

In some embodiments, the compound has a structure set forth in Formulas III or IV.

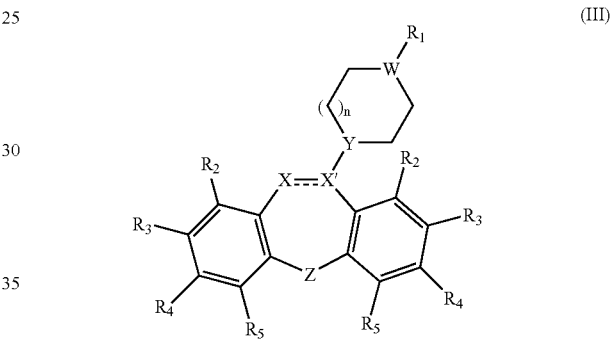

In some embodiments, the compound is selected from the group consisting of:

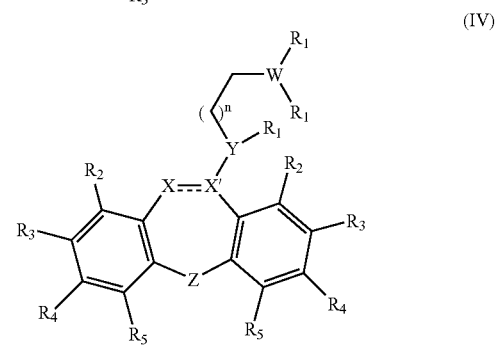

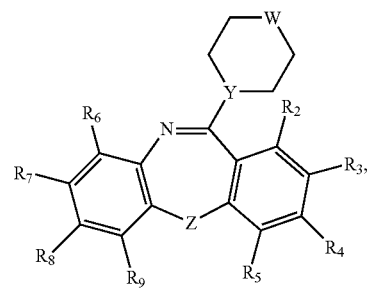

-continued

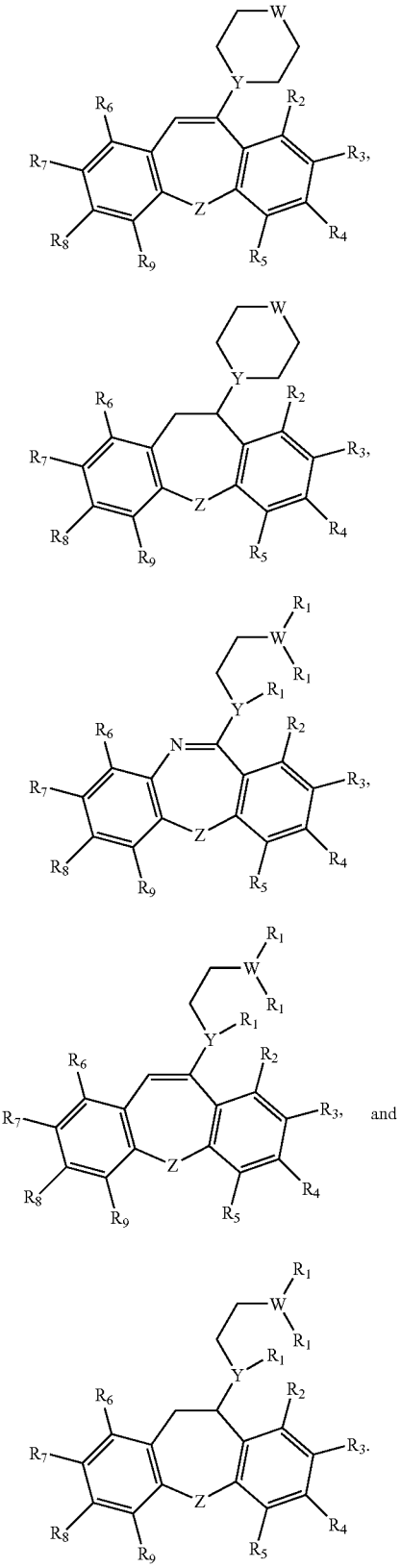

In some embodiments, the compound is selected from the group consisting of:

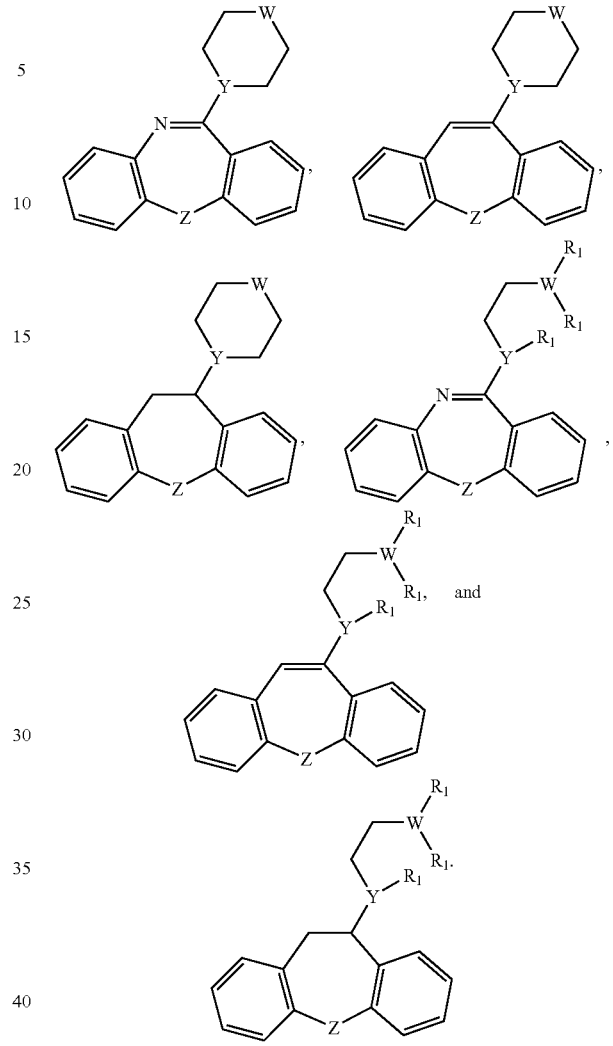

In some embodiments, none of a, b, c, or d is absent. In some embodiments, none of e, f, g, or h is absent. In some embodiments a, b, c, and d are carbon. In some embodiments e, f, g, and h are carbon. In some embodiments, $R_2$ is selected from the group consisting of hydrogen, halogen, optionally substituted $C_{1-6}$ alkyl, and optionally substituted $C_{1-6}$ alkyloxy. In some embodiments, the alkyl is selected from the group consisting of methyl, ethyl, propyl, isopropyl, butyl, sec-butyl, and tert-butyl. In some embodiments, the alkyloxy is selected from the group consisting of methoxy, ethoxy, propoxy, isopropoxy, butoxy, sec-butoxy, and tert-butoxy. In some embodiments, the halogen is selected from the group consisting of fluoro, chloro, and bromo. In some embodiments, $R_2$ is selected from the group consisting of hydrogen, methyl, methoxy, and chloro. In some embodiments, $R_3$ is selected from the group consisting of hydrogen, halogen, optionally substituted $C_{1-6}$ alkyl, optionally substituted $C_{1-6}$ alkyloxy, and $NO_2$. In some embodiments, the alkyl is selected from the group consisting of methyl, ethyl, propyl, isopropyl, butyl, sec-butyl, and tert-butyl. In some embodiments, the alkyloxy is selected from the group consisting of methoxy, ethoxy, propoxy, isopropoxy, butoxy, sec-butoxy, and tert-butoxy. In some embodiments, the halogen is selected from the group consisting of chloro, bromo, and iodo. In some embodiments, $R_3$ is selected from the group consisting of hydrogen, methyl, methoxy, chloro, bromo, iodo, and $NO_2$. In some embodiments, $R_4$ is selected from the group consisting of hydrogen, halogen, optionally substituted $C_{1-6}$ alkyl, perhaloalkyl, $SO_2R_{10}$, and $NO_2$. In some embodiments, the alkyl is selected from the group consisting of methyl, ethyl, propyl, isopropyl, butyl, sec-butyl, and tert-butyl. In some embodiments, the perhaloalkyl is perfluoroalkyl. In some embodiments, the perfluoroalkyl is trifluoromethyl. In some embodiments, the halogen is selected from the group consisting of fluoro, chloro, and bromo. In some embodiments, $R_{10}$ is hydrogen or optionally substituted $C_{1-6}$ alkyl, wherein in some embodiments, the alkyl is selected from the group consisting of methyl, ethyl, propyl, isopropyl, butyl, sec-butyl, and tert-butyl. In some embodiments, $R_4$ is selected from the group consisting of hydrogen, methyl, fluoro, chloro, bromo, trifluoromethyl, $SO_2CH_3$, and $NO_2$. In some embodiments, $R_5$ is selected from the group consisting of hydrogen, halogen, and optionally substituted $C_{1-6}$ alkyl, wherein in some embodiments, the alkyl is selected from the group consisting of methyl, ethyl, propyl, isopropyl, butyl, sec-butyl, and tert-butyl and wherein in some embodiments, the halogen is selected from the group consisting of fluoro, chloro, and bromo. In some embodiments, $R_5$ is hydrogen or chloro. In some embodiments, $R_6$ is hydrogen or optionally substituted $C_{1-6}$ alkyl. In some embodiments, $R_6$ is hydrogen. In some embodiments, $R_7$ is selected from the group consisting of hydrogen, halogen, optionally substituted $C_{1-6}$ alkyl, perhaloalkyl, CN, $SO_2R_{10}$, and $NO_2$, wherein in some embodiments, the alkyl is selected from the group consisting of methyl, ethyl, propyl, isopropyl, butyl, sec-butyl, and tert-butyl; wherein in some embodiments, the halogen is selected from the group consisting of fluoro, chloro, and bromo; wherein in some embodiments, perhaloalkyl is perfluoroalkyl; wherein in some embodiments, perfluoroalkyl is trifluoromethyl. In some embodiments, $R_{10}$ is hydrogen or optionally substituted $C_{1-6}$ alkyl, wherein in some embodiments, the alkyl is selected from the group consisting of methyl, ethyl, propyl, isopropyl, butyl, sec-butyl, and tert-butyl. In some embodiments, $R_7$ is selected from the group consisting of hydrogen, methyl, chloro, trifluoromethyl, $SO_2CH_3$, CN, and $NO_2$. In some embodiments, $R_8$ is selected from the group consisting of hydrogen, halogen, optionally substituted $C_{1-6}$ alkyl, wherein in some embodiments, the alkyl is selected from the group consisting of methyl, ethyl, propyl, isopropyl, butyl, sec-butyl, and tert-butyl and wherein in some embodiments, the halogen is selected from the group consisting of fluoro, chloro, and bromo. In some embodiments, $R_8$ is selected from the group consisting of hydrogen, chloro, and bromo. In some embodiments, $R_9$ is selected from the group consisting of hydrogen, halogen, optionally substituted $C_{1-6}$ alkyl, and perhaloalkyl; wherein in some embodiments, the alkyl is selected from the group consisting of methyl, ethyl, propyl, isopropyl, butyl, sec-butyl, and tert-butyl; wherein in some embodiments, the halogen is selected from the group consisting of fluoro, chloro, and bromo; wherein in some embodiments, perhaloalkyl is perfluoroalkyl; wherein in some embodiments, perfluoroalkyl is trifluoromethyl. In some embodiments, $R_9$ is selected from the group consisting of hydrogen, chloro, methyl, and trifluoromethyl. In some embodiments, $R_1$ is selected from the group consisting of hydrogen, optionally substituted $C_{1-6}$ alkyl, and optionally substituted aryl, wherein in some embodiments, the alkyl is selected from the group consisting of methyl, ethyl, propyl, isopropyl, butyl, sec-butyl, and tert-butyl. In some embodiments, $R_1$ is hydrogen. In some embodiments, X is nitrogen. In some embodiments, Y is NH.

In some embodiments, L is absent or is selected from the group consisting of —$NHCH_2$—, —NH—, and —$CH_2$—. In some embodiments, A is selected from the group consisting of:

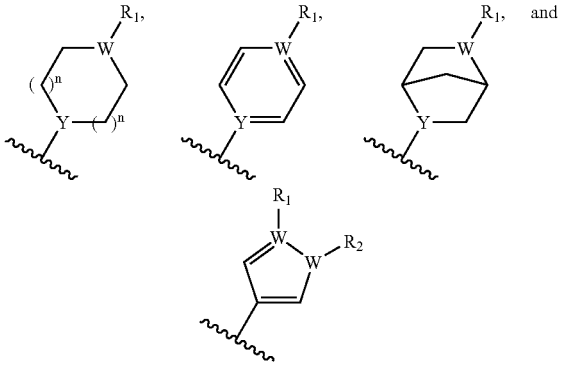

and n is selected from the group consisting of 0, 1, and 2.

Also disclosed herein is a method of synthesizing a compound of Formula V or VI,

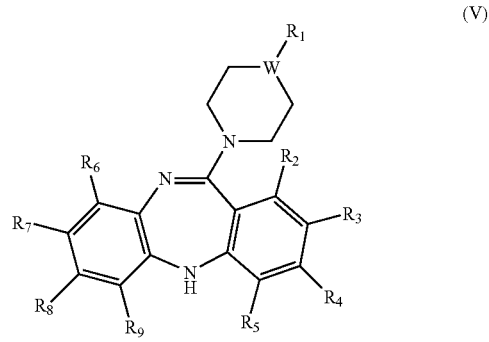

(V)

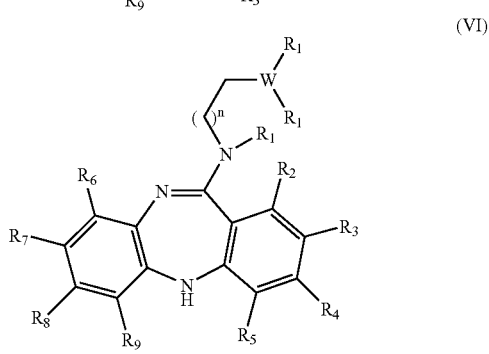

(VI)

comprising reacting a compound of Formula VII

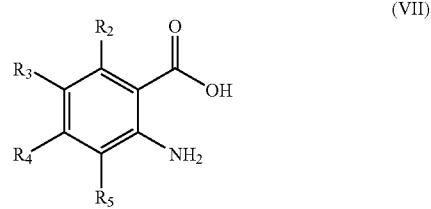

(VII)

with a compound of Formula VIII

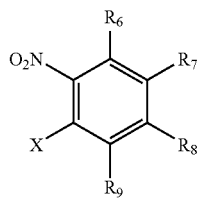
(VIII)

to form a fused ring compound of Formula IX,

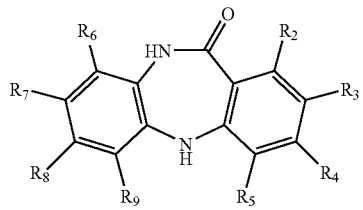
(IX)

and reacting the compound of Formula IX with a compound of Formula X

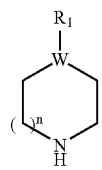
(X)

to obtain a compound of Formula V, wherein X is a halogen; $R_1$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl, optionally substituted $C_{1-6}$-alkoxyalkyl, and optionally substituted aryl and arylalkyl; $R_2$, $R_3$, $R_4$, and $R_5$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_2$ and $R_3$, or $R_3$ and $R_4$, or $R_4$ and $R_5$ taken together, along with the ring carbons to which they are attached, form a five-membered or six-membered cycloalkyl, heterocyclyl or heteroaryl ring, or a six-membered aryl ring moiety; $R_6$, $R_7$, $R_8$, and $R_9$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_6$ and $R_7$, or $R_7$ and $R_8$, or $R_8$ and $R_9$ taken together, along with the ring carbons to which they are attached, form a five-membered or six-membered cycloalkyl, heterocyclyl or heteroaryl ring, or a six-membered aryl ring moiety.

Also disclosed herein is a combinatorial library of at least 220 dibenzo[b,e][1,4]diazepine[a,d]cycloheptene compounds that can be formed by reacting a compound of Formula VII,

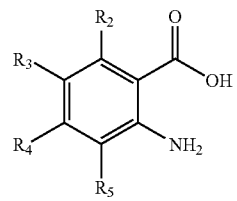
(VII)

with a compound of Formula VIII and

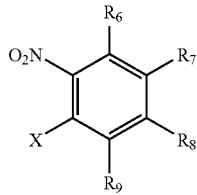
(VIII)

a compound of Formula X,

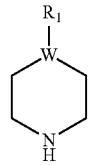
(X)

wherein X is a halogen; $R_1$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl, optionally substituted $C_{1-6}$-alkoxyalkyl, and optionally substituted aryl and arylalkyl; $R_2$, $R_3$, $R_4$, and $R_5$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_2$ and $R_3$, or $R_3$ and $R_4$, or $R_4$ and $R_5$ taken together, along with the ring carbons to which they are attached, form a five-membered or six-membered cycloalkyl, heterocyclyl or heteroaryl ring, or a six-membered aryl ring moiety; $R_6$, $R_7$, $R_8$, and $R_9$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_6$ and $R_7$, or $R_7$ and $R_8$, or $R_8$ and $R_9$ taken together, along with the ring carbons to which they are attached, form a five-membered or six-membered cycloalkyl, heterocyclyl or heteroaryl ring, or a six-membered aryl ring moiety.

Also disclosed herein is a combinatorial library of at least 220 dibenzo[b,e][1,4]diazepine[a,d]cycloheptene compounds that can be formed by reacting a compound of Formula VII,

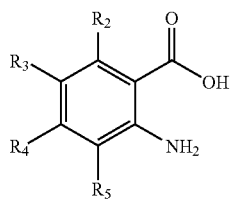

(VII)

with a compound of Formula VIII and

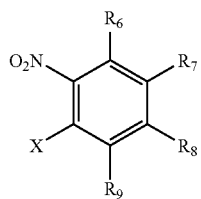

(VIII)

a compound of Formula XII,

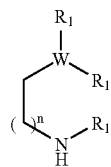

(XII)

wherein X is a halogen; $R_1$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl, optionally substituted $C_{1-6}$-alkoxyalkyl, and optionally substituted aryl and arylalkyl; $R_2$, $R_3$, $R_4$, and $R_5$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_2$ and $R_3$, or $R_3$ and $R_4$, or $R_4$ and $R_5$ taken together, along with the ring carbons to which they are attached, form a five-membered or six-membered cycloalkyl, heterocyclyl or heteroaryl ring, or a six-membered aryl ring moiety; $R_6$, $R_7$, $R_8$, and $R_9$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_6$ and $R_7$, or $R_7$ and $R_8$, or $R_8$ and $R_9$ taken together, along with the ring carbons to which they are attached, form a five-membered or six-membered cycloalkyl, heterocyclyl or heteroaryl ring, or a six-membered aryl ring moiety.

Also disclosed herein is a pharmaceutical composition comprising a physiologically acceptable carrier, diluent, or excipient, or a combination thereof, and a compound of Formula I, II, or XV.

Also disclosed herein is a method of treating a neuropsychiatric disorder comprising administering to the patient a therapeutically effective amount of a compound of Formula I, II, or XV.

Also disclosed herein is a method of treating a neuropsychiatric disorder comprising contacting a therapeutically effective amount of a compound of Formula I, II, or XV with the patient.

Also disclosed herein is a pharmaceutical composition comprising a compound of Formula I, II, or XV and an neuropsychiatric agent. In some embodiments, the neuropsychiatric agent is selected from the group consisting of a selective serotonin reuptake inhibitor, norepinephrine reuptake inhibitor, dopamine agonist, muscarinic receptor antagonist, antipsychotic agent, serotonin 2A antagonist, and inverse serotonin 2A agonist. In some embodiments, the antipsychotic agent is selected from the group consisting of a phenothiazine, phenylbutylpiperadine, debenzapine, benzisoxidil, and salt of lithium. In some embodiments, the phenothiazine is selected from the group consisting of chlorpromazine (Thorazine®), mesoridazine (Serentil®), prochlorperazine (Compazine®), and thioridazine (Mellaril®). In some embodiments, the phenylbutylpiperadines is selected from the group consisting of haloperidol (Haldol®), and pimozide (Orap®). In some embodiments, the debenzapine is selected from the group consisting of clozapine (Clozaril®), loxapine (Loxitane®), olanzapine (Zyprexa®) and quetiapine (Seroquel®). In some embodiments, the benzisoxidil is selected from the group consisting of resperidone (Resperidal®) and ziprasidone (Geodon®). In some embodiments, the salt of lithium is lithium carbonate. In some embodiments, the antipsychotic agent is selected from the group consisting of Clozaril, Compazine, Etrafon, Geodon, Haldol, Inapsine, Loxitane, Mellaril, Moban, Navane, Orap, Permitil, Prolixin, Phenergan, Reglan, Risperdal, Serentil, Seroquel, Stelazine, Taractan, Thorazine, Triavil, Trilafon, and Zyprexa. In some embodiments, the selective serotonin reuptake inhibitor is selected from the group consisting of fluoxetine, fluvoxamine, sertraline, paroxetine, citalopram, escitalopram, sibutramine, duloxetine, and venlafaxine, and pharmaceutically acceptable salts or prodrugs thereof. In some embodiments, the norepinephrine reuptake inhibitor is selected from the group consisting of thionisoxetine and reboxetine. In some embodiments, the dopamine agonist is selected from the group consisting of sumatriptan, almotriptan, naratriptan, frovatriptan, rizatriptan, zomitriptan, cabergoline, amantadine, lisuride, pergolide, ropinirole, pramipexole, and bromocriptine. In some embodiments, the inverse serotonin 2A agonist is the compound of Formula XIII, or a related analog thereof.

(XIII)

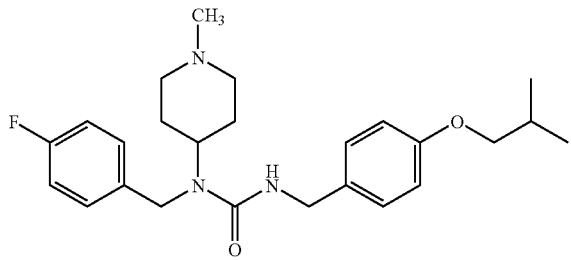

In some embodiments, the serotonin 2A antagonist is the compound of Formula XIV, or a related analog thereof:

(XIV)

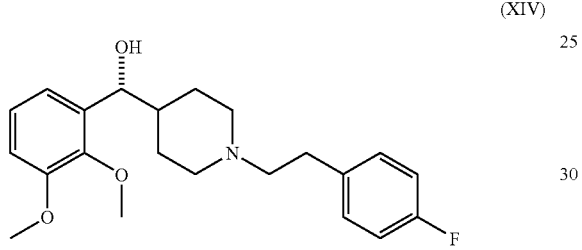

Also disclosed herein is a method of treating neuropsychiatric disorder in a patient comprising administering to the patient a therapeutically effective amount of a pharmaceutical composition comprising a compound of Formula I, II, or XV and an neuropsychiatric agent.

Also disclosed herein is a method of treating neuropsychiatric disorder in a patient comprising administering to the patient a therapeutically effective amount of a compound of Formula I, II, or XV and a therapeutically effective amount of a neuropsychiatric agent. In some embodiments, the administering step comprises administering the compound of Formula I, II, or XV and the neuropsychiatric agent nearly simultaneously. In other embodiments, the administering step comprises administering one of the compound of Formula I, II, or XV and the neuropsychiatric agent first and then administering the other one of the compound of Formula I, II, or XV and the neuropsychiatric agent. In some embodiments, the neuropsychiatric disorder is selected from the group consisting of schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such Alzheimer's or Huntington's Disease.

DETAILED DESCRIPTION OF THE PREFERRED EMBODIMENT

In the first aspect, the present disclosure is related to a compound of Formula I, II, or XV:

(I)

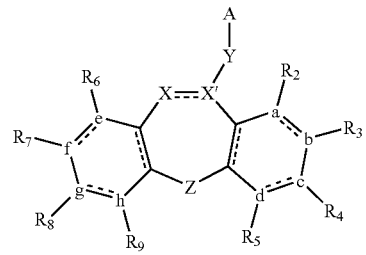

(II)

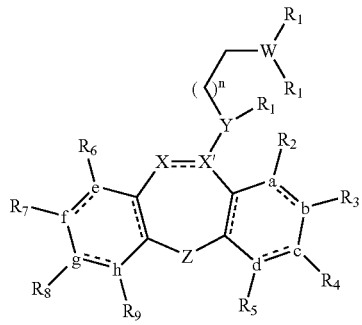

(XV)

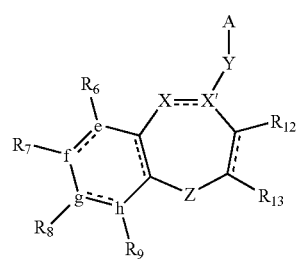

or a pharmaceutically acceptable salt, ester, amide, or prodrug thereof, wherein:

A is selected from the group consisting of

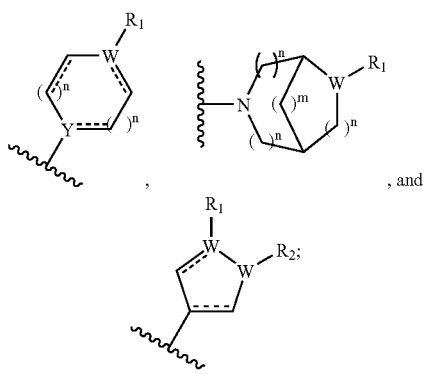

X is nitrogen, CH, or $CH_2$;

X' is C or CH, wherein when X' is C, there is a double bond between X and X' and wherein when X' is CH, there is a single bond between X and X';

each Y is separately selected from the group consisting of nitrogen, oxygen, or CH;

each W is separately selected from the group consisting of nitrogen, CH, oxygen, or sulfur;

each n is separately selected from the group consisting of 0, 1, 2, 3, and 4;

m is selected from the group consisting of 1, 2, and 3;

each $R_1$ is separately absent or is separately selected from the group consisting of hydrogen, halogen, amine, optionally substituted $C_{1-20}$ alkyl, optionally substituted $C_{3-8}$ cycloalkyl, optionally substituted $C_{2-20}$ alkenyl, optionally substituted $C_{2-20}$ alkynyl, optionally substituted $C_{1-20}$-alkoxyalkyl, and optionally substituted aryl and arylalkyl;

L is absent or is selected from the group consisting of —NH(CH$_2$)$_n$— and —(CH$_2$)$_n$—;

a, b, c, and d are each independently selected from the group consisting of carbon, nitrogen, oxygen, and sulfur, or each is independently absent, provided that at least three of a, b, c, or d are present,
provided that at least one of a, b, c, or d is carbon, and
provided that no two adjacent a, b, c, or d are both oxygen or both sulfur;

e, f, g, and h are each independently selected from the group consisting of carbon, nitrogen, oxygen, and sulfur, or each is independently absent, provided that at least three of e, f, g, or h are present,
provided that at least one of e, f, g, or h is carbon, and
provided that no two adjacent e, f, g, or h are both oxygen or both sulfur;

$R_2$, $R_3$, $R_4$, and $R_5$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_2$ and $R_3$, or $R_3$ and $R_4$, or $R_4$ and $R_5$ taken together, along with the ring carbons to which they are attached, form a five-membered or six-membered cycloalkyl, heterocyclyl or heteroaryl ring, or a six-membered aryl ring moiety;

$R_6$, $R_7$, $R_8$, and $R_9$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_6$ and $R_7$, or $R_7$ and $R_8$, or $R_8$ and $R_9$ taken together, along with the ring carbons to which they are attached, form a five-membered or six-membered cycloalkyl, heterocyclyl or heteroaryl ring, or a six-membered aryl ring moiety;

Z is selected from the group consisting of $NR_{11}$, oxygen, sulfur, and $CH_2$;

$R_{10}$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl optionally substituted aryl, optionally substituted arylalkyl, and perhaloalkyl;

$R_{11}$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl, and optionally substituted arylalkyl;

$R_{12}$ and $R_{13}$ are separately selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, heteroalkyl, $NO_2$, $NHCOR_{10}$, or $R_{12}$ and $R_{13}$, taken together, along with the ring carbons to which they are attached, form a five-membered or six-membered cycloalkyl, heterocyclyl or heteroaryl ring, or a six-membered aryl ring moiety.

Bonds represented by a dashed and solid line represents a bond selected from the group consisting of a carbon-carbon single bond and a carbon-carbon double bond. The dashed bond between X and X' in Formulae I, II, and XV indicates that X and X' may be joined by either a single or a double bond.

In certain embodiments, the compound of Formulae I and XV does not include clozapine or N-desmethylclozapine, the structures of which are shown below:

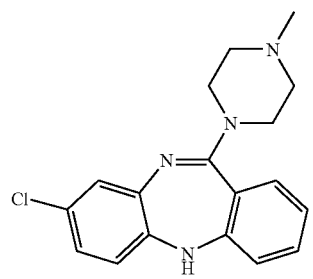

Clozapine

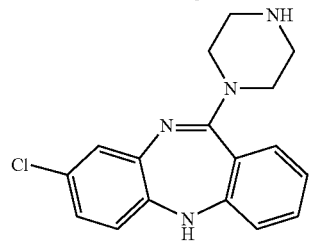

N-desmethylclozapine

In certain embodiments, in compounds of Formulae I and XV, Y is nitrogen or CH. In other embodiments, in compounds of Formula II, Y is nitrogen, oxygen or CH.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g. "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds of the invention may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is (are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The substituent "R" appearing by itself and without a number designation refers to a substituent selected from the group consisting of alkyl, cycloalkyl, aryl, heteroaryl (bonded through a ring carbon) and heteroalicyclic (bonded through a ring carbon).

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group—with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-arnido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include CH₃C(=O)CH₂—, CH₃C(=O)CH₂CH₂—, CH₃CH₂C(=O)CH₂CH₂—, CH₃C(=O)CH₂CH₂CH₂—, and the like.

Unless otherwise indicated, when a substituent is deemed to be "optionally substituted," it is meant that the substituent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

The term "heterocyclyl" is intended to mean three-, four-, five-, six-, seven- and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzofused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

In certain embodiments, disclosed herein is a compound selected from the following structures:
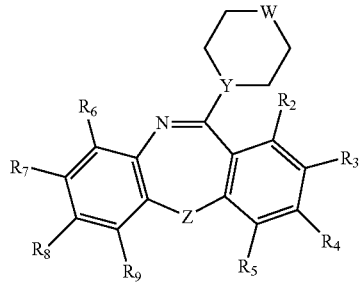
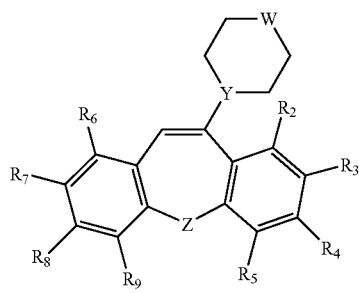
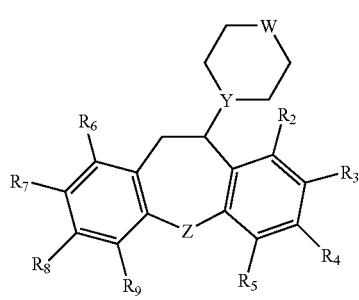
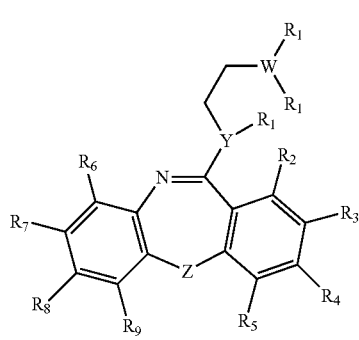
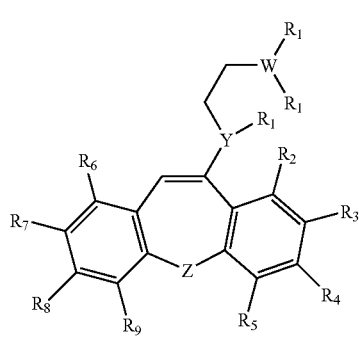
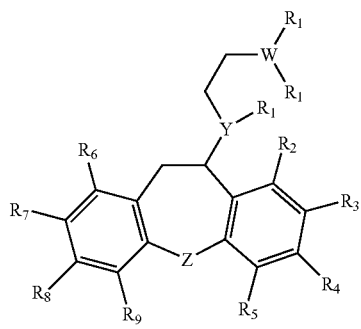
where $R_1$-$R_9$, W, Y, and Z are as described herein.
In certain other embodiments, disclosed herein is a compound selected from the following structures:
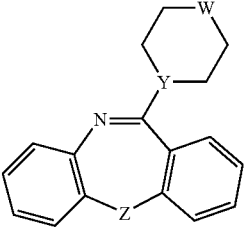 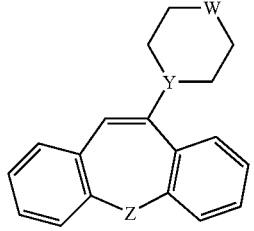
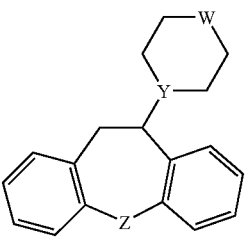 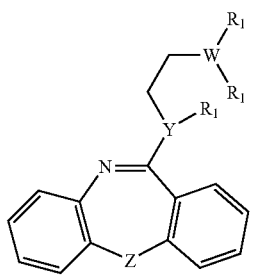
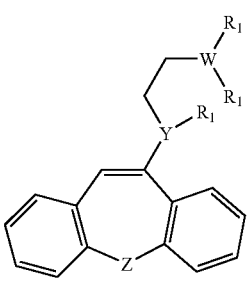 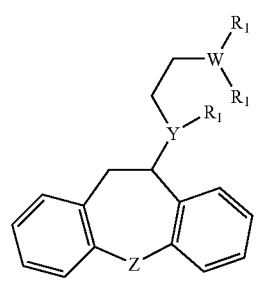
where $R_1$, W, Y, and Z are as described herein.

In certain embodiments, disclosed herein is a compound having a structure set forth in Formula III or Formula IV.

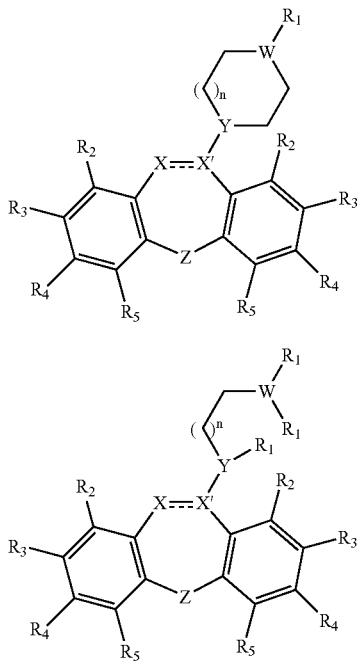

where $R_1$-$R_5$, W, X, X', Y, and Z are as described herein.

In certain embodiments, none of a, b, c, or d is absent, and the ring formed thereby is a six-membered ring. In further embodiments, none of e, f, g, or h is absent, and consequently, the ring formed thereby is a six-membered ring. In some embodiments, a, b, c, and d are carbon, and the ring formed thereby is an optionally substituted phenyl ring. In further embodiments, e, f, g, and h are carbon, which similarly form an optionally substituted phenyl ring.

In certain embodiments, $R_2$ may be selected from the group consisting of hydrogen, halogen, optionally substituted $C_{1-6}$ alkyl, and optionally substituted $C_{1-6}$ alkyloxy. In some embodiments, the alkyl may be selected from the group consisting of methyl, ethyl, propyl, isopropyl, butyl, sec-butyl, and tert-butyl. In other embodiments, the alkyloxy may be selected from the group consisting of methoxy, ethoxy, propoxy, isopropoxy, butoxy, sec-butoxy, and tert-butoxy. In further embodiments, the halogen may be selected from the group consisting of fluoro, chloro, and bromo. In certain embodiments, $R_2$ may be selected from the group consisting of hydrogen, methyl, methoxy, and chloro.

In some embodiments, $R_3$ may be selected from the group consisting of hydrogen, halogen, optionally substituted $C_{1-6}$ alkyl, optionally substituted $C_{1-6}$ alkyloxy, and $NO_2$. The alkyl group may be selected from the group consisting of methyl, ethyl, propyl, isopropyl, butyl, sec-butyl, and tert-butyl, while the alkoxy may be selected from the group consisting of methoxy, ethoxy, propoxy, isopropoxy, butoxy, sec-butoxy, and tert-butoxy. In further embodiments, the halogen may be selected from the group consisting of chloro, bromo, and iodo. In other embodiments, $R_3$ may be selected from the group consisting of hydrogen, methyl, methoxy, chloro, bromo, iodo, and $NO_2$.

In certain embodiments, $R_4$ may be selected from the group consisting of hydrogen, halogen, optionally substituted $C_{1-6}$ alkyl, perhaloalkyl, $SO_2R_{10}$, and $NO_2$. In some embodiments, the alkyl may be selected from the group consisting of methyl, ethyl, propyl, isopropyl, butyl, sec-butyl, and tert-butyl. In further embodiments, the perhaloalkyl may be perfluoroalkyl, which in some embodiments, may be trifluoromethyl. In other embodiments, the halogen may be selected from the group consisting of fluoro, chloro, and bromo. When $R_4$ is $SO_2R_{10}$, the $R_{10}$ may be hydrogen or optionally substituted $C_{1-6}$ alkyl, which alkyl may be selected from the group consisting of methyl, ethyl, propyl, isopropyl, butyl, sec-butyl, and tert-butyl. In certain embodiments, $R_4$ may be selected from the group consisting of hydrogen, methyl, fluoro, chloro, bromo, trifluoromethyl, $SO_2CH_3$, and $NO_2$.

In some embodiments, $R_5$ may be selected from the group consisting of hydrogen, halogen, and optionally substituted $C_{1-6}$ alkyl. The alkyl may be selected from the group consisting of methyl, ethyl, propyl, isopropyl, butyl, sec-butyl, and tert-butyl, while the halogen may be selected from the group consisting of fluoro, chloro, and bromo. In certain embodiments, $R_5$ may be hydrogen or chloro.

In certain embodiments, $R_6$ may be hydrogen or optionally substituted $C_{1-6}$ alkyl. The alkyl may be selected from the group consisting of methyl, ethyl, propyl, isopropyl, butyl, sec-butyl, and tert-butyl. In some embodiments, $R_6$ may be hydrogen.

In certain embodiments, $R_7$ may be selected from the group consisting of hydrogen, halogen, optionally substituted $C_{1-6}$ alkyl, perhaloalkyl, CN, $SO_2R_{10}$, and $NO_2$. The alkyl may be selected from the group consisting of methyl, ethyl, propyl, isopropyl, butyl, sec-butyl, and tert-butyl, while the halogen may be selected from the group consisting of fluoro, chloro, and bromo. In some embodiments, the perhaloalkyl is perfluoroalkyl, which in some embodiments, may be trifluoromethyl. In the embodiments in which $R_7$ may be $SO_2R_{10}$, $R_{10}$ may be hydrogen or optionally substituted $C_{1-6}$ alkyl, which alkyl may be selected from the group consisting of methyl, ethyl, propyl, isopropyl, butyl, sec-butyl, and tert-butyl. In certain embodiments, $R_7$ may be selected from the group consisting of hydrogen, methyl, chloro, trifluoromethyl, $SO_2CH_3$, CN, and $NO_2$.

In some embodiments, $R_8$ may be selected from the group consisting of hydrogen, halogen, optionally substituted $C_{1-6}$ alkyl, which alkyl may be selected from the group consisting of methyl, ethyl, propyl, isopropyl, butyl, sec-butyl, and tert-butyl. The halogen may be selected from the group consisting of fluoro, chloro, and bromo. In certain embodiments, $R_8$ may be selected from the group consisting of hydrogen, chloro, and bromo.

Embodiments of the present disclosure include those in which $R_9$ may be selected from the group consisting of hydrogen, halogen, optionally substituted $C_{1-6}$ alkyl, and perhaloalkyl. The alkyl may be selected from the group consisting of methyl, ethyl, propyl, isopropyl, butyl, sec-butyl, and tert-butyl. The halogen may be selected from the group consisting of fluoro, chloro, and bromo. The perhaloalkyl may be perfluoroalkyl, which in some embodiments may be trifluoromethyl. In some embodiments, $R_9$ may be selected from the group consisting of hydrogen, chloro, methyl, and trifluoromethyl.

In some embodiments, $R_1$ may be selected from the group consisting of hydrogen, optionally substituted $C_{1-6}$ alkyl, and optionally substituted aryl. The alkyl may be selected from the group consisting of methyl, ethyl, propyl, isopropyl, butyl, sec-butyl, and tert-butyl, while the aryl may be phenyl or naphthyl. In other embodiments, $R_1$ may be a heteroaryl. In certain embodiments, $R_1$ may be hydrogen. In certain embodiments, $R_1$ is absent.

In some embodiments, X may be nitrogen. In other embodiments, Y may be NH and W may be nitrogen or CH.

In some embodiments of the compounds of Formula I or Formula XV, L is absent or is selected from the group consisting of —NHCH$_2$—, —NH—, and —CH$_2$—. In some embodiments of the compounds of Formula I or Formula XV, A is selected from the group consisting of:

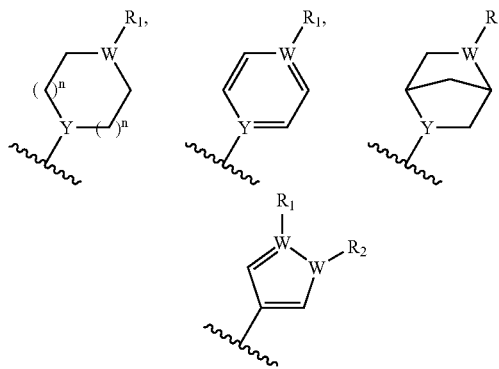

where n is selected from the group consisting of 0, 1, and 2.

Some embodiments of the compounds of Formula I, Formula II, or Formula XV, include:
2,7-Dichloro-11-(piperazin-1-yl)-5H-dibenzo[b,e][1,4]diazepine,
2-Chloro-11-(piperazin-1-yl)-5H-dibenzo[b,e][1,4]diazepine,
2,8-Dichloro-11-(piperazin-1-yl)-5H-dibenzo[b,e][1,4]diazepine,
8-Bromo-2-chloro-11-(piperazin-1-yl)-5H-dibenzo[b,e][1,4]diazepine,
2-Chloro-11-(piperazin-1-yl)-8-trifluoromethyl-5H-dibenzo[b,e][1,4]diazepine,
6-Chloro-11-(piperazin-1-yl)-8-trifluoromethyl-5H-dibenzo[b,e][1,4]diazepine,
7-Chloro-11-(piperazin-1-yl)-5H-dibenzo[b,e][1,4]diazepine,
8-Bromo-1-chloro-11-(piperazin-1-yl)-5H-dibenzo[b,e][1,4]diazepine,
8-Bromo-2-methyl-11-(piperazin-1-yl)-5H-dibenzo[b,e][1,4]diazepine,
4,8-Dichloro-11-(piperazin-1-yl)-5H-dibenzo[b,e][1,4]diazepine,
8-Chloro-2-methyl-11-(piperazin-1-yl)-5H-dibenzo[b,e][1,4]diazepine,
8-Chloro-2-fluoro-11-(piperazin-1-yl)-5H-dibenzo[b,e][1,4]diazepine,
3,8-Dichloro-11-(piperazin-1-yl)-5H-dibenzo[b,e][1,4]diazepine,
2-Bromo-8-chloro-11-(piperazin-1-yl)-5H-dibenzo[b,e][1,4]diazepine,
3,7-Dichloro-11-(piperazin-1-yl)-5H-dibenzo[b,e][1,4]diazepine,
8-Bromo-3-chloro-11-(piperazin-1-yl)-5H-dibenzo[b,e][1,4]diazepine,
3-Chloro-11-(piperazin-1-yl)-5H-dibenzo[b,e][1,4]diazepine,
3-Chloro-11-(piperazin-1-yl)-8-trifluoromethyl-5H-dibenzo[b,e][1,4]diazepine,
7-Chloro-2-methyl-11-(piperazin-1-yl)-5H-dibenzo[b,e][1,4]diazepine,
2-Methyl-11-(piperazin-1-yl)-5H-dibenzo[b,e][1,4]diazepine,
2-Methyl-11-(piperazin-1-yl)-8-trifluoromethyl-5H-dibenzo[b,e][1,4]diazepine,
8-Chloro-4-methyl-11-(piperazin-1-yl)-5H-dibenzo[b,e][1,4]diazepine,
1,8-Dichloro-11-(piperazin-1-yl)-5H-dibenzo[b,e][1,4]diazepine,
8-Bromo-5-methyl-11-(piperazin-1-yl)-5H-dibenzo[b,e][1,4]diazepine,
7,8-Dichloro-11-(piperazin-1-yl)-5H-dibenzo[b,e][1,4]diazepine,
11-(piperazin-1-yl)-8-trifluoromethyl-5H-dibenzo[b,e][1,4]diazepine,
11-(piperazin-1-yl)-5H-dibenzo[b,e][1,4]diazepine,
8-Fluoro-11-(piperazin-1-yl)-5H-dibenzo[b,e][1,4]diazepine,
11-(piperazin-1-yl)-5H-dibenzo[b,e][1,4]diazepine-8-carbonitrile,
8-Bromo-11-(piperazin-1-yl)-5H-dibenzo[b,e][1,4]diazepine,
8-Methyl-11-(piperazin-1-yl)-5H-dibenzo[b,e][1,4]diazepine,
3-Fluoro-6-piperazin-1-yl-11H-dibenzo[b,e]azepine,
2-(Trifluoromethanesulfonyloxy)-11-(piperazin-1-yl)-5H-dibenzo[b,e][1,4]diazepine,
2-(Trifluoromethanesulfonyloxy)-11-(piperazin-1-yl)-5H-dibenzo[b,e][1,4]oxazepine,
8-Chloro-2-(trifluoromethanesulfonyloxy)-11-(piperazin-1-yl)-5H-dibenzo[b,e][1,4]diazepine,
8-(Trifluoromethanesulfonyloxy)-11-(piperazin-1-yl)-5H-dibenzo[b,e][1,4]diazepine,
11-(piperazin-1-yl)-dibenzo[b,f][1,4]thiazepin,
11-(piperazin-1-yl)-2,3-dihydro-1,4-benzodioxino[6,7-b][1,4]benzothiazepin,
8-Chloro-11-[1,4]diazepam-1-yl-5H-dibenzo[b,e][1,4]diazepine,
N'-(8-Chloro-5H-dibenzo[b,e][1,4]diazepine-11-yl)-N,N-dimethyl-ethane-1,2-diamine,
N'-(8-Chloro-5H-dibenzo[b,e][1,4]diazepine-11-yl)-N,N-diethyl-ethane-1,2-diamine,
8-Chloro-11-(4-methyl-[1,4]diazepam-1-yl)-5H-dibenzo[b,e][1,4]diazepine,
8-Chloro-2-methoxy-11-(piperazin-1-yl)-5H-dibenzo[b,e][1,4]diazepine,
N'-(5H-Dibenzo[b,e][1,4]diazepine-11-yl)-N,N-dimethyl-ethane-1,2-diamine,
11-[1,4]Diazepam-1-yl-5H-dibenzo[b,e][1,4]diazepine,
N'-(8-Fluoro-5H-dibenzo[b,e][1,4]diazepine-11-yl)-N,N-dimethyl-ethane-1,2-diamine,
8-Fluoro-11-[1,4]diazepam-1-yl-5H-dibenzo[b,e][1,4]diazepine,
N'-(8-Chloro-5H-dibenzo[b,e][1,4]diazepine-11-yl)-N-methyl-ethane-1,2-diamine,
8-Chloro-11-(trans-2,5-dimethyl-piperazin-1-yl)-5H-dibenzo[b,e][1,4]diazepine,
8-Chloro-11-(3,5-dimethyl-piperazin-1-yl)-5H-dibenzo[b,e][1,4]diazepine,
8-Chloro-11-(3-methyl-piperazin-1-yl)-5H-dibenzo[b,e][1,4]diazepine,
8-Chloro-11-(3-phenyl-piperazin-1-yl)-5H-dibenzo[b,e][1,4]diazepine,
8-Chloro-5-methyl-11-(piperazin-1-yl)-5H-dibenzo[b,e][1,4]diazepine,
8-Chloro-5-benzyl-11-(piperazin-1-yl)-5H-dibenzo[b,e][1,4]diazepine,
8-Iodo-11-(piperazin-1-yl)-5H-dibenzo[b,e][1,4]diazepine, 2-Iodo-8-chloro-11-(piperazin-1-yl)-5H-dibenzo[b,e][1,4]diazepine,
8-Phenyl-11-(piperazin-1-yl)-5H-dibenzo[b,e][1,4]diazepine,
8-Chloro-11-(piperidin-1-yl)-5H-dibenzo[b,e][1,4]diazepine,
8-Chloro-11-(morpholin-4-yl)-5H-dibenzo[b,e][1,4]diazepine,
5-Allyl-8-chloro-11-(piperazin-1-yl)-5H-dibenzo[b,e][1,4]diazepine,
6-Chloro-11-(piperazin-1-yl)-5H-dibenzo[b,e][1,4]diazepine,
8-Chloro-5-piperazin-1-yl-11H-benzo[b]pyrido[2,3-e][1,4]diazepine,
2-Chloro-10-piperazin-1-yl-5H-dibenzo[b,f]azepin,
8-Chloro-11-(piperazin-1-yl)-dibenzo[b,f][1,4]thiazepine,
8-Chloro-11-(piperazin-1-yl)-dibenzo[b,f][1,4]oxazepine,
8-Chloro-11-(4-methyl-piperazin-1-yl)-dibenzo[b,f][1,4]oxazepine,
3-Chloro-6-piperazin-1-yl-11H-dibenzo[b,e]azepine,
8-Bromo-11-(piperazin-1-yl)-dibenzo[b,f][1,4]oxazepine,
11-(piperazin-1-yl)-dibenzo[b,f][1,4]oxazepine,
7-Chloro-11-(piperazin-1-yl)-dibenzo[b,f][1,4]oxazepine,
8-Chloro-3-methoxy-11-(piperazin-1-yl)-dibenzo[b,f][1,4]oxazepine,
8-Bromo-3-methoxy-11-(piperazin-1-yl)-dibenzo[b,f][1,4]oxazepine,
3-Methoxy-11-(piperazin-1-yl)-dibenzo[b,f][1,4]oxazepine,
7-Chloro-3-methoxy-11-(piperazin-1-yl)-dibenzo[b,f][1,4]oxazepine,
8-Chloro-4-methyl-11-(piperazin-1-yl)-dibenzo[b,f][1,4]oxazepine,
8-Bromo-4-methyl-11-(piperazin-1-yl)-dibenzo[b,f][1,4]oxazepine,
4-Methyl-11-(piperazin-1-yl)-dibenzo[b,f][1,4]oxazepine,
2-Bromo-8-chloro-11-(piperazin-1-yl)-dibenzo[b,f][1,4]oxazepine,
2,8-Dibromo-11-(piperazin-1-yl)-dibenzo[b,f][1,4]oxazepine,
2-Bromo-11-(piperazin-1-yl)-dibenzo[b,f][1,4]oxazepine,
2-Bromo-7-chloro-11-(piperazin-1-yl)-dibenzo[b,f][1,4]oxazepine,
11-(piperazin-1-yl)-8-trifluoromethyl-dibenzo[b,f][1,4]oxazepine,
4-Methyl-11-(piperazin-1-yl)-8-trifluoromethyl-dibenzo[b,f][1,4]oxazepine,
8-Fluoro-11-(piperazin-1-yl)-dibenzo[b,f][1,4]oxazepine,
8-Fluoro-3-methoxy-11-(piperazin-1-yl)-dibenzo[b,f][1,4]oxazepine,
8-Fluoro-4-methyl-11-(piperazin-1-yl)-dibenzo[b,f][1,4]oxazepine,
2-Bromo-8-fluoro-11-(piperazin-1-yl)-dibenzo[b,f][1,4]oxazepine,
8-Methyl-11-(piperazin-1-yl)-dibenzo[b,f][1,4]oxazepine,
3-Methoxy-8-methyl-11-(piperazin-1-yl)-dibenzo[b,f][1,4]oxazepine,
4,8-Dimethyl-11-(piperazin-1-yl)-dibenzo[b,f][1,4]oxazepine,
3-Methoxy-11-(piperazin-1-yl)-8-trifluoromethyl-dibenzo[b,f][1,4]oxazepine,
2-Bromo-11-(piperazin-1-yl)-8-trifluoromethyl-dibenzo[b,f][1,4]oxazepine,
6-Chloro-11-(piperazin-1-yl)-dibenzo[b,f][1,4]oxazepine,
2-Bromo-8-methyl-11-(piperazin-1-yl)-dibenzo[b,f][1,4]oxazepine,
7-Chloro-4-methyl-11-(piperazin-1-yl)-dibenzo[b,f][1,4]oxazepine,
8-Phenyl-11-(piperazin-1-yl)-dibenzo[b,f][1,4]oxazepine,
8-Chloro-11-(piperidin-4-yl)-5H-dibenzo[b,e][1,4]diazepine
5-Benzyl-8-chloro-11-(piperidin-4-yl)-5H-dibenzo[b,e][1,4]diazepine,
8-Bromo-5,10-dihydro-dibenzo[b,e][1,4]diazepine-11-one,
5,10-Dihydro-dibenzo[b,e][1,4]diazepine-11-one,
8-Fluoro-5,10-dihydro-dibenzo[b,e][1,4]diazepine-11-one,
8,5-Dichloro-5H-dibenzo[b,e][1,4]diazepine,
8-Chloro-11-methylsulfanyl-5H-dibenzo[b,e][1,4]diazepine
(8-Chloro-5H-dibenzo[b,e][1,4]diazepin-11-yl)-(S)-1-pyrrolidin-2-yl-methyl-amine,
1-(8-Chloro-5H-dibenzo[b,e][1,4]diazepin-11-yl)-piperidine-4-yl-amine,
1-(8-Chloro-5H-dibenzo[b,e][1,4]diazepin-11-yl)-pyrrolidin-3-yl-amine,
(8-Chloro-5H-dibenzo[b,e][1,4]diazepin-11-yl)-(R)-1-pyrrolidin-2-yl-methyl-amine,
(8-Chloro-5H-dibenzo[b,e][1,4]diazepin-11-yl)-pyrrolidin-3-yl-amine,
8-Chloro-11-(2,5-diaza-bicyclo[2.2.1]hept-2-yl)-5H-dibenzo[b,e][1,4]diazepine,
Acetidin-3-yl-(8-chloro-5H-dibenzo[b,e][1,4]diazepine-11-yl)amine,
7-Bromo-4-(piperazin-1-yl)-2,3-dihydro-1H-benzo[b][1,4]diazepine,
7-Bromo-2-methyl-(piperazin-1-yl)-2,3-dihydro-1H-benzo[b][1,4]diazepine
7-Bromo-2-phenyl-4-(piperazine-1-yl)-2,3-dihydro-1H-benzo[b][1,4]diazepine,
7-Bromo-10-(piperazin-1-yl)-1,2,3,3a,4,10a-hexahydro-benzo[b]cyclopenta[e][1,4]diazepine,
8-Chloro-11-(4-fluorobenzyl)-5H-dibenzo[b,e][1,4]diazepine,
8-Chloro-11-(4-fluorophenyl)-5H-dibenzo[b,e][1,4]diazepine,
8-Chloro-11-(4-nonylphenyl)-5H-dibenzo[b,e][1,4]diazepine,
8-Chloro-11-(pyridin-4-yl)-5H-dibenzo[b,e][1,4]diazepine, and
8-Chloro-11-(1H-pyrazol-4-yl)-5H-dibenzo[b,e][1,4]diazepine.

In another aspect, the present disclosure is directed to a method of synthesizing a compound of Formula V or Formula VI,

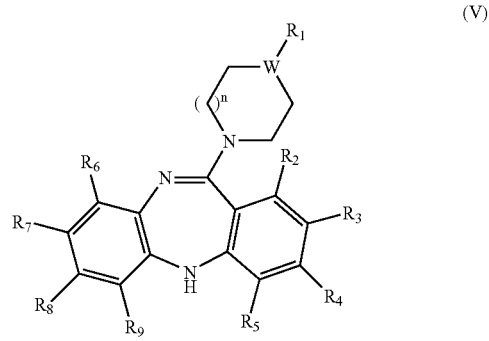

(V)

-continued

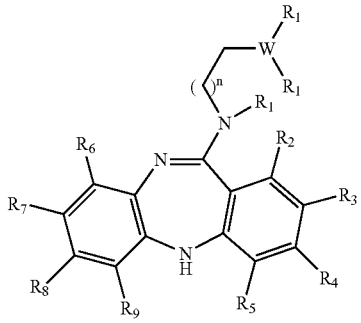

comprising
reacting a compound of Formula VII

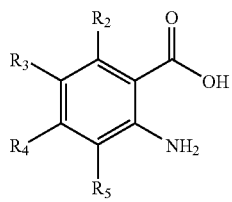

with a compound of Formula VIII

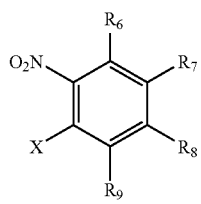

to form a fused ring compound of Formula IX,

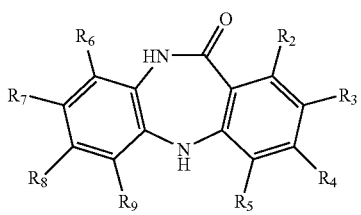

and reacting the compound of Formula IX with a compound of Formula X

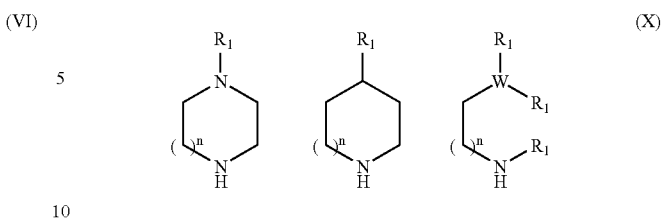

to obtain a compound of Formula V or VI;

wherein X is a halogen; and $R_1$-$R_9$ are as defined herein. In some embodiments, the compound of Formula V synthesized according to the disclosed method is clozapine while in other embodiments, the compound is N-desmethylclozapine. In certain other embodiments, the compound of Formula V synthesized according to the disclosed method does not include clozapine or N-desmethylclozapine.

Consistent with this aspect, Schemes 1 and 2 depict the synthesis of some of the compounds disclosed herein. The first series of steps generating the intermediate lactam have been described by, inter alia, Liao et al. *J. Med. Chem.* 1997, 40, 4146-4153. The last step has been described by e.g. Liao et al. *J. Med. Chem.* 1999, 42, 2235-2244. Both of these references are hereby incorporated herein by reference in their entirety, including any drawings.

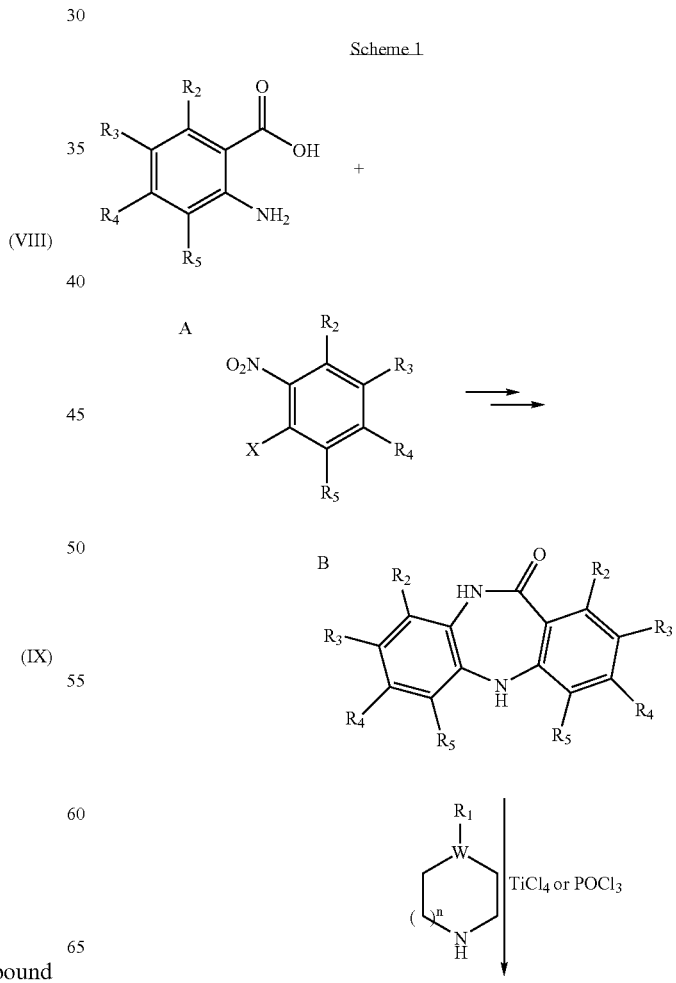

Scheme 1

-continued
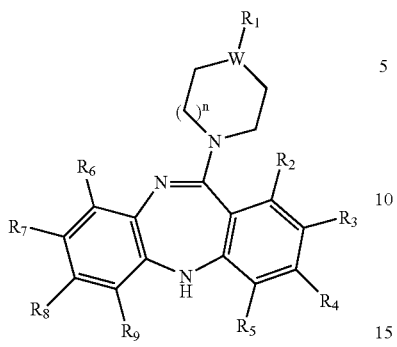
Scheme 2
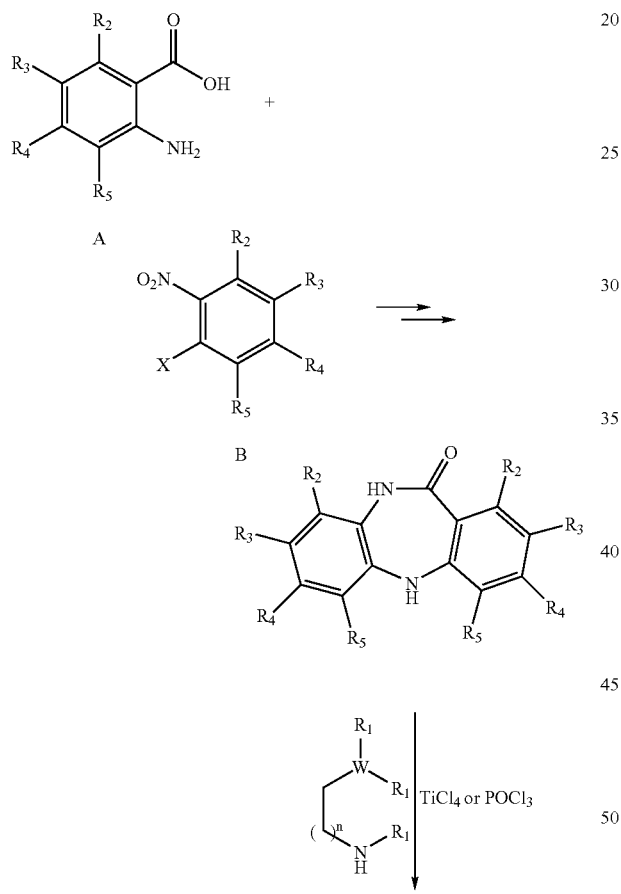
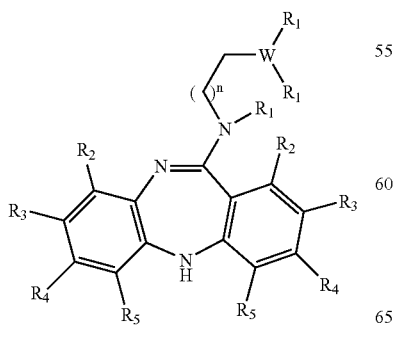
In certain embodiments of the invention the building blocks A and B are selected from but not limited to
| A |
|---|
| 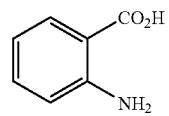 |
| 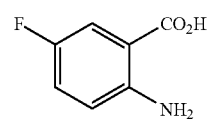 |
| 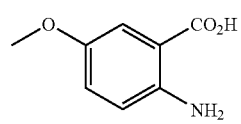 |
| 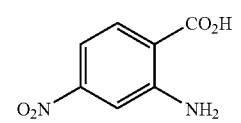 |
| 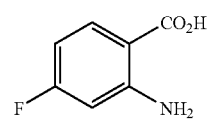 |
| 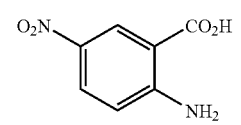 |
| 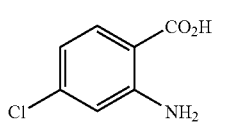 |
| 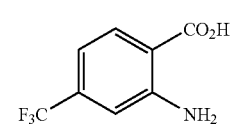 |
| 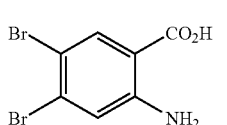 |
| 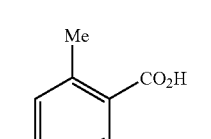 |
| 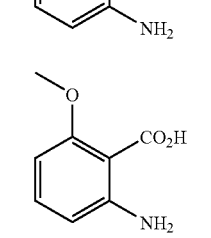 |

-continued
| A |
|---|
| 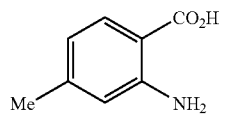 |
| 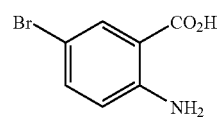 |
| 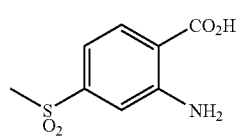 |
| 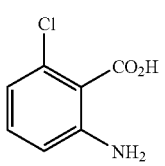 |
| 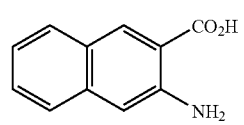 |
| 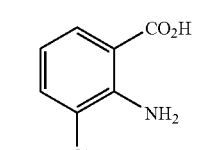 |
| 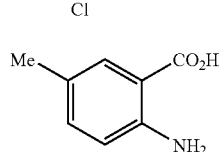 |
| 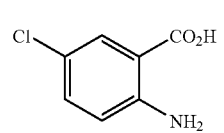 |
| 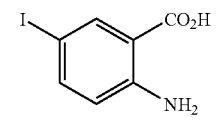 |
| B |
|---|
| 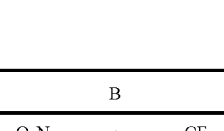 |
-continued
| B |
|---|
| 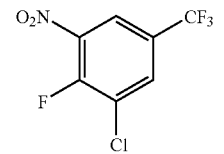 |
| 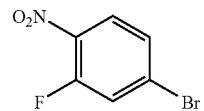 |
| 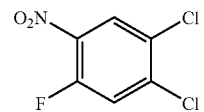 |
| 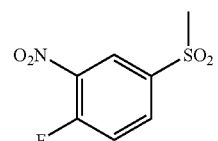 |
| 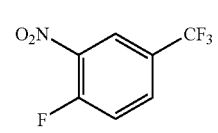 |
| 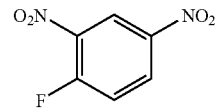 |
| 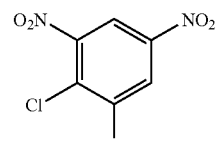 |
| 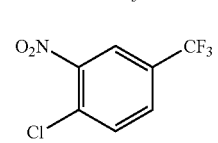 |
| 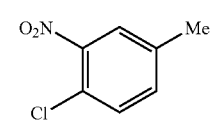 |
| 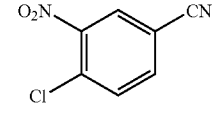 |
| 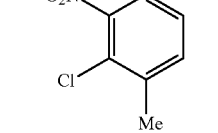 |
In another aspect, the present disclosure relates to a combinatorial library of at least 10, or at least 30, or at least 50, or at least 100, or at least 200, or at least 220 dibenzo[b,e][1,4] diazepine compounds that can be formed by reacting a compound of Formula VII,

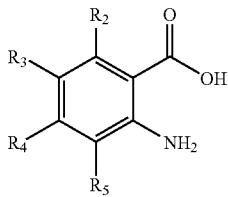

with a compound of Formula VIII and

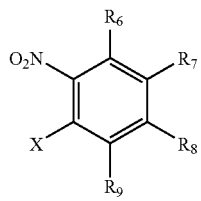

a compound of Formula XI,

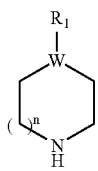

wherein X is a halogen; W is nitrogen, CH, oxygen, or sulfur; n is 1, 2, 3, or 4 and $R_1$-$R_9$ are as defined herein. In some embodiments, the combinatorial library includes clozapine and/or N-desmethylclozapine. In certain other embodiments, the combinatorial library does not include clozapine or N-desmethylclozapine.

In another aspect, the present disclosure relates to a combinatorial library of at least 10, or at least 30, or at least 50, or at least 100, or at least 200, or at least 220 dibenzo[b,e][1,4]diazepine compounds that can be formed by reacting a compound of Formula VII,

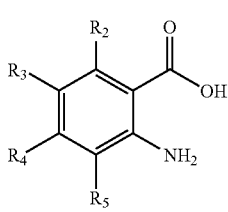

with a compound of Formula VIII and

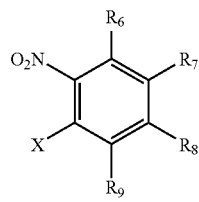

a compound of Formula XII,

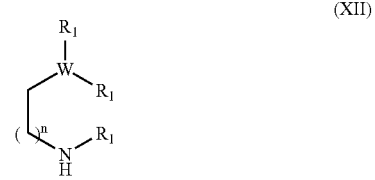

wherein X is a halogen; W is nitrogen, CH, oxygen, or sulfur; n is 1, 2, 3, or 4; and $R_1$-$R_9$ are as defined herein.

As used herein, a "combinatorial library" refers to all the compounds formed by the reaction of each compound of one dimension with a compound in each of the other dimensions in a multi-dimensional array of compounds. In the context of the present disclosure, the array is three dimensional, with one dimension representing all the compounds of Formula VII, the second dimension representing all the compounds of Formula VIII, and the third dimension representing all the compounds of Formula X. Each compound of Formula VII may be reacted with each and every compound of Formula VIII and each and every compound of Formula X in order to form a substituted compound of Formula V or VI. All compounds falling within the scope of Formula V or VI formed in this way are within the scope of the present disclosure. Also within the scope of the present disclosure are smaller combinatorial libraries formed by the reaction of some of, or all of, the compounds of Formula VII with some of, or all of, the compounds of Formula VIII and some of, or all of, the compounds of Formula X.

In some embodiments, compounds of Formulae I, II, or XV, as disclosed and described herein, may be capable of modulating the activity of a muscarinic receptor.

The term "modulate" refers to the ability of a compound disclosed herein to alter the function of a muscarinic receptor. A modulator may activate the activity of a muscarinic receptor, may activate or inhibit the activity of a muscarinic receptor depending on the concentration of the compound exposed to the muscarinic receptor, or may inhibit the activity of a muscarinic receptor. The term "modulate" also refers to altering the function of a muscarinic receptor by increasing or decreasing the probability that a complex forms between a muscarinic receptor and a natural binding partner. A modulator may increase the probability that such a complex forms between the muscarinic receptor and the natural binding partner, may increase or decrease the probability that a complex forms between the muscarinic receptor and the natural binding partner depending on the concentration of the compound exposed to the muscarinic receptor, and or may decrease the probability that a complex forms between the muscarinic receptor and the natural binding partner. In some embodiments, modulation of the muscarinic receptor may be assessed using Receptor Selection and Amplification Technology (R-SAT) as described in U.S. Pat. No. 5,707,798, the disclosure of which is incorporated herein by reference in its entirety.

The term "activate" refers to increasing the cellular function of a muscarinic receptor. The term "inhibit" refers to decreasing the cellular function of a muscarinic receptor. The muscarinic receptor function may be the interaction with a natural binding partner or catalytic activity.

The term "contacting" as used herein refers to bringing a compound disclosed herein and a target muscarinic receptor together in such a manner that the compound can affect the activity of the muscarinic receptor, either directly; i.e., by interacting with the muscarinic receptor itself, or indirectly; i.e., by interacting with another molecule on which the activity of the muscarinic receptor is dependent. Such "contacting" can be accomplished in a test tube, a petri dish or the like. In a test tube, contacting may involve only a compound and a muscarinic receptor of interest or it may involve whole cells. Cells may also be maintained or grown in cell culture dishes and contacted with a compound in that environment. In this context, the ability of a particular compound to affect a muscarinic receptor related disorder; i.e., the $IC_{50}$ of the compound can be determined before use of the compounds in vivo with more complex living organisms is attempted. For cells outside the organism, multiple methods exist, and are well-known to those skilled in the art, to get the muscarinic receptors in contact with the compounds including, but not limited to, direct cell microinjection and numerous transmembrane carrier techniques. The term "contacting" can also refer to bringing a compound disclosed herein to contact with a target muscarinic receptor in vivo. Thus, if a compound disclosed herein, or a prodrug thereof, is administered to an organism and the compound is brought together with a muscarinic receptor within the organism, such contacting is within the scope of the present disclosure.

In some embodiments, the compound of Formulae I, II, or XV may be an agonist of said receptor, while in other embodiments, the compound may be an antagonist of said receptor. In yet other embodiments, the compound may be a partial agonist of said receptor. A compound that is a partial agonists may in some cases be a partial activator of a receptor, while in other cases may be a partial repressor of a receptor. In yet other circumstances, the compound may be a tissue-specific modulator, while in other circumstances, the compound may be a gene-specific modulator.

Certain of the compounds disclosed herein may exist as stereoisomers including optical isomers. The scope of the present disclosure includes all stereoisomers and both the racemic mixtures of such stereoisomers as well as the individual enantiomers that may be separated according to methods that are well known to those of ordinary skill in the art.

In another aspect, the present disclosure relates to a pharmaceutical composition comprising a physiologically acceptable carrier, diluent, or excipient, or a combination thereof, and a compound of Formulae I, II, or XV.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g. by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g. in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insulator may be formulated containing a powder mix of the compound and a suitable powder base such as lactose or starch.

The compounds may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g. sterile pyrogen-free water, before use.

The compounds may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In another aspect, the present disclosure is related to a method of treating a neuropsychiatric disorder comprising administering to said patient a therapeutically effective amount of a compound of Formula I or II. In some embodiments, the neuropsychiatric disorder is selected from the group consisting of schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such Alzheimer's or Huntington's Disease.

In some embodiments, the compound of Formulae I or XV is clozapine while in other embodiments, the compound is N-desmethylclozapine. In certain other embodiments, the compound of Formulae I or XV does not include clozapine or N-desmethylclozapine.

In yet another aspect, the present disclosure is related to a method of treating a neuropsychiatric disorder comprising contacting a therapeutically effective amount of a compound of Formulae I, II, or XV with said patient.

In some embodiments, the present disclosure relates to a pharmaceutical composition comprising a compound of Formula I, II, or XV and a neuropsychiatric agent. As used herein, a "neuropsychiatric agent" refers to a compound, or a combination of compounds, that affects the neurons in the brain either directly or indirectly, or affects the signal transmitted to the neurons in the brain. Neuropsychiatric agents, therefore, may affect a person's psyche, such as the person's mood, perception, nociception, cognition, alertness, memory, etc. In certain embodiments, the neuropsychiatric agent may be selected from the group consisting of a selective serotonin reuptake inhibitor, norepinephrine reuptake inhibitor, dopamine agonist, antipsychotic agent, serotonin 2A antagonists, and inverse serotonin 2A agonists.

In some embodiments, the antipsychotic agent may be selected from the group consisting of a phenothiazine, phenylbutylpiperadine, debenzapine, benzisoxidil, and salt of lithium. The phenothiazine group of compounds may be selected from the group consisting of chlorpromazine (Thorazine®), mesoridazine (Serentil®), prochlorperazine (Compazine®), and thioridazine (Mellaril®). The phenylbutylpiperadine group of compounds may be selected from the group consisting of haloperidol (Haldol®), and pimozide (Orap®). The debenzapine group of compounds may be selected from the group consisting of clozapine (Clozaril®), loxapine (Loxitane®), olanzapine (Zyprexa®) and quetiapine (Seroquel®). The benzisoxidil group of compounds may be selected from the group consisting of resperidone (Resperidal®) and ziprasidone (Geodon®). The salt of lithium may be lithium carbonate. In some embodiments, the antipsychotic agent may be selected from the group consisting of Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa, or pharmaceutically acceptable salts thereof.

In certain embodiments, the selective serotonin reuptake inhibitor is selected from the group consisting of fluoxetine, fluvoxamine, sertraline, paroxetine, citalopram, escitalopram, sibutramine, duloxetine, and venlafaxine, and pharmaceutically acceptable salts or prodrugs thereof.

In other embodiments, the norepinephrine reuptake inhibitor is selected from the group consisting of thionisoxetine and reboxetine.

In further embodiments, the dopamine agonist is selected from the group consisting of sumatriptan, almotriptan, naratriptan, frovatriptan, rizatriptan, zomitriptan, cabergoline, amantadine, lisuride, pergolide, ropinirole, pramipexole, and bromocriptine.

In another embodiment, the inverse serotonin 2A agonist is ACP-103 or an analog thereof. By "ACP-103," it is meant the compound of Formula XIII.

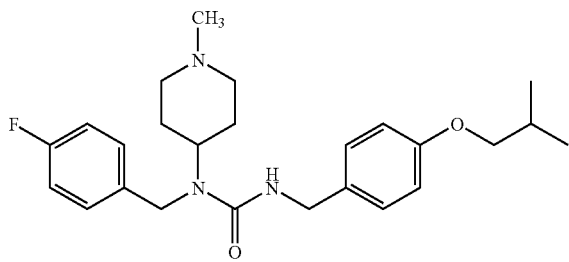

(XIII)

In another embodiment, the serotonin 2A antagonist is M 100,907 or an analog thereof. By "M 100,907," it is meant the compound of Formula XIV.

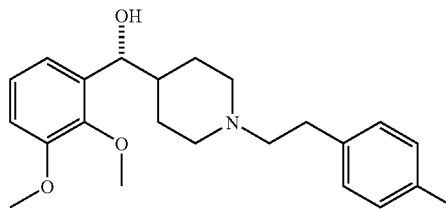

(XIV)

In another aspect, the present disclosure is directed to a method of treating neuropsychiatric disorder in a patient comprising administering to said patient a therapeutically effective amount of a pharmaceutical composition comprising a compound of Formula I, II, or XV and a neuropsychiatric agent. In yet another aspect, the present disclosure is directed to a method of treating neuropsychiatric disorder in a patient comprising administering to said patient a therapeutically effective amount of a compound of Formula I, II, or XV and a therapeutically effective amount of a neuropsychiatric agent.

In certain embodiments, the patient may be a mammal. The mammal may be selected from the group consisting of mice, rats, rabbits, guinea pigs, dogs, cats, sheep, goats, cows, primates, such as monkeys, chimpanzees, and apes, and humans. In some embodiments, the patient is a human.

In some embodiments, the administering step in the above methods comprises administering said compound of Formula I, II, or XV and said neuropsychiatric agent nearly simultaneously. These embodiments include those in which the compound of Formula I or II and the neuropsychiatric agent are in the same administrable composition, i.e., a single tablet, pill, or capsule, or a single solution for intravenous injection, or a single drinkable solution, or a single dragee formulation or patch, contains both compounds. The embodiments also include those in which each compound is in a separate administrable composition, but the patient is directed to take the separate compositions nearly simultaneously, i.e., one pill is taken right after the other or that one injection of one compound is made right after the injection of another compound, etc.

In other embodiments the administering step comprises administering one of the compound of Formula I, II, or XV and the neuropsychiatric agent first and then administering the other one of the compound of Formula I, II, or XV and the neuropsychiatric agent. In these embodiments, the patient may be administered a composition comprising one of the compounds and then at some time, a few minutes or a few hours, later be administered another composition comprising the other one of the compounds. Also included in these embodiments are those in which the patient is administered a composition comprising one of the compounds on a routine or continuous basis while receiving a composition comprising the other compound occasionally.

In certain embodiments, the neuropsychiatric disorder to be treated by the methods and the compounds of the present disclosure is selected from the group consisting of schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such Alzheimer's or Huntington's Disease.

EXAMPLES

Example 1

General Procedure 1 (GP1)

A mixture of an aminobenzoic acid (1 eq.), a 2-fluoronitrobenzene (3 eq.) and Cs$_2$CO$_3$ (3 eq.) in DMF was heated to 140° C. for 1 hour, and then allowed to obtain room temperature. The mixture was diluted with water and washed with EtOAc (2×).

EtOH and Na$_2$S$_2$O$_4$ (5 eq.) was added to the aqueous phase and the resulting mixture was stirred for 1 h. Aqueous HCl (2 M) was added to the mixture and then the aqueous phase was extracted with EtOAc (3×) and the combined organic phases were concentrated.

The residue was taken up in CH$_2$Cl$_2$ and 1-ethyl-3-(3-dimethylaminopropyl)carbodiimide hydrochloride (3 eq.) was added and the resulting mixture was stirred at room temperature for 1 h, and then concentrated. The residue was diluted with EtOAc, washed with aqueous NaOH (2 M) and concentrated.

The residue was taken up in dioxane and added to a mixture of TiCl$_4$ (1.1 eq., 1 M in toluene) and piperazine (5 eq.) in dioxane at 50° C. The resulting mixture was stirred at 100° C. over night, and then allowed to obtain room temperature. Aqueous HCl (2 M) was added to the mixture until the solution became acidic and then the aqueous phase was extracted with EtOAc (2×). Aqueous NaOH (2 M) was added to the aqueous phase until a basic solution was obtained and the resulting suspension was extracted with EtOAc (3×). The combined organic phases were concentrated and purified by HPLC.

Example 2

2,7-Dichloro-11-(piperazin-1-yl)-5H-dibenzo[b,e][1,4]diazepine (166JO85F1)

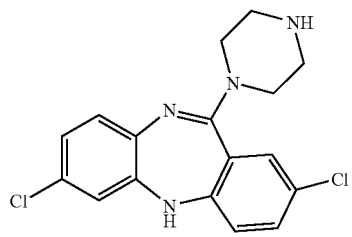

4-Chloro-2-fluoronitrobenzene (263 mg, 1.5 mmol) and 2-amino-5-chlorobenzoic acid (86 mg, 0.5 mmol) were reacted according to GP1 to give 6.1 mg of the title compound (166 JO85F1). MS (ESI) 347 (MH$^+$). Purity for MH$^+$ (UV/MS) 100/85.

Example 3

2-Chloro-11-(piperazin-1-yl)-5H-dibenzo[b,e][1,4]diazepine (166JO85F6)

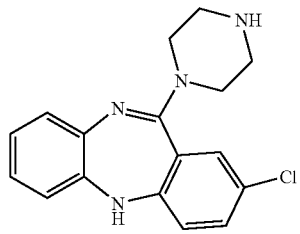

2-Fluoronitrobenzene (212 mg, 1.5 mmol) and 2-amino-5-chlorobenzoic acid (86 mg, 0.5 mmol) were reacted according to GP1 to give 5.3 mg of the title compound (166 JO85F6). MS (ESI) 313 (MH$^+$). Purity for MH$^+$ (UV/MS) 100/95.

Example 4

2,8-Dichloro-11-(piperazin-1-yl)-5H-dibenzo[b,e][1,4]diazepine (166JO85F2)

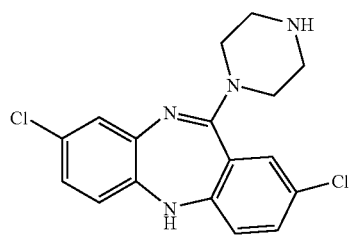

5-Chloro-2-fluoronitrobenzene (263 mg, 1.5 mmol) and 2-amino-5-chlorobenzoic acid (86 mg, 0.5 mmol) were reacted according to GP1 to give 4.8 mg of the title compound (166 JO85F2). MS (ESI) 347 (MH$^+$). Purity for MH$^+$ (UV/MS) 99/99.

Example 5

8-Bromo-2-chloro-11-(piperazin-1-yl)-5H-dibenzo[b,e][1,4]diazepine (166JO85F3)

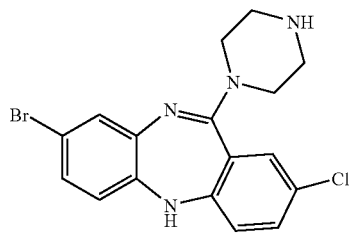

5-Bromo-2-fluoronitrobenzene (330 mg, 1.5 mmol) and 2-amino-5-chlorobenzoic acid (86 mg, 0.5 mmol) were reacted according to GP1 to give 8.0 mg of the title compound (166 JO85F3). MS (ESI) 391 (MH$^+$). Purity for MH$^+$ (UV/MS) 100/96.

Example 6

2-Chloro-11-(piperazin-1-yl)-8-trifluoromethyl-5H-dibenzo[b,e][1,4]diazepine (166JO85F7)

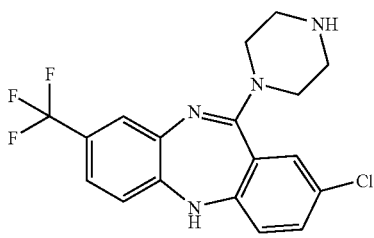

4-Fluoro-3-nitrobenzotrifluoride (314 mg, 1.5 mmol) and 2-amino-5-chlorobenzoic acid (86 mg, 0.5 mmol) were reacted according to GP1 to give 0.3 mg of the title compound (166 JO85F7). MS (ESI) 381 (MH⁺). Purity for MH⁺ (UV/MS) 100/95.

Example 7

6-Chloro-11-(piperazin-1-yl)-8-trifluoromethyl-5H-dibenzo[b,e][1,4]diazepine (189JO77B)

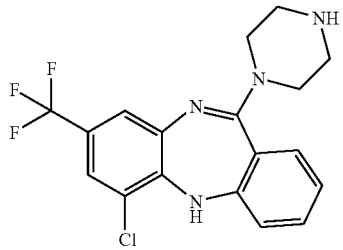

3-Chloro-4-fluoro-5-nitrobenzotrifluoride (366 mg, 1.5 mmol) and 2-aminobenzoic acid (69 mg, 0.5 mmol) were reacted according to GP1 to give 28 mg of the title compound (189JO77B). MS (ESI) 381 (MH⁺). Purity for MH⁺ (UV/MS) 99/100.

Example 8

7-Chloro-11-(piperazin-1-yl)-5H-dibenzo[b,e][1,4]diazepine (160FE35B)

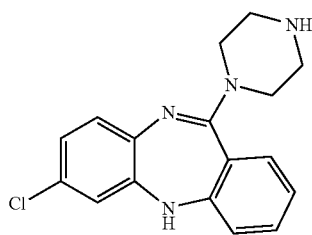

4-Chloro-2-fluoronitrobenzene (528 mg, 3.0 mmol) and 2-aminobenzoic acid (138 mg, 1.0 mmol) were reacted according to GP1 to give 5.0 mg of the title compound (160FE35B). MS (ESI) 313 (MH⁺). Purity for MH⁺ (UV/MS) 99/86.

Example 9

8-Bromo-1-chloro-11-(piperazin-1-yl)-5H-dibenzo[b,e][1,4]diazepine (160FE36A)

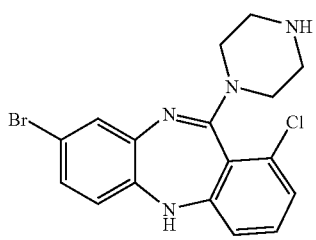

5-Bromo-2-fluoronitrobenzene (660 mg, 3.0 mmol) and 2-amino-6-chlorobenzoic acid (172 mg, 1.0 mmol) reacted according to GP1 to give 5.0 mg of the title compound (160FE36A). MS (ESI) 391 (MH⁺). Purity for MH⁺ (UV/MS) 94/87.

Example 10

8-Bromo-2-methyl-11-(piperazin-1-yl)-5H-dibenzo[b,e][1,4]diazepine (160FE40C)

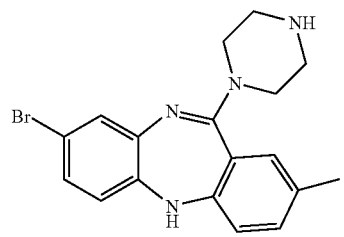

5-Bromo-2-fluoronitrobenzene (660 mg, 3.0 mmol) and 2-amino-5-methylbenzoic acid (152 mg, 1.0 mmol) were reacted according to GP1 to give 7.9 mg of the title compound (160FE40C). MS (ESI) 371 (MH⁺). Purity for MH⁺ (UV/MS) 100/100.

Example 11

4,8-Dichloro-11-(piperazin-1-yl)-5H-dibenzo[b,e][1,4]diazepine (160FE41A)

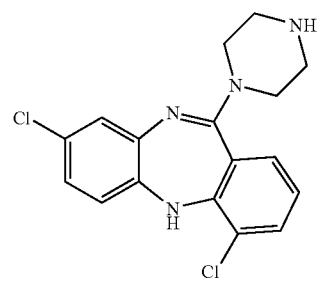

5-Chloro-2-fluoronitrobenzene (527 mg, 3.0 mmol) and 2-amino-3-chlorobenzoic acid (172 mg, 1.0 mmol) were reacted according to GP1 to give 4.6 mg of the title compound (160FE41A). MS (ESI) 347 (MH⁺). Purity for MH⁺ (UV/MS) 95/70.

Example 12

8-Chloro-2-methyl-11-(piperazin-1-yl)-5H-dibenzo[b,e][1,4]diazepine (160FE41B)

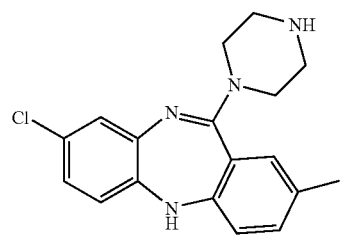

5-Chloro-2-fluoronitrobenzene (527 mg, 3.0 mmol) and 2-amino-5-methylbenzoic acid (151 mg, 1.0 mmol) were

Example 13

8-Chloro-2-fluoro-11-(piperazin-1-yl)-5H-dibenzo[b,e][1,4]diazepine (160FE42A-F3)

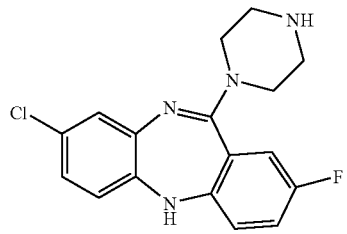

5-Chloro-2-fluoronitrobenzene (264 mg, 1.5 mmol) and 2-amino-5-fluorobenzoic acid (78 mg, 0.5 mmol) were reacted according to GP1 to give 21 mg of the title compound (160FE42A-F3). MS (ESI) 331 (MH$^+$). Purity for MH$^+$ (UV/MS) 99/98.

Example 14

3,8-Dichloro-11-(piperazin-1-yl)-5H-dibenzo[b,e][1,4]diazepine (160FE42B-F4)

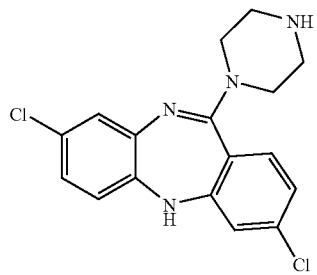

5-Chloro-2-fluoronitrobenzene (264 mg, 1.5 mmol) and 2-amino-4-chlorobenzoic acid (86 mg, 0.5 mmol) were reacted according to GP1 to give 9.4 mg of the title compound (160FE42B-F4). MS (ESI) 347 (MH$^+$). Purity for MH$^+$ (UV/MS) 99/97.

Example 15

2-Bromo-8-chloro-11-(piperazin-1-yl)-5H-dibenzo[b,e][1,4]diazepine (160FE43A-F6)

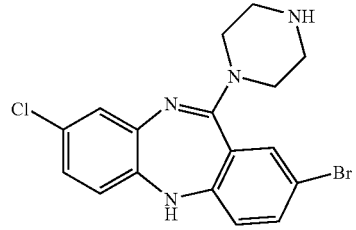

5-Chloro-2-fluoronitrobenzene (528 mg, 3.0 mmol) and 2-amino-5-bromobenzoic acid (216 mg, 1.0 mmol) were reacted according to GP1 to give 20 mg of the title compound (160FE43A-F6). MS (ESI) 391 (MH$^+$). Purity for MH$^+$ (UV/MS) 100/100.

reacted according to GP1 to give 7.1 mg of the title compound (160FE41B). MS (ESI) 327 (MH$^+$). Purity for MH$^+$ (UV/MS) 100/94.

Example 16

3,7-Dichloro-11-(piperazin-1-yl)-5H-dibenzo[b,e][1,4]diazepine (160FE58D1)

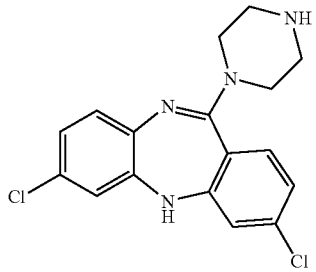

4-Chloro-2-fluoronitrobenzene (263 mg, 1.5 mmol) and 2-amino-4-chlorobenzoic acid (86 mg, 0.5 mmol) were reacted according to GP1 to give 3.1 mg of the title compound (160FE58D1). MS (ESI) 347 (MH$^+$). Purity for MH$^+$ (UV/MS) 63/83.

Example 17

8-Bromo-3-chloro-11-(piperazin-1-yl)-5H-dibenzo[b,e][1,4]diazepine (160FE58D3)

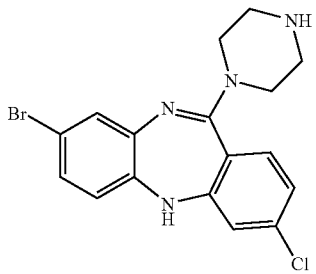

5-Bromo-2-fluoronitrobenzene (330 mg, 1.5 mmol) and 2-amino-4-chlorobenzoic acid (86 mg, 0.5 mmol) were reacted according to GP1 to give 1.1 mg of the title compound (160FE58D3). MS (ESI) 391 (MH$^+$). Purity for MH$^+$ (UV/MS) 90/85.

Example 18

3-Chloro-11-(piperazin-1-yl)-5H-dibenzo[b,e][1,4]diazepine (160FE58D6)

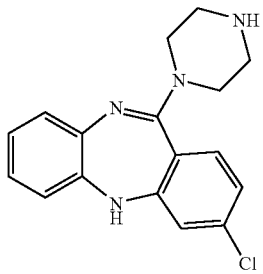

2-Fluoronitrobenzene (212 mg, 1.5 mmol) and 2-amino-4-chlorobenzoic acid (86 mg, 0.5 mmol) were reacted according to GP1 to give 2.2 mg of the title compound (160FE58D6). MS (ESI) 313 (MH$^+$). Purity for MH$^+$ (UV/MS) 90/100.

Example 19

3-Chloro-11-(piperazin-1-yl)-8-trifluoromethyl-5H-dibenzo[b,e][1,4]diazepine (160FE58D7)

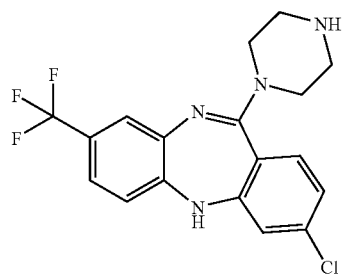

4-Fluoro-3-nitrobenzotrifluoride (314 mg, 1.5 mmol) and 2-amino-4-chlorobenzoic acid (86 mg, 0.5 mmol) were reacted according to GP1 to give 2.0 mg of the title compound (160FE58D7). MS (ESI) 381 (MH$^+$). Purity for MH$^+$ (UV/MS) 100/100.

Example 20

7-Chloro-2-methyl-11-(piperazin-1-yl)-5H-dibenzo[b,e][1,4]diazepine (160FE58E1)

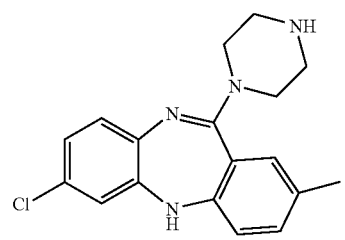

4-Chloro-2-fluoronitrobenzene (263 mg, 1.5 mmol) and 2-amino-5-methylbenzoic acid (76 mg, 0.5 mmol) were reacted according to GP1 to give 1.1 mg of the title compound (160FE58E1). MS (ESI) 327 (MH$^+$). Purity for MH$^+$ (UV/MS) 100/90.

Example 21

2-Methyl-11-(piperazin-1-yl)-5H-dibenzo[b,e][1,4]diazepine (160FE58E6)

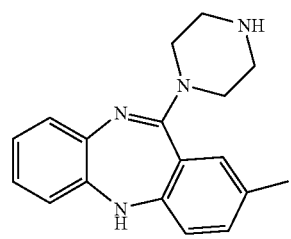

4-Fluoronitrobenzene (212 mg, 1.5 mmol) and 2-amino-5-methylbenzoic acid (76 mg, 0.5 mmol) were reacted according to GP1 to give 6.8 mg of the title compound (160FE58E6). MS (ESI) 293 (MH$^+$). Purity for MH$^+$ (UV/MS) 100/100.

Example 22

2-Methyl-1-(piperazin-1-yl)-8-trifluoromethyl-5H-dibenzo[b,e][1,4]diazepine (160FE58E7)

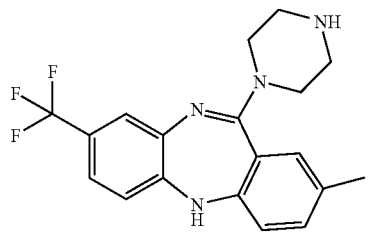

4-Fluoro-3-nitrobenzotrifluoride (314 mg, 1.5 mmol) and 2-amino-5-methylbenzoic acid (76 mg, 0.5 mmol) were reacted according to GP1 to give 1.2 mg of the title compound (160FE58E7). MS (ESI) 361 (MH$^+$). Purity for MH$^+$ (UV/MS) 100/85.

Example 23

8-Chloro-4-methyl-11-(piperazin-1-yl)-5H-dibenzo[b,e][1,4]diazepine (160FE74C)

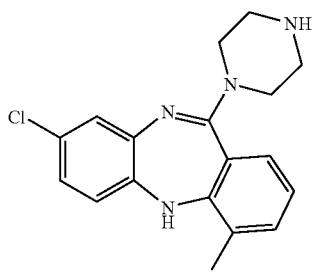

5-Chloro-2-fluoronitrobenzene (1.06 g, 6.0 mmol) and 2-amino-3-methylbenzoic acid (302 mg, 2.0 mmol) were reacted according to GP1 to give 4.8 mg of the title compound (160FE74C). MS (ESI) 327 (MH$^+$). Purity for MH$^+$ (UV/MS) 97/90.

Example 24

1,8-Dichloro-11-(piperazin-1-yl)-5H-dibenzo[b,e][1,4]diazepine (203FE03)

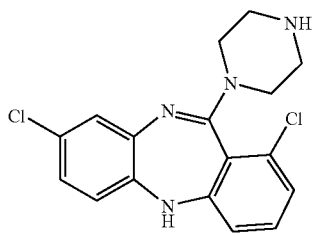

5-Chloro-2-fluoronitrobenzene (1.06 g, 6.0 mmol) and 2-amino-6-chlorobenzoic acid (343 mg, 2.0 mmol) were reacted according to GP1 to give 3.1 mg of the title compound (203FE03). MS (ESI) 347 (MH$^+$). Purity for MH$^+$ (UV/MS) 100/99.

Example 25

8-Bromo-5-methyl-11-(piperazin-1-yl)-5H-dibenzo[b,e][1,4]diazepine (166JO32)

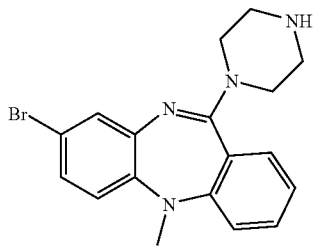

5-Bromo-2-fluoronitrobenzene (580 mg, 2.6 mmol) and N-methylantranilic acid (200 mg, 1.3 mmol) were reacted according to GP1 to give 1.6 mg of the title compound (166JO32). MS (ESI) 371 (MH$^+$). Purity for MH$^+$ (UV/MS) 90/74.

Example 26

General Procedure 2 (GP2)

A mixture of an aminobenzoic acid (1 eq.), a 2-fluoronitrobenzene (3 eq.) or a 2-chloronitrobenzene (3 eq.), and Cs$_2$CO$_3$ (3 eq.) in DMF was heated to 140° C. for 1 hour, and then allowed to obtain room temperature. The mixture was diluted with water and washed with EtOAc (2×).

EtOH and Na$_2$S$_2$O$_4$ (5 eq.) was added to the aqueous phase and the resulting mixture was stirred for 1 h. Aqueous HCl (2 M) was added to the mixture and then the aqueous phase was extracted with EtOAc (3×) and the combined organic phases were concentrated.

The residue was taken up in xylene and the resulting mixture was stirred at 130° C. over night. The mixture was diluted with EtOAc, washed with saturated aqueous NaHCO$_3$-solution, dried (Na$_2$SO$_4$), and concentrated.

The residue was taken up in dioxane and added to a mixture of TiCl$_4$ (1.1 eq., 1 M in toluene) and piperazine (5 eq.) in dioxane at 50° C. The resulting mixture was stirred at 100° C. over night, and then allowed to obtain room temperature. Aqueous HCl (2 M) was added to the mixture until solution became acidic and then the aqueous phase was extracted with EtOAc (2×). Aqueous NaOH (2 M) was added to the aqueous phase until a basic solution was obtained and the resulting suspension was extracted with EtOAc (3×). The combined organic phases were concentrated and purified by HPLC.

Example 27

7,8-Dichloro-11-(piperazin-1-yl)-5H-dibenzo[b,e][1,4]diazepine (166JO28)

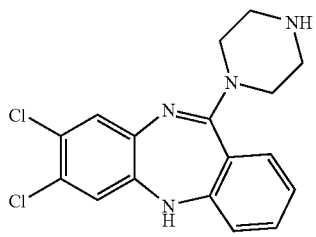

1,2-Dichloro-4-fluoro-5-nitrobenzene (1.26 g, 6.0 mmol) and 2-aminobenzoic acid (274 mg, 2 mmol) were reacted according to GP2 to give 16 mg of the title compound (166JO28). MS (ESI) 347 (MH$^+$). Purity for MH$^+$ (UV/MS) 99/96.

Example 28

11-(Piperazin-1-yl)-8-trifluoromethyl-5H-dibenzo[b,e][1,4]diazepine (166JO23)

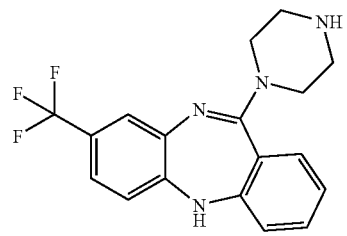

4-Fluoro-3-nitrobenzotrifluoride (1.25 g, 6 mmol) and 2-aminobenzoic acid (274 mg, 2 mmol) were reacted according to GP2 to give 12 mg of the title compound (166JO23). MS (ESI) 347 (MH$^+$). Purity for MH$^+$ (UV/MS) 81/98.

Example 29

11-(Piperazin-1-yl)-5H-dibenzo[b,e][1,4]diazepine (160FE19A)

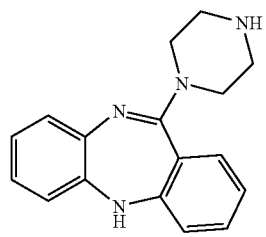

2-Fluoro-nitrobenzene (847 mg, 6.0 mmol) and 2-aminobenzoic acid (274 mg, 2 mmol) were reacted according to GP2 to give 16 mg of the title compound (160FE19A). MS (ESI) 279 (MH$^+$). Purity for MH$^+$ (UV/MS) 100/100.

Example 30

8-Fluoro-11-(piperazin-1-yl)-5H-dibenzo[b,e][1,4]diazepine (160FE19C)

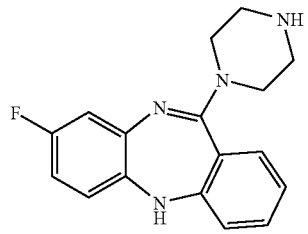

2,5-Difluoronitrobenzene (955 mg, 6.0 mmol) and 2-aminobenzoic acid (274 mg, 2 mmol) were reacted according to GP2 to give 8.9 mg of the title compound (160FE19C). MS (ESI) 297 (MH⁺). Purity for MH⁺ (UV/MS) 99/97.

Example 31

11-(Piperazin-1-yl)-5H-dibenzo[b,e][1,4]diazepine-8-carbonitrile (160FE19D)

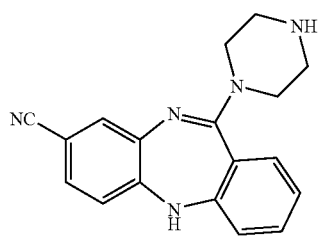

4-Chloro-3-nitrobenzonitrile (1.10 g, 6.0 mmol) and 2-aminobenzoic acid (274 mg, 2 mmol) were reacted according to GP2 to give 4.7 mg of the title compound (160FE19D). MS (ESI) 304 (MH⁺). Purity for MH⁺ (UV/MS) 100/86.

Example 32

8-Bromo-11-(piperazin-1-yl)-5H-dibenzo[b,e][1,4]diazepine (160FE19E)

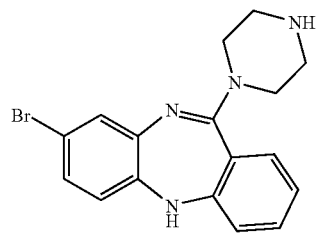

5-Bromo-2-fluoronitrobenzene (1.32 g, 6.0 mmol) and 2-aminobenzoic acid (274 mg, 2 mmol) were reacted according to GP2 to give 15 mg of the title compound (160FE19E). MS (ESI) 357 (MH⁺). Purity for MH⁺ (UV/MS) 100/100.

Example 33

8-Methyl-11-(piperazin-1-yl)-5H-dibenzo[b,e][1,4]diazepine (160FE19F)

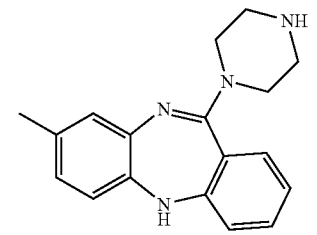

4-Chloro-3-nitrotoluene (1.03 g, 6.0 mmol) and 2-aminobenzoic acid (274 mg, 2 mmol) were reacted according to GP2 to give 1.6 mg of the title compound (160FE19F). MS (ESI) 293 (MH⁺). Purity for MH⁺ (UV/MS) 70/70.

Example 34

General Procedure 3 (GP3)

1-chloroethyl chloroformate (17 mg, 0.12 mmol) at 10° C. was added to a N-methyl piperazine derivative (0.1 mmol) dissolved in THF (2 ml). The resulting mixture was then heated at reflux for 18 h. The temperature was decreased and the THF removed at reduced pressure. Methanol was then added to the remaining oil and the mixture was shaken at 65° C. for 2 h. The methanol was removed at reduced pressure and the remaining crude product was purified by HPLC.

Example 35

3-Fluoro-6-piperazin-1-yl-11H-dibenzo[b,e]azepine (160FE02)

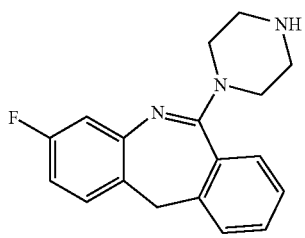

3-Fluoro-6-(4-methyl-piperazin-1-yl)-11H-dibenzo[b,e]azepine (31 mg, 0.1 mmol) was reacted according to GP3 to give 8 mg of the title compound isolated as oxalate salt (160FE02). MS (ESI) 296 (MH⁺). Purity for MH⁺ (UV/MS) 99/100.

Example 36

2-(Trifluoromethanesulfonyloxy)-11-(piperazin-1-yl)-5H-dibenzo[b,e][1,4]diazepine (160FE13A)

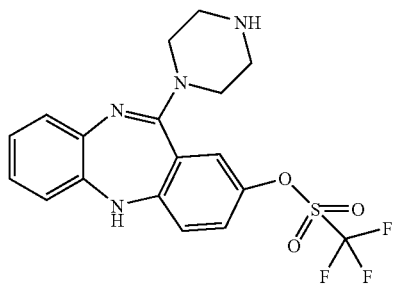

2-(Trifluoromethanesulfonyloxy)-11-(4-methyl-piperazin-1-yl)-5H-dibenzo[b,e][1,4]diazepine (39 mg, 0.1 mmol) was reacted according to GP3 to give 3.0 mg of the title compound (160FE13A). MS (ESI) 427 (MH⁺). Purity for MH⁺ (UV/MS) 95/98.

Example 37

2-(Trifluoromethanesulfonyloxy)-11-(piperazin-1-yl)-5H-dibenzo[b,e][1,4]oxazepine (160FE13B)

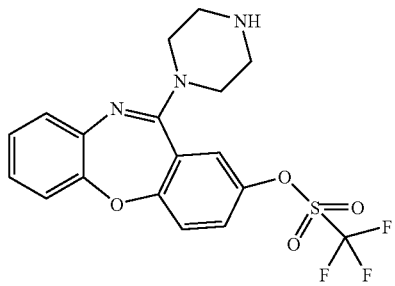

2-(Trifluoromethanesulfonyloxy)-11-(4-methyl-piperazin-1-yl)-5H-dibenzo[b,e][1,4]oxazepine (39 mg, 0.1 mmol) was reacted according to GP3 to give 11 mg of the title compound (160FE13B). MS (ESI) 428 (MH$^+$). Purity for MH$^+$ (UV/MS) 98/100.

Example 38

8-Chloro-2-(trifluoromethanesulfonyloxy)-11-(piperazin-1-yl)-5H-dibenzo[b,e][1,4]diazepine (160FE13C)

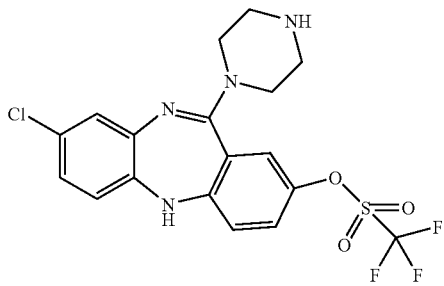

8-Chloro-2-(trifluoromethanesulfonyloxy)-11-(4-methyl-piperazin-1-yl)-5H-dibenzo[b,e][1,4]diazepine (42 mg, 0.1 mmol) was reacted according to GP3 to give 3.2 mg of the title compound (160FE13C). MS (ESI) 461 (MH$^+$). Purity for MH$^+$ (UV/MS) 100/100.

Example 39

8-(Trifluoromethanesulfonyloxy)-11-(piperazin-1-yl)-5H-dibenzo[b,e][1,4]diazepine (160FE13D)

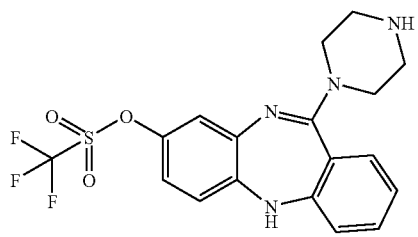

8-(Trifluoromethanesulfonyloxy)-11-(4-methyl-piperazin-1-yl)-5H-dibenzo[b,e][1,4]diazepine (39 mg, 0.1 mmol) was reacted according to GP3 to give 2.2 mg of the title compound (160FE13D). MS (ESI) 427 (MH$^+$). Purity for MH$^+$ (UV/MS) 100/100.

Example 40

General Procedure 4 (GP4)

A mixture of appropriate lactam (0.1 mmol) in dioxane was added to a mixture of TiCl$_4$ (1.1 eq., 1 M in toluene) and the amine (0.5 mmol) in dioxane at 50° C. or to a mixture of TiCl$_4$ (2.2 eq., 1 M in toluene) and the amine (1.0 mmol) in dioxane at 50° C. The resulting mixture was stirred at 100° C. over night, and then allowed to obtain room temperature. Aqueous HCl (3 mL, 2 M) was added to the aqueous mixture and then the aqueous phase was extracted with EtOAc (2×4 mL). Aqueous NaOH (6 mL, 2 M) was added to the aqueous phase and the resulting suspension was extracted with EtOAc (3×3 mL). The combined organic phases were concentrated and purified by HPLC.

Example 41

11-(Piperazin-1-yl)-dibenzo[b,f][1,4]thiazepin (160FE17A)

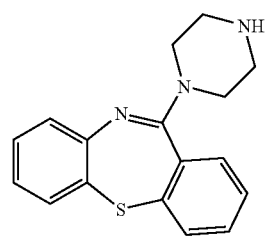

10H-Dibenzo[b,f][1,4]thiazepin-11-one (23 mg, 0.1 mmol) and piperazine (43 mg, 0.5 mmol) were reacted according to GP4 to give 3.1 mg of the title compound (160FE17A). MS (ESI) 296 (MH$^+$). Purity for MH$^+$ (UV/MS) 97/90.

Example 42

11-(Piperazin-1-yl)-2,3-dihydro-1,4-benzodioxino[6,7-b][1,4]benzothiazepin (160FE17B)

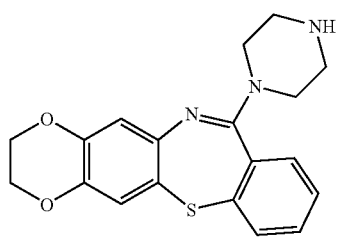

2,3-Dihydro-1,4-benzodioxino[6,7-b][1,4]benzothiazepin-11(12H)-one (29 mg, 0.1 mmol) and piperazine (43 mg, 0.5 mmol) were reacted according to GP4 to give 1.9 mg of the title compound (160FE17B). MS (ESI) 354 (MH$^+$). Purity for MH$^+$ (UV/MS) 99/95.

Example 43

8-Chloro-11-[1,4]diazepam-1-yl-5H-dibenzo[b,e][1,4]diazepine (160FE16A)

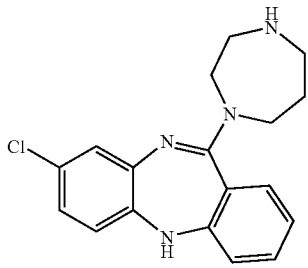

8-Chloro-5,10-dihydro-dibenzo[b,e][1,4]diazepine-11-one (25 mg, 0.1 mmol) and homopiperazine (50 mg, 0.5 mmol) were reacted according to GP4 to give 12 mg of the title compound (160FE16A). MS (ESI) 327 (MH$^+$). Purity for MH$^+$ (UV/MS) 99/93.

Example 44

N'-(8-Chloro-5H-dibenzo[b,e][1,4]diazepine-11-yl)-N,N-dimethyl-ethane-1,2-diamine (160FE16D)

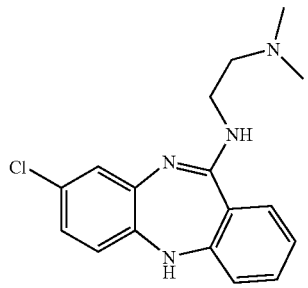

8-Chloro-5,10-dihydro-dibenzo[b,e][1,4]diazepine-11-one (25 mg, 0.1 mmol) and N,N-dimethylethylenediamine (44 mg, 0.5 mmol) were reacted according to GP4 to give 20 mg of the title compound (160FE16D). MS (ESI) 315 (MH$^+$). Purity for MH$^+$ (UV/MS) 100/100.

Example 45

N'-(8-Chloro-5H-dibenzo[b,e][1,4]diazepine-11-yl)-N,N-diethyl-ethane-1,2-diamine (160FE16E)

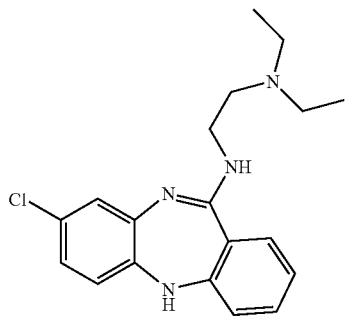

8-Chloro-5,10-dihydro-dibenzo[b,e][1,4]diazepine-11-one (25 mg, 0.1 mmol) and N,N-diethylethylenediamine (58 mg, 0.5 mmol) were reacted according to GP4 to give 3.9 mg of the title compound (160FE16E). MS (ESI) 343 (MH$^+$). Purity for MH$^+$ (UV/MS) 99/94.

Example 46

8-Chloro-11-(4-methyl-[1,4]diazepam-1-yl)-5H-dibenzo[b,e][1,4]diazepine (160FE16F)

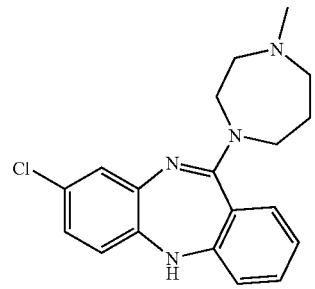

8-Chloro-5,10-dihydro-dibenzo[b,e][1,4]diazepine-11-one (25 mg, 0.1 mmol) and 1-methylhomopiperazine (57 mg, 0.5 mmol) were reacted according to GP4 to give 5.7 mg of the title compound (160FE16F). MS (ESI) 341 (MH$^+$). Purity for MH$^+$ (UV/MS) 100/100.

Example 47

8-Chloro-2-methoxy-11-(piperazin-1-yl)-5H-dibenzo[b,e][1,4]diazepine (160FE20A)

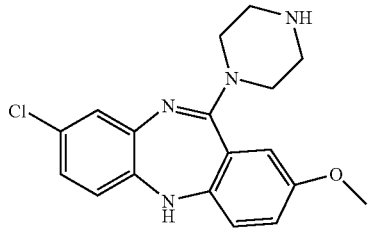

8-Chloro-2-methoxy-5,10-dihydro-dibenzo[b,e][1,4]diazepine-11-one (28 mg, 0.1 mmol) and piperazine (86 mg, 1.0 mmol) were reacted according to GP4 to give 19 mg of the title compound (160FE20A). MS (ESI) 342 (MH$^+$). Purity for MH$^+$ (UV/MS) 99/100.

Example 48

N'-(5H-Dibenzo[b,e][1,4]diazepine-11-yl)-N,N-dimethyl-ethane-1,2-diamine (160FE20B)

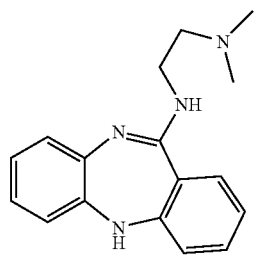

5,10-Dihydro-dibenzo[b,e][1,4]diazepine-11-one (160FE15A) (21 mg, 0.1 mmol) and N,N-dimethylethylenediamine (88 mg, 1.0 mmol) were reacted according to GP4 to give 7.6 mg of the title compound (160FE20B). MS (ESI) 281 (MH⁺). Purity for MH⁺ (UV/MS) 100/100.

Example 49

11-[1,4]Diazepam-1-yl-5H-dibenzo[b,e][1,4]diazepine (160FE20C)

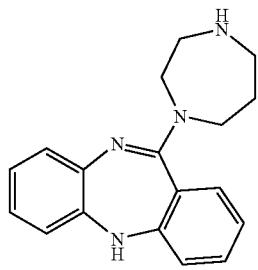

5,10-Dihydro-dibenzo[b,e][1,4]diazepine-11-one (160FE15A) (21 mg, 0.1 mmol) and homopiperazine (100 mg, 1.0 mmol) were reacted according to GP4 to give 12 mg of the title compound (160FE20C). MS (ESI) 293 (MH⁺). Purity for MH⁺ (UV/MS) 95/95.

Example 50

N'-(8-Fluoro-5H-dibenzo[b,e][1,4]diazepine-11-yl)-N,N-dimethyl-ethane-1,2-diamine (160FE20D)

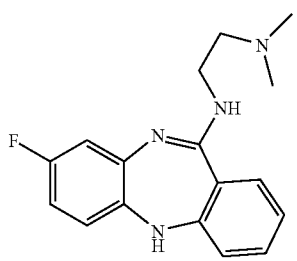

8-Fluoro-5,10-dihydro-dibenzo[b,e][1,4]diazepine-11-one (160FE15C) (23 mg, 0.1 mmol) and N,N-dimethylethylenediamine (88 mg, 1.0 mmol) were reacted according to GP4 to give 11 mg of the title compound (160FE20D). MS (ESI) 299 (MH⁺). Purity for MH⁺ (UV/MS) 100/100.

Example 51

8-Fluoro-11-[1,4]diazepam-1-yl-5H-dibenzo[b,e][1,4]diazepine (160FE16A)

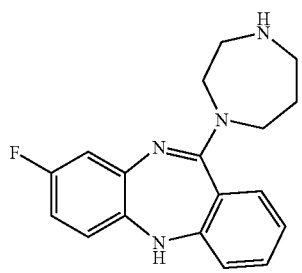

8-Fluoro-5,10-Dihydro-dibenzo[b,e][1,4]diazepine-11-one (160FE15C) (23 mg, 0.1 mmol) and homopiperazine (100 mg, 1.0 mmol) were reacted according to GP4 to give 19 mg of the title compound (160FE20E). MS (ESI) 311 (MH⁺). Purity for MH⁺ (UV/MS) 100/100.

Example 52

N'-(8-Chloro-5H-dibenzo[b,e][1,4]diazepine-11-yl)-N-methyl-ethane-1,2-diamine (160FE22)

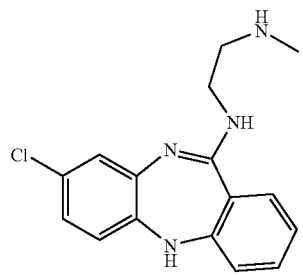

8-Chloro-5,10-dihydro-dibenzo[b,e][1,4]diazepine-11-one (25 mg, 0.1 mmol) and N-methylethylenediamine (74 mg, 1.0 mmol) were reacted according to GP4 to give 7.6 mg of the title compound (160FE22). MS (ESI) 301 (MH⁺). Purity for MH⁺ (UV/MS) 92/83.

Example 53

8-Chloro-11-(trans-2,5-dimethyl-piperazin-1-yl)-5H-dibenzo[b,e][1,4]diazepine (160FE33A)

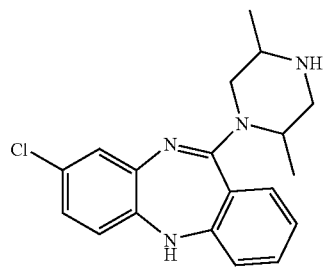

8-Chloro-5,10-dihydro-dibenzo[b,e][1,4]diazepine-11-one (25 mg, 0.1 mmol) and trans-2,5-dimethylpiperazine (114 mg, 1.0 mmol) were reacted according to GP4 to give 1.9 mg of the title compound (160FE33A). MS (ESI) 341 (MH⁺). Purity for MH⁺ (UV/MS) 100/82.

Example 54

8-Chloro-11-(3,5-dimethyl-piperazin-1-yl)-5H-dibenzo[b,e][1,4]diazepine (160FE33B)

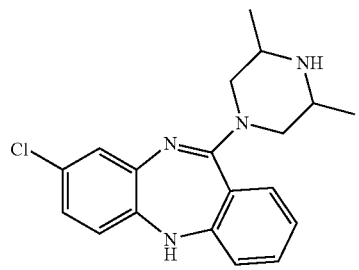

8-Chloro-5,10-dihydro-dibenzo[b,e][1,4]diazepine-11-one (25 mg, 0.1 mmol) and 2,6-dimethylpiperazine (114 mg, 1.0 mmol) were reacted according to GP4 to give 18 mg of the title compound (160FE33B). MS (ESI) 341 (MH⁺). Purity for MH⁺ (UV/MS) 100/100.

Example 55

8-Chloro-11-(3-methyl-piperazin-1-yl)-5H-dibenzo[b,e][1,4]diazepine (160FE38)

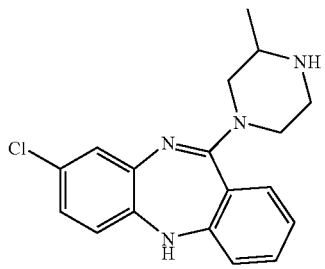

8-Chloro-5,10-dihydro-dibenzo[b,e][1,4]diazepine-11-one (25 mg, 0.1 mmol) and 2-methylpiperazine (100 mg, 1.0 mmol) were reacted according to GP4 to give 30 mg of the title compound (160FE38). MS (ESI) 327 (MH$^+$). Purity for MH$^+$ (UV/MS) 100/89.

Example 56

8-Chloro-11-(3-phenyl-piperazin-1-yl)-5H-dibenzo[b,e][1,4]diazepine (160FE45)

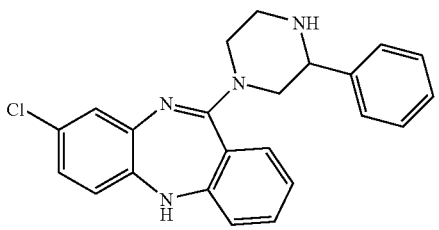

8-Chloro-5,10-dihydro-dibenzo[b,e][1,4]diazepine-11-one (25 mg, 0.1 mmol) and 2-phenylpiperazine (162 mg, 1.0 mmol) were reacted according to GP4 to give 27 mg of the title compound (160FE45). MS (ESI) 389 (MH$^+$). Purity for MH$^+$ (UV/MS) 100/89.

Example 57

8-Chloro-5-methyl-1-(piperazin-1-yl)-5H-dibenzo[b,e][1,4]diazepine (189JO25A)

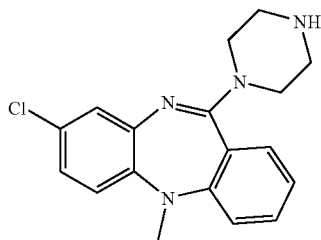

NaH (12 mg, 0.29 mmol, 60% in mineral oil) was added to a mixture of 8,5-dichloro-5H-dibenzo[b,e][1,4]diazepine (160FE64) (50 mg, 0.19 mmol) in toluene (1.5 mL) and DMF (0.5 mL). MeI (24 µL, 0.38 mmol) was then added. The resulting mixture was stirred for 1 h then quenched by addition of saturated aqueous NaHCO$_3$-solution (2 mL). The mixture was extracted with diethyl ether, and the combined organic phases were dried (Na$_2$SO$_4$) and concentrated. The residue was taken up in toluene (2.0 mL), piperazine (98 mg, 1.1 mmol) was added, and the resulting mixture was stirred at 100° C. for 1 h. Aqueous HCl (1 mL, 2M) and EtOAc (2 mL) was then added to the mixture. The phases were separated and the aqueous phase was extracted with EtOAc (2 mL) and then aqueous NaOH (2 mL, 2 M) was added. The basic aqueous phase was extracted with EtOAc (3×2 mL) and the combined organic phases were dried (Na$_2$SO$_4$) and concentrated. The residue was dissolved in DMF and purified on HPLC to give 34 mg of the title compound (189JO25A). MS (ESI) 327 (MH$^+$). Purity for MH$^+$ (UV/MS) 100/100.

Example 58

8-Chloro-5-benzyl-11-(piperazin-1-yl)-5H-dibenzo[b,e][1,4]diazepine (160FE46-PIPBN)

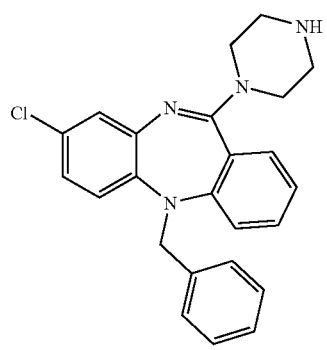

8,5-Dichloro-5H-dibenzo[b,e][1,4]diazepine (160FE46) (51 mg, 0.20 mmol) and benzyl bromide (68 mg, 0.4 mmol) were reacted as described for Example 57 to give 8.4 mg of the title compound (160FE46-PIPBN). MS (ESI) 403 (MH$^+$). Purity for MH$^+$ (UV/MS) 100/100.

Example 59

8-Iodo-11-(piperazin-1-yl)-5H-dibenzo[b,e][1,4]diazepine (166JO38)

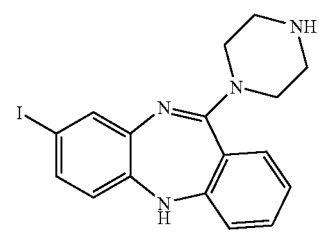

A mixture of 8-bromo-5,10-dihydro-dibenzo[b,e][1,4]diazepine-11-one (166JO31) (60 mg, 0.21 mmol), NaI, (62 mg, 0.42 mmol), N,N-dimethylethylenediamine (2.2 µL, 0.021 mmol) and CuI (2 mg, 0.01 mmol) in dioxane (1 ml) was heated in a capped tube for 3 days. The reaction mixture was allowed to obtain room temperature and then the mixture was applied onto a SCX-2 ion exchange column and the product was eluted with CH$_2$Cl$_2$ to give 49 mg of intermediate 8-iodolactam. The intermediate 8-iodolactam (20 mg, 0.060 mmol) in dioxane (1 mL) was added to a mixture of TiCl$_4$ (0.13 mL, 0.13 mmol, 1 M in toluene) and piperazine (0.051 g, 0.60 mmol) in dioxane at 50° C. The resulting mixture was stirred at 100° C. over night then allowed to obtain room temperature. Aqueous HCl (3 mL, 2 M) was added to the mixture and then the aqueous phase was extracted with EtOAc (2×4 mL). Aqueous NaOH (6 mL, 2 M) was added to the aqueous phase and the resulting suspension was extracted with EtOAc (3×3 mL). The combined organic phases were concentrated and purified by HPLC to give 4.1 mg of the title compound (166JO38). MS (ESI) 405 (MH$^+$). Purity for MH$^+$ (UV/MS) 100/100.

Example 60

2-Iodo-8-chloro-11-(piperazin-1-yl)-5H-dibenzo[b,e][1,4]diazepine (166JO54)

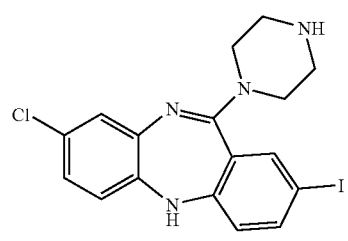

2-Bromo-8-chloro-5,10-dihydro-dibenzo[b,e][1,4]diazepine-11-one (intermediate from GP1) (30 mg, 0.09 mmol) was reacted as described for Example 59 to give 7.0 mg of the title compound (166JO54). MS (ESI) 439 (MH$^+$). Purity for MH$^+$ (UV/MS) 100/100.

Example 61

8-Phenyl-11-(piperazin-1-yl)-5H-dibenzo[b,e][1,4]diazepine (189JO53)

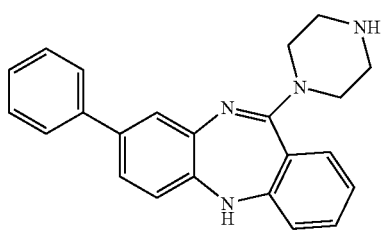

Tetrakis(triphenylphosphine)palladium(0) (catalytic amount) was added to a mixture of 8-bromo-5,10-dihydro-dibenzo[b,e][1,4]diazepine-11-one (166JO31) (30 mg, 0.12 mmol), benzene boronic acid (18 mg, 0.15 mmol) and K$_2$CO$_3$ (34 mg, 0.24 mmol) in deoxygenised toluene/EtOH/H$_2$O (1.5 mL) and the resulting mixture was stirred at 80° C. over night. The mixture was diluted with EtOAc, washed with saturated aqueous NaHCO$_3$-solution, dried (Na$_2$SO$_4$) and concentrated to give crude 8-phenyl lactam. The intermediate 8-phenyl lactam in dioxane (1 mL) was added to a mixture of TiCl$_4$ (0.24 mL, 0.24 mmol, 1 M in toluene) and piperazine (0.103 g, 1.2 mmol) in dioxane at 50° C. The resulting mixture was stirred at 100° C. over night, and then allowed to obtain room temperature. Aqueous HCl (3 mL, 2 M) was added to the mixture and then the aqueous phase was extracted with EtOAc (2×4 mL). Aqueous NaOH (6 mL, 2 M) was added to the aqueous phase and the resulting suspension was extracted with EtOAc (3×3 mL). The combined organic phases were applied onto a SCX-2 ion exchange column. The column was washed with MeOH, and then the product was eluted with NH$_3$ (7 N in MeOH), concentrated, and purified by HPLC to give 16 mg of the title compound (189JO53). MS (ESI) 355 (MH$^+$). Purity for MH$^+$ (UV/MS) 100/100.

Example 62

8-Chloro-11-(piperidin-1-yl)-5H-dibenzo[b,e][1,4]diazepine (166JO69A)

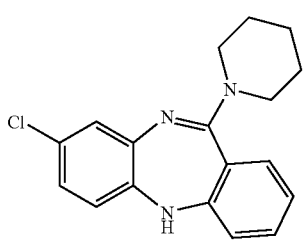

Piperidine (37 mg, 0.44 mmol) was added to crude 8-chloro-11-methylsulfanyl-5H-dibenzo[b,e][1,4]diazepine (166JO50) (90 mg, purity 50%, 0.218 mmol) in pyridine (2 mL) and the resulting mixture was heated in a capped tube at 160° C. for 10 h. The mixture was concentrated and flash chromatographed (SiO$_2$, heptane:EtOAc 8:1-6:1) to give 12 mg of the title compound (166JO69A). MS (ESI) 312 (MH$^+$). Purity for MH$^+$ (UV/MS) 100/100.

Example 63

8-Chloro-11-(morpholin-4-yl)-5H-dibenzo[b,e][1,4]diazepine (166JO69B)

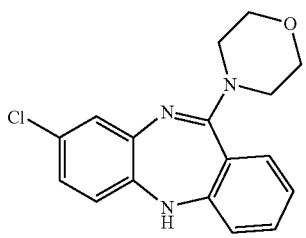

Crude 8-chloro-11-methylsulfanyl-5H-dibenzo[b,e][1,4]diazepine (166JO50) (90 mg, purity 50%, 0.218 mmol) and morpholine (38 mg, 0.44 mmol) were reacted as described for Example 62 to give 11 mg of the title compound (166JO69B). MS (ESI) 314 (MH$^+$). Purity for MH$^+$ (UV/MS) 100/98.

Example 64

5-Allyl-8-chloro-11-(piperazin-1-yl)-5H-dibenzo[b,e][1,4]diazepine (166JO68)

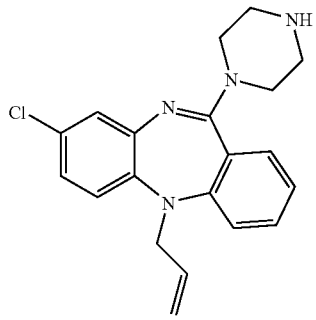

K'OBu (343 mg, 3.1 mmol) was added to a mixture of 8-chloro-5,10-dihydro-dibenzo[b,e][1,4]diazepine-11-one (500 mg, 2.0 mmol) in dioxane (10 mL) and the resulting mixture was stirred at 60° C. for 1 h, then cooled to room temperature. p-Methoxybenzyl chloride (0.42 mL, 3.1 mmol) was added and the resulting mixture was stirred at 40° C. for 2 h. The reaction was quenched by addition of MeOH (2 mL). The mixture was diluted with $CH_2Cl_2$, washed with saturated aqueous $NaHCO_3$-solution, dried ($Na_2SO_4$), concentrated and flash chromatographed ($SiO_2$, heptane:EtOAc, 4:1-3:1) which gave intermediate p-methoxybenzylprotected lactam (732 mg), 85% pure, which was used in the next step without further purification.

To a mixture of p-methoxybenzylprotected lactam (100 mg, 0.27 mmol) in DMF (2 mL) was added NaH (16 mg, 0.41 mmol, 60% in mineral oil) and the resulting mixture was heated to 60° C. then allowed to obtain room temperature. Allyl bromide (36 µL, 0.41 mmol) was added and the resulting mixture was stirred at room temperature for 3 h then diluted with $CH_2Cl_2$, washed with saturated aqueous $NaHCO_3$-solution, dried ($Na_2SO_4$), concentrated, flash chromatographed ($SiO_2$, heptane:EtOAc 8:1-4:1), and concentrated. The residue was taken up in trifluoroacetic acid (4 mL) and the resulting mixture was stirred at room temperature over night, then at 45° C. for 2 h. The mixture was concentrated, chromatographed ($SiO_2$, heptane:EtOAc 8:1-4:1), and concentrated. The residue was taken up in toluene (2 mL) and N,N-dimethylaniline (48 µL, 0.38 mmol) and $POCl_3$ (35 µL, 0.38 mmol) were added. The resulting mixture was stirred at 100° C. for 2 h then concentrated. The residue was taken up in dioxane, piperazine (65 mg, 0.76 mmol) was added and the resulting mixture was stirred at 100° C. for 3 h. To the mixture was added aqueous HCl (3 mL, 2 M) and then the aqueous phase was extracted with EtOAc (2×4 mL). To the aqueous phase was added aqueous NaOH (6 mL, 2 M) and the resulting suspension was extracted with EtOAc (3×3 mL). The combined organic phases were concentrated and purified by HPLC to give 17 mg of the title compound (166JO68). MS (ESI) 353 ($MH^+$). Purity for $MH^+$ (UV/MS) 99/88.

Example 65

6-Chloro-11-(piperazin-1-yl)-5H-dibenzo[b,e][1,4]diazepine (189JO68)

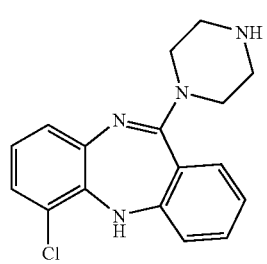

A mixture of a methyl 2-aminobenzoate (454 mg, 3.0 mmol), 3-chloro-2-fluoronitrobenzene (352 mg, 2 mmol) and $Cs_2CO_3$ (0.78 g, 2.4 mol) in DMF (4 mL) was stirred at 140° C. for 2 h.

The mixture was diluted with EtOAc (10 mL) and washed with 2 M aqueous NaOH-solution (2×5 mL), dried ($Na_2SO_4$), concentrated and flash chromatographed ($SiO_2$, toluene:heptane:EtOAc-system) and concentrated. The residue was taken up in THF (10 mL), 1 M aqueous LiOH (5 mL) was added and the resulting mixture was stirred at 80° C. for 1 h, and then allowed to obtain room temperature. 2 M aqueous HCl was added until pH 2. The aqueous phase was extracted with EtOAc (3×). The combined organic phases were dried ($Na_2SO_4$) and concentrated. The residue was taken up in EtOH and a mixture of $K_2CO_3$ (1.38 g, 10 mmol) and $Na_2S_2O_4$ (1.74 g, 10 mmol) in water was added and the resulting mixture was stirred for 1 h. The mixture was diluted with water and washed with 1 M aqueous NaOH-solution (2×5 mL) and then dried ($Na_2SO_4$) and concentrated.

The residue was taken up in $CH_2Cl_2$ and 1-ethyl-3-(3-dimethylaminopropyl)carbodiimide hydrochloride (307 mg, 1.6 mmol) was added. The resulting mixture was stirred at room temperature for 1 h. The mixture was diluted with EtOAc, washed with saturated aqueous $NaHCO_3$-solution, dried ($Na_2SO_4$), concentrated, and flash chromatographed ($SiO_2$, heptane:EtOAc, 2:1) to give 21 mg of the intermediate lactam.

The intermediate lactam was taken up in dioxane and added to a mixture of $TiCl_4$ (0.19 mL, 0.19 mmol, 1 M in toluene) and piperazine (73 mg, 0.85 mmol) in dioxane at 50° C. The resulting mixture was stirred at 100° C. over night, and then allowed to obtain room temperature. To the mixture was added aqueous HCl (1 mL, 2 M) and then the aqueous phase was extracted with EtOAc (2×1 mL). To the aqueous phase was added aqueous NaOH (2 mL, 2 M) and the resulting suspension was extracted with EtOAc (3×1 mL). The combined organic phases were concentrated and purified by HPLC to give 9.8 mg of the title compound (189JO68) MS (ESI) 313 ($MH^+$). Purity for $MH^+$ (UV/MS) 100/98.

Example 66

8-Chloro-5-piperazin-1-yl-11H-benzo[b]pyrido[2,3-e][1,4]diazepine (166JO63)

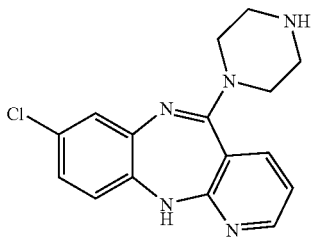

To a mixture of 5-chloro-2-nitroaniline (345 mg, 2 mmol) and pyridine (162 µL, 2 mmol) in dioxane was added 2-chloronicotinyl chloride (352 mg, 2 mmol) and the resulting mixture was stirred at room temperature for 2 h. The mixture was diluted with $CH_2Cl_2$, washed with saturated aqueous $NaHCO_3$-solution, dried ($Na_2SO_4$), concentrated and crystallised from MeOH to give 271 mg of intermediate diarylamine. To a mixture of intermediate diarylamine (100 mg, 0.32 mmol) in EtOH (0.5 mL) was added a mixture of $K_2CO_3$ (220 mg, 1.6 mmol) and $Na_2S_2O_4$ (278 mg, 1.6 mmol) in water (0.5 mL) and the resulting mixture was stirred for 1 h at room temperature. The mixture was concentrated and the residue taken up in EtOAc/$H_2O$ and separated. The organic phase was dried ($Na_2SO_4$) and concentrated. The residue was taken up in xylene and heated to 130° C. over night, then diluted with EtOAc, washed with saturated aqueous $NaHCO_3$-solution, dried ($Na_2SO_4$), concentrated and flash chromatographed ($SiO_2$, heptane:EtOAc) to give intermediate lactam. The intermediate lactam was taken up in dioxane and added to a mixture of $TiCl_4$ (187 µL, 0.187 mmol, 1 M in toluene) and piperazine (73 mg, 0.85 mmol) in dioxane at 50° C. The resulting mixture was stirred at 100° C. over night, and then allowed to obtain room temperature. To the mixture was added aqueous HCl (1 mL, 2 M) and then the aqueous phase was extracted with EtOAc (2×2 mL). To the aqueous phase was added aqueous NaOH (2 mL, 2 M) and the resulting suspension was extracted with EtOAc (3×1 mL). The combined organic phases were concentrated and purified by HPLC to give 20 mg of the title compound (166JO63). MS (ESI) 314 (MH$^+$). Purity for MH$^+$ (UV/MS) 100/99.

Example 67

2-Chloro-10-piperazin-1-yl-5H-dibenzo[b,f]azepin (189JO39)

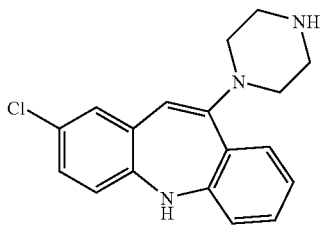

To a mixture under Ar of 2-chloro-5-(4-methoxybenzyl)-5,11-dihydrodibenzo[b,f]azepin-11-one (189JO27) (150 mg, 0.41 mmol) in $CH_2Cl_2$ (10 mL) at −75° C. was added $TiCl_4$ (0.60 mL, 0.60 mmol, 1 M in toluene) and the resulting mixture was stirred for 1 h. The mixture was diluted with saturated aqueous $NH_4Cl$-solution and $CH_2Cl_2$ and the mixture was allowed to obtain room temperature and the phases were separated. The aqueous phase was extracted with $CH_2Cl_2$ (1×10 mL) and the combined organic phases were dried ($Na_2SO_4$) and concentrated to give crude protected product (90 mg, 90%), that was used in the next step without further purification.

To a solution of $TiCl_4$ (0.18 mL, 0.18 mmol, 1 M in toluene) and piperazine (283 mg, 3.3 mmol) in dioxane (4 mL) at 50° was added crude protected product (80 mg, 0.33 mmol) and the resulting suspension was stirred at 100° C. for 1.5 h. The mixture was allowed to obtain room temperature, then it was diluted with EtOAc, washed with saturated aqueous $NaHCO_3$-solution, dried ($Na_2SO_4$), concentrated and flash chromatographed ($Al_2O_3$, $CH_2Cl_2$:MeOH, 1:0-25:1) to give 64 mg (63%) of the title compound (189JO39). MS (ESI) 312 (MH$^+$). Purity for MH$^+$ (UV/MS) 97/95.

Example 68

8-Chloro-11-(piperazin-1-yl)-dibenzo[b,f][1,4]thiazepine (189JO16)

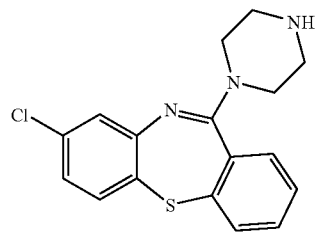

To a mixture of 8-chloro-10H-dibenzo[b,f][1,4]thiazepin-11-one (189JO13) (38 mg, 0.15 mmol) and N,N-dimethylaniline (46 µL, 0.36 mmol) in toluene was added $POCl_3$ (27 µL, 0.29 mmol) and the resulting mixture was stirred for 2 h at 100° C., and then concentrated. Toluene (2 mL) and piperazine (62 mg, 0.73 mmol) were added, and the resulting mixture was stirred at 100° C. for 3 h, and then allowed to obtain room temperature. To the mixture was added aqueous HCl (1 mL, 2 M) and then the aqueous phase was extracted with EtOAc (2×2 mL). To the aqueous phase was added aqueous NaOH (3 mL, 2 M) and the resulting mixture was extracted with EtOAc (3×3 mL). The combined organic phases were concentrated and purified by HPLC to give 6.6 mg of the title compound (189JO16). MS (ESI) 330 (MH$^+$). Purity for MH$^+$ (UV/MS) 99/98.

Example 68

8-Chloro-11-(piperazin-1-yl)-dibenzo[b,f][1,4]oxazepine (189JO31)

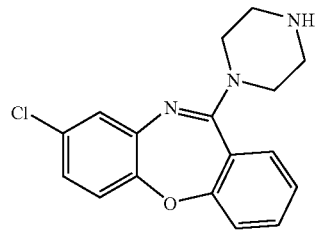

A mixture of 8-chloro-10H-dibenzo[b,f][1,4]oxazepin-11-one (189JO29C) (17 mg, 0.069 mmol) and 2,4-bis(4-methoxyphenyl)-1,3-dithia-2,4-diphosphetane-2,4-disulfide (16 mg, 0.040 mmol) in toluene (2 mL) was heated in capped tube using microwave assisted heating (130° C., 20 minutes). The reaction mixture was cooled to room temperature and MeI (18 µL, 0.29 mmol) was added and the resulting mixture was heated in capped tube using microwave assisted heating (120° C., 20 minutes). The mixture was concentrated and the residue was taken up in pyridine (2 mL) and piperazine (25 mg, 0.29 mmol) was added. The resulting mixture was heated in a capped tube at 130° C. over night then using microwave assisted heating (160° C., 30 minutes). The mixture was concentrated, diluted with EtOAc and washed with water. The organic phase was applied onto a SCX-2 ion exchange column. The column was washed with MeOH, and then the product was eluted with $NH_3$ (7 N in MeOH) to give 9.0 mg (57%) of the title compound (189JO31). MS (ESI) 314 ($MH^+$). Purity for $MH^+$ (UV/MS) 92/100.

Example 69

8-Chloro-11-(4-methyl-piperazin-1-yl)-dibenzo[b,f][1,4]oxazepine (189JO47)

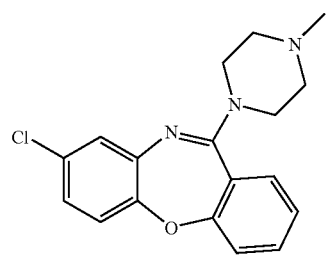

A mixture of 8-chloro-10H-dibenzo[b,f][1,4]oxazepin-11-one (189JO29C) (30 mg, 0.069 mmol) and 2,4-bis(4-methoxyphenyl)-1,3-dithia-2,4-diphosphetane-2,4-disulfide (29 mg, 0.040 mmol) in toluene (2 mL) was heated in a capped tube using microwave assisted heating (130° C., 20 minutes). The reaction mixture was cooled to room temperature and MeI (38 µL, 0.29 mmol) was added and the resulting mixture was heated in capped tube using microwave assisted heating (120° C., 20 minutes). The mixture was concentrated and the residue was taken up in pyridine (2 mL) and piperazine (24 mg, 0.29 mmol) was added. The resulting mixture was heated in a capped tube at 130° C. over night then heated using microwave assisted heating (160° C., 30 minutes). The mixture was concentrated, diluted with EtOAc and washed with water. The organic phase was dried ($Na_2SO_4$), concentrated and flash chromatographed ($SiO_2$, toluene:EtOAc:MeOH, 4:2:0-2:2:1) to give 8.9 mg of the title compound (189JO47). MS (ESI) 328 ($MH^+$). Purity for $MH^+$ (UV/MS) 98/93.

Example 70

3-Chloro-6-piperazin-1-yl-11H-dibenzo[b,e]azepine (1891060)

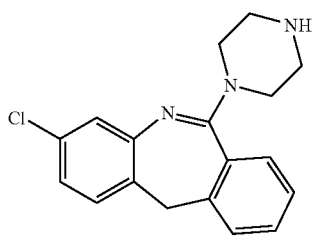

3-Chloro-5,11-dihydro-dibenzo[b,e]azepin-6-one (189JO59) (25 mg, 0.1 mmol) and piperazine were reacted according to GP4 to give 2.2 mg of the title compound (189JO60). MS (ESI) 312 ($MH^+$). Purity for $MH^+$ (UV/MS) 100/100.

Example 71

General Procedure 5 (GP5)

A mixture of a methyl aminobenzoic ester (2.0 mmol), a 2-fluoronitrobenzene (1.0 mmol) and $Cs_2CO_3$ (0.65 g, 2.0 mmol) in DMF (4mL) was stirred at 40° C. for 2 h. The mixture was diluted with EtOAc (10 mL) and washed with 2 M aqueous NaOH-solution (2×5 mL).

EtOH, $H_2O$, $K_2CO_3$ (0.69 g, 5 mmol) and $Na_2S_2O_4$ (0.87 g, 5 mmol) was added to the EtOAc-phase and the resulting mixture was stirred vigorously for 1 h. The aqueous phase was removed and the organic phase was washed with 1 M aqueous NaOH-solution (2×5 mL) and then concentrated.

The residue was taken up in DMF (1 mL), toluene (4 mL) and NaH (60 mg, 1.5 mmol, 60% in mineral oil) was added and the resulting mixture was stirred at 80° C. over night, then quenched by addition of saturated aqueous $NH_4Cl$-solution. The resulting mixture was diluted with EtOAc, washed with 2 M aqueous NaOH-solution (2×5 mL), dried ($Na_2SO_4$) and concentrated. The residue was taken up in dioxane and added to a mixture of $TiCl_4$ (1.1 mL, 1.1 mmol, 1 M in toluene) and piperazine (0.41 g, 5 mmol) in dioxane at 50° C. The resulting mixture was stirred at 100° C. over night, and then allowed to obtain room temperature. To the mixture was added aqueous HCl (3 mL, 2 M) and then the aqueous phase was extracted with EtOAc (2×4 mL). To the aqueous phase was added aqueous NaOH (6 mL, 2 M) and the resulting suspension was extracted with EtOAc (3×3 mL). The combined organic phases were concentrated, dried ($Na_2SO_4$) and purified by HPLC.

Example 72

8-Bromo-11-(piperazin-1-yl)-dibenzo[b,f][1,4]ox-
azepine (189JO48A)

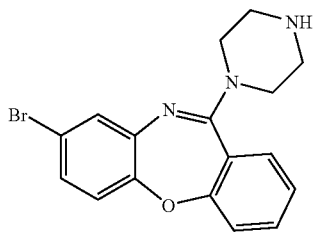

5-Bromo-2-fluoronitrobenzene (220 mg, 1 mmol) and methyl 2-hydroxybenzoate (304 mg, 2 mmol) were reacted according to GP5 to give 36 mg of the title compound (189JO48A). MS (ESI) 358 (MH$^+$). Purity for MH$^+$ (UV/MS) 96/82.

Example 73

11-(piperazin-1-yl)-dibenzo[b,f][1,4]oxazepine
(189JO48B)

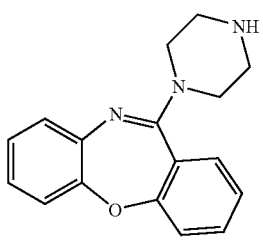

2-fluoronitrobenzene (141 mg, 1 mmol) and methyl 2-hydroxybenzoate (304 mg, 2 mmol) were reacted according to GP5 to give 5.2 mg of the title compound (189JO48B). MS (ESI) 280 (MH$^+$). Purity for MH$^+$ (UV/MS) 99/99.

Example 74

7-Chloro-11-(piperazin-1-yl)-dibenzo[b,f][1,4]ox-
azepine (189JO50A)

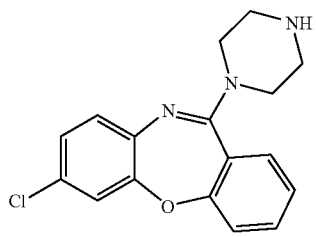

4-Chloro-2-fluoronitrobenzene (175 mg, 1 mmol) and methyl 2-hydroxybenzoate (304 mg, 2 mmol) were reacted according to GP5 to give 17 mg of the title compound (189JO50A). MS (ESI) 314 (MH$^+$). Purity for MH$^+$ (UV/MS) 100/100.

Example 75

8-Chloro-3-methoxy-11-(piperazin-1-yl)-dibenzo[b,
f][1,4]oxazepine (189JO50B)

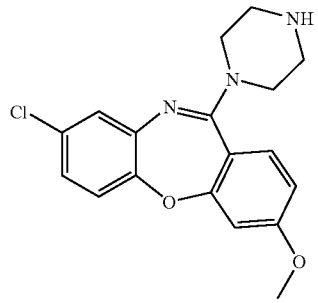

5-Chloro-2-fluoronitrobenzene (175 mg, 1 mmol) and methyl 2-hydroxy-4-methoxybenzoate (364 mg, 2 mmol) were reacted according to GP5 to give 6.8 mg of the title compound (189JO50B). MS (ESI) 344 (MH$^+$). Purity for MH$^+$ (UV/MS) 94/86.

Example 76

8-Bromo-3-methoxy-11-(piperazin-1-yl)-dibenzo[b,
f][1,4]oxazepine (189JO50D)

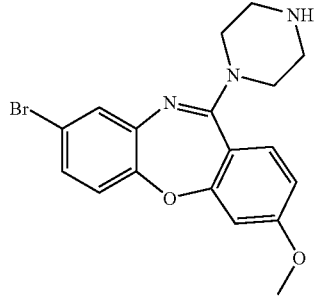

5-Bromo-2-fluoronitrobenzene (220 mg, 1 mmol) and methyl 2-hydroxy-4-methoxybenzoate (364 mg, 2 mmol) were reacted according to GP5 to give 14 mg of the title compound (189JO50D). MS (ESI) 388 (MH$^+$). Purity for MH$^+$ (UV/MS) 100/100.

Example 77

3-Methoxy-11-(piperazin-1-yl)-dibenzo[b,f][1,4]
oxazepine (189JO50E)

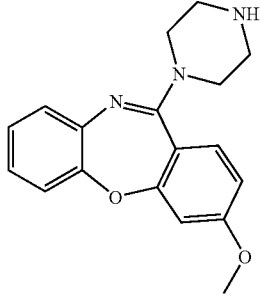

2-Fluoronitrobenzene (141 mg, 1 mmol) and methyl 2-hy-
droxy-4-methoxybenzoate (364 mg, 2 mmol) were reacted according to GP5 to give 33 mg of the title compound (189JO50E). MS (ESI) 310 (MH$^+$). Purity for MH$^+$ (UV/MS) 100/100.

Example 78

7-Chloro-3-methoxy-11-(piperazin-1-yl)-dibenzo[b,f][1,4]oxazepine (189JO50F)

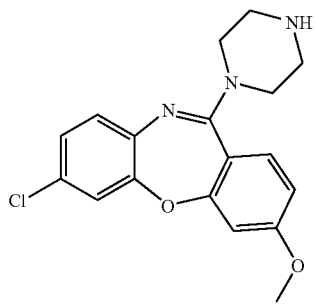

4-Chloro-2-fluoronitrobenzene (175 mg, 1 mmol) and methyl 2-hydroxy-4-methoxybenzoate (364 mg, 2 mmol) were reacted according to GP5 to give 6.7 mg of the title compound (189JO50F). MS (ESI) 344 (MH$^+$). Purity for MH$^+$ (UV/MS) 98/96.

Example 79

8-Chloro-4-methyl-11-(piperazin-1-yl)-dibenzo[b,f][1,4]oxazepine (189JO50H)

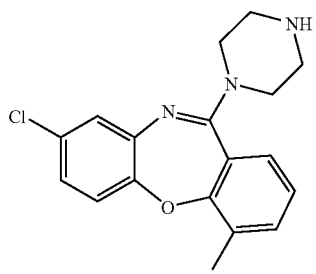

5-Chloro-2-fluoronitrobenzene (175 mg, 1 mmol) and methyl 2-hydroxy-3-methylbenzoate (332 mg, 2 mmol) were reacted according to GP5 to give 34 mg of the title compound (189JO50H). MS (ESI) 328 (MH$^+$). Purity for MH$^+$ (UV/MS) 100/100.

Example 80

8-Bromo-4-methyl-11-(piperazin-1-yl)-dibenzo[b,f][1,4]oxazepine (189JO51A)

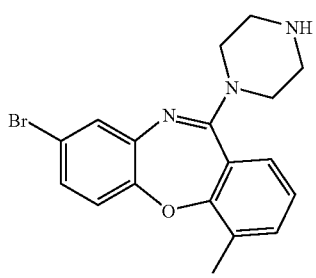

5-Bromo-2-fluoronitrobenzene (220 mg, 1 mmol) and methyl 2-hydroxy-3-methylbenzoate (332 mg, 2 mmol) were reacted according to GP5 to give 20 mg of the title compound (189JO51A). MS (ESI) 372 (MH$^+$). Purity for MH$^+$ (UV/MS) 100/100.

Example 81

4-Methyl-11-(piperazin-1-yl)-dibenzo[b,f][1,4]oxazepine (189JO51B)

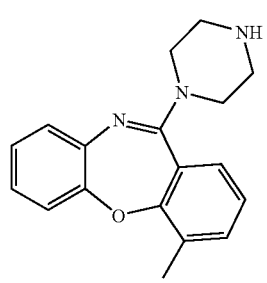

2-Fluoronitrobenzene (141 mg, 1 mmol) and methyl 2-hydroxy-3-methylbenzoate (332 mg, 2 mmol) were reacted according to GP5 to give 1.8 mg of the title compound (189JO51B). MS (ESI) 294 (MH$^+$). Purity for MH$^+$ (UV/MS) 99/98.

Example 82

2-Bromo-8-chloro-11-(piperazin-1-yl)-dibenzo[b,f][1,4]oxazepine (189JO51D)

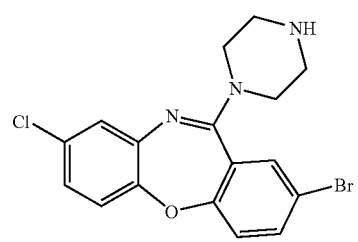

5-Chloro-2-fluoronitrobenzene (175 mg, 1 mmol) and methyl 5-bromo-2-hydroxybenzoate (462 mg, 2 mmol) were reacted according to GP5 to give 21 mg of the title compound (189JO51D). MS (ESI) 392 (MH$^+$). Purity for MH$^+$ (UV/MS) 100/100.

Example 83

2,8-Dibromo-11-(piperazin-1-yl)-dibenzo[b,f][1,4]oxazepine (189JO51E)

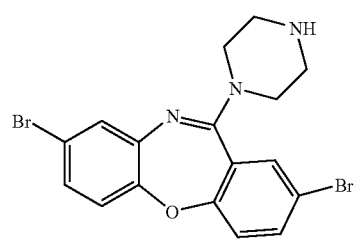

5-Bromo-2-fluoronitrobenzene (220 mg, 1 mmol) and methyl 5-bromo-2-hydroxybenzoate (462 mg, 2 mmol) were reacted according to GP5 to give 0.7 mg of the title compound (189JO51E). MS (ESI) 436 (MH$^+$). Purity for MH$^+$ (UV/MS) 94/99.

Example 84

2-Bromo-11-(piperazin-1-yl)-dibenzo[b,f][1,4]ox-azepine (189JO51F)

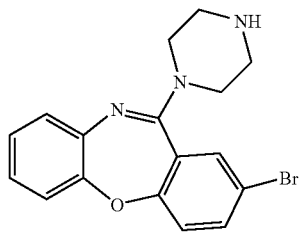

2-Fluoronitrobenzene (142 mg, 1 mmol) and methyl 5-bromo-2-hydroxybenzoate (462 mg, 2 mmol) were reacted according to GP5 to give 10 mg of the title compound (189JO51F). MS (ESI) 358 (MH$^+$). Purity for MH$^+$ (UV/MS) 95/99.

Example 85

2-Bromo-7-chloro-11-(piperazin-1-yl)-dibenzo[b,f][1,4]oxazepine (189JO51G)

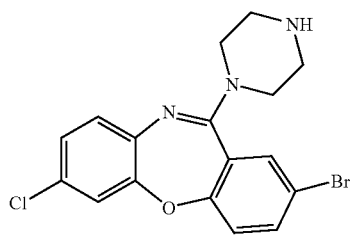

4-Chloro-2-fluoronitrobenzene (175 mg, 1 mmol) and methyl 5-bromo-2-hydroxybenzoate (462 mg, 2 mmol) were reacted according to GP5 to give 17 mg of the title compound (189JO51G). MS (ESI) 392 (MH$^+$). Purity for MH$^+$ (UV/MS) 100/100.

Example 86

11-(piperazin-1-yl)-8-trifluoromethyl-dibenzo[b,f][1,4]oxazepine (189JO54A)

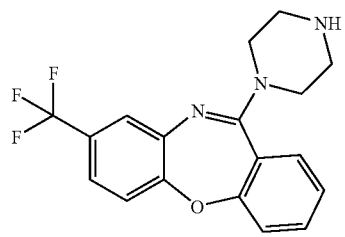

2-Fluoro-3-nitrobenzotrifluoride (209 mg, 1 mmol) and methyl 2-hydroxybenzoate (304 mg, 2 mmol) were reacted according to GP5 to give 19 mg of the title compound (189JO54A). MS (ESI) 348 (MH$^+$). Purity for MH$^+$ (UV/MS) 100/100.

Example 87

4-Methyl-1-(piperazin-1-yl)-8-trifluoromethyl-dibenzo[b,f][1,4]oxazepine (189JO54C)

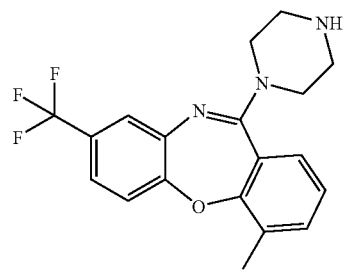

2-Fluoro-3-nitrobenzotrifluoride (209 mg, 1 mmol) and methyl 2-hydroxy-3-methylbenzoate (332 mg, 2 mmol) were reacted according to GP5 to give 15 mg of the title compound (189JO54C). MS (ESI) 362 (MH$^+$). Purity for MH$^+$ (UV/MS) 100/100.

Example 88

8-Fluoro-11-(piperazin-1-yl)-dibenzo[b,f][1,4]oxazepine (189JO54E)

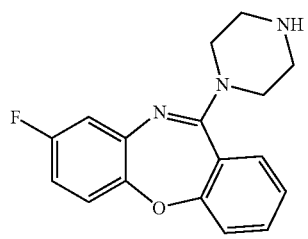

2,5-Difluoronitrobenzene (159 mg, 1 mmol) and methyl 2-hydroxybenzoate (304 mg, 2 mmol) were reacted according to GP5 to give 14 mg of the title compound (189JO54E). MS (ESI) 298 (MH$^+$). Purity for MH$^+$ (UV/MS) 100/100.

Example 89

8-Fluoro-3-methoxy-11-(piperazin-1-yl)-dibenzo[b,f][1,4]oxazepine (189JO54F)

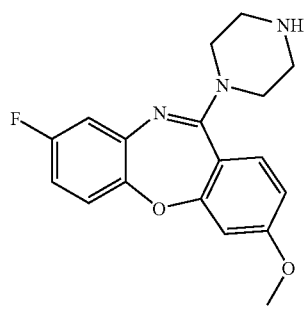

2,5-Difluoronitrobenzene (159 mg, 1 mmol) and methyl 2-hydroxy-4-methoxybenzoate (364 mg, 2 mmol) were reacted according to GP5 to give 9.8 mg of the title compound (189JO54F). MS (ESI) 328 (MH⁺). Purity for MH⁺ (UV/MS) 100/100.

Example 90

8-Fluoro-4-methyl-11-(piperazin-1-yl)-dibenzo[b,f][1,4]oxazepine (189JO54G)

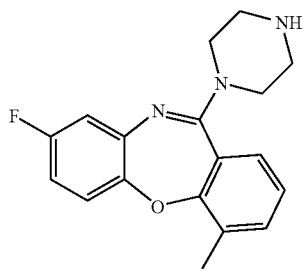

2,5-Difluoronitrobenzene (159 mg, 1 mmol) and 2-hydroxy-3-methylbenzoate (332 mg, 2 mmol) were reacted according to GP5 to give 9.8 mg of the title compound (189JO54G). MS (ESI) 312 (MH⁺). Purity for MH⁺ (UV/MS) 100/100.

Example 91

2-Bromo-8-fluoro-11-(piperazin-1-yl)-dibenzo[b,f][1,4]oxazepine (189JO54H)

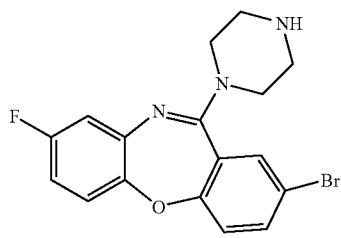

2,5-Difluoronitrobenzene (159 mg, 1 mmol) and methyl 5-bromo-2-hydroxybenzoate (462 mg, 2 mmol) were reacted according to GP5 to give 11 mg of the title compound (189JO54H). MS (ESI) 376 (MH⁺). Purity for MH⁺ (UV/MS) 100/100.

Example 92

8-Methyl-11-(piperazin-1-yl)-dibenzo[b,f][1,4]oxazepine (189JO58A)

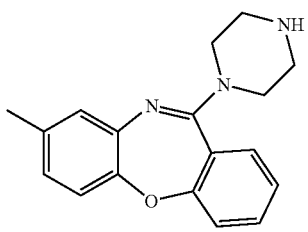

4-Fluoro-3-nitrotoluene (155 mg, 1 mmol) and methyl 2-hydroxybenzoate (304 mg, 2 mmol) were reacted according to GP5 to give 24 mg of the title compound (189JO58A). MS (ESI) 294 (MH⁺). Purity for MH⁺ (UV/MS) 100/98.

Example 93

3-Methoxy-8-methyl-11-(piperazin-1-yl)-dibenzo[b,f][1,4]oxazepine (189JO58B)

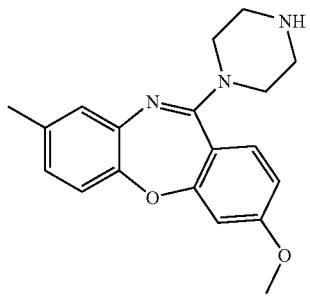

4-Fluoro-3-nitrotoluene (155 mg, 1 mmol) and methyl 2-hydroxy-4-methoxybenzoate (364 mg, 2 mmol) were reacted according to GP5 to give 27 mg of the title compound (189JO58B). MS (ESI) 324 (MH⁺). Purity for MH⁺ (UV/MS) 100/98.

Example 94

4,8-Dimethyl-11-(piperazin-1-yl)-dibenzo[b,f][1,4]oxazepine (189JO58C)

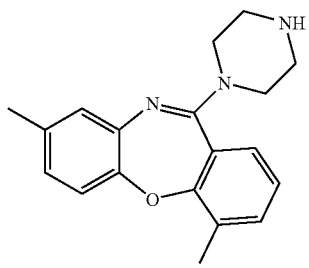

4-Fluoro-3-nitrotoluene (155 mg, 1 mmol) and methyl 2-hydroxy-3-methylbenzoate (332 mg, 2 mmol) were reacted according to GP5 to give 24 mg of the title compound (189JO58C). MS (ESI) 308 (MH⁺). Purity for MH⁺ (UV/MS) 100/98.

Example 95

3-Methoxy-11-(piperazin-1-yl)-8-trifluoromethyl-dibenzo[b,f][1,4]oxazepine (189JO62A)

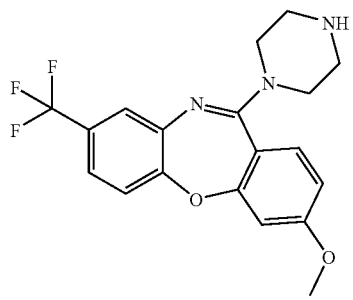

2-Fluoro-3-nitrobenzotrifluoride (209 mg, 1 mmol) and methyl 2-hydroxy-4-methoxybenzoate (364 mg, 2 mmol)

were reacted according to GP5 to give 12 mg of the title compound (189JO62A). MS (ESI) 378 (MH$^+$). Purity for MH$^+$ (UV/MS) 100/95.

Example 96

2-Bromo-11-(piperazin-1-yl)-8-trifluoromethyl-dibenzo[b,f][1,4]oxazepine (189JO62B)

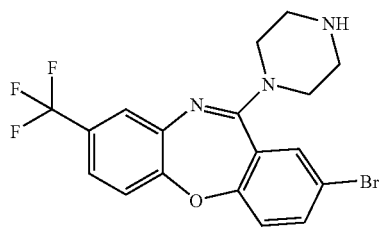

2-Fluoro-3-nitrobenzotrifluoride (209 mg, 1 mmol) and methyl 5-bromo-2-hydroxybenzoate (462 mg, 2 mmol) were reacted according to GP5 to give 11 mg of the title compound (189JO62B). MS (ESI) 426 (MH$^+$). Purity for MH$^+$ (UV/MS) 100/100.

Example 97

6-Chloro-11-(piperazin-1-yl)-dibenzo[b,f][1,4]oxazepine (189JO69)

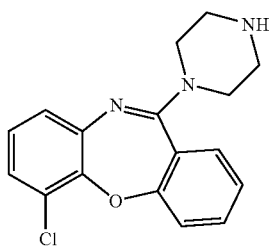

3-Chloro-2-fluoronitrobenzene (352 mg, 2 mmol) and methyl 2-hydroxybenzoate (453 mg, 3 mmol) were reacted according to GP5 to give 57 mg of the title compound (189JO69). MS (ESI) 314 (MH$^+$). Purity for MH$^+$ (UV/MS) 100/100.

Example 98

General Procedure 6 (GP6)

A mixture of a methyl aminobenzoic ester (1.0 mmol), a 2-fluoronitrobenzene (0.5 mmol) and $Cs_2CO_3$ (0.33 g, 1.0 mol) in DMF (3 mL) was stirred at 40° C. for 2 h. The mixture was diluted with EtOAc (10 mL) and washed with 2 M aqueous NaOH-solution (2×5 mL), dried ($Na_2SO_4$), concentrated, flash chromatographed ($SiO_2$, toluene:heptane:EtOAc-system), and concentrated. The residue was taken up in THF (4 mL), 1 M aqueous LiOH (3 mL) was added and the resulting mixture was stirred at 80° C. for 1 h, and then allowed to obtain room temperature. 2 M aqueous HCl was added until a pH of 2 was reached. The aqueous phase was extracted with EtOAc (3×). The combined organic phases were dried ($Na_2SO_4$) and concentrated. The residue was taken up in EtOH and a mixture of $K_2CO_3$ (0.35 g, 2.55 mmol) and $Na_2S_2O_4$ (0.44 g, 2.5 mmol) in water was added and the resulting mixture was stirred for 1 h. The mixture was diluted with water and washed with 1 M aqueous NaOH-solution (2×5 mL) and then dried ($Na_2SO_4$) and concentrated.

The residue was taken up in $CH_3CN$, 1-ethyl-3-(3-dimethylaminopropyl)carbodiimide hydrochloride (143 mg 0.75 mmol), 1-hydroxybenzotriazole hydrate (160 mg, 0.75 mmol), triethylamine (311 µL, 2.25 mmol), and N,N-dimethylaminopyridine (catalytic amount) were added. The resulting mixture was heated in a capped tube using microwave assisted heating (140° C., 10 min). The mixture was diluted with EtOAc, washed with saturated aqueous $NaHCO_3$-solution, dried ($Na_2SO_4$) and concentrated. The residue was taken up in dioxane and added to a mixture of $TiCl_4$ (0.55 mL, 0.55 mmol, 1 M in toluene) and piperazine (0.22 g, 2.5 mmol) in dioxane at 50° C. The resulting mixture was stirred at 100° C. over night, and then allowed to obtain room temperature. To the mixture was added aqueous HCl (3 mL, 2 M) and then the aqueous phase was extracted with EtOAc (2×4 mL). To the aqueous phase was added aqueous NaOH (6 mL, 2 M) and the resulting suspension was extracted with EtOAc (3×3 mL). The combined organic phases were concentrated and purified by HPLC.

Example 99

2-Bromo-8-methyl-11-(piperazin-1-yl)-dibenzo[b,f][1,4]oxazepine (189JO63A)

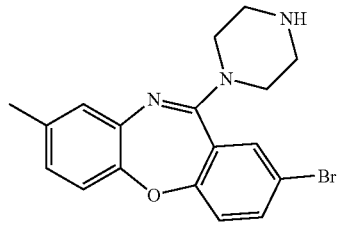

4-Fluoro-3-nitrotoluene (78 mg, 0.5 mmol) and methyl 5-bromo-2-hydroxybenzoate (231 mg, 1 mmol) were reacted according to GP6 to give 13 mg of the title compound (189JO63A). MS (ESI) 372 (MH$^+$). Purity for MH$^+$ (UV/MS) 100/100.

Example 100

7-Chloro-4-methyl-11-(piperazin-1-yl)-dibenzo[b,f][1,4]oxazepine (189JO63B)

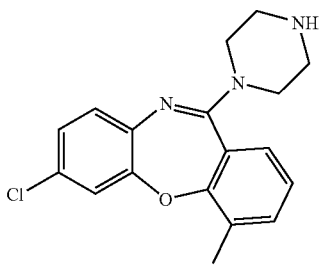

4-Chloro-2-fluoronitrobenzene (88 mg, 0.5 mmol) and methyl 2-hydroxy-3-methylbenzoate (166 mg, 1 mmol) were

Example 101

8-Phenyl-11-(piperazin-1-yl)-dibenzo[b,f][1,4]ox-azepine (189JO64)

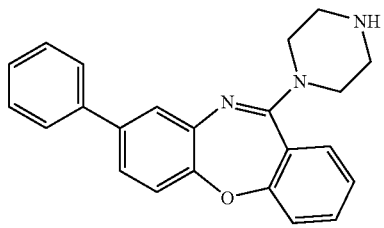

To a mixture of 8-bromo-10H-dibenzo[b,f][1,4]oxazepin-11-one (189JO56) (30 mg, 0.12 mmol), benzene boronic acid (18 mg, 0.15 mmol) and $K_2CO_3$ (34 mg, 0.24 mmol) in deoxygenised toluene/EtOH/$H_2O$ (1.5 mL) was added tetrakis(triphenylphosphine)palladium(0) (catalytic amount) and the resulting mixture was heated in a capped tube in a microwave oven (140° C., 15 min). The mixture was diluted with EtOAc, washed with saturated aqueous $NaHCO_3$-solution, dried ($Na_2SO_4$) and concentrated to give crude 8-phenyl lactam. A mixture of the intermediate 8-phenyl lactam in dioxane (1 mL) was added to a mixture of $TiCl_4$ (0.27 mL, 0.27 mmol, 1 M in toluene) and piperazine (0.103 g, 1.2 mmol) in dioxane at 50° C. The resulting mixture was stirred at 100° C. over night and then allowed to obtain room temperature. To the mixture was added aqueous HCl (3 mL, 2 M) and then the aqueous phase was extracted with EtOAc (2×4 mL). To the aqueous phase was added aqueous NaOH (6 mL, 2 M) and the resulting suspension was extracted with EtOAc (3×3 mL). The combined organic phases were applied onto a SCX-2 ion exchange column. The column was washed with MeOH, and then the product was eluted with $NH_3$ (7 N in MeOH) concentrated and purified by HPLC to give 16 mg of the title compound (189JO64). MS (ESI) 356 (MH$^+$). Purity for MH$^+$ (UV/MS) 100/99.

Example 102

8-Chloro-11-(piperidin-4-yl)-5H-dibenzo[b,e][1,4]diazepine (160FE67A)

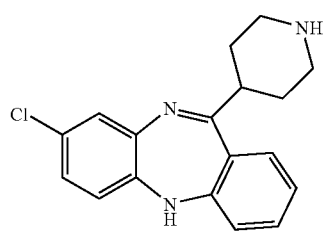

4-CBZ-piperidylzinc iodide (generated from of 4-CBZ-piperidyl iodide (345 mg, 1.0 mmol) using zinc metal and dibromoethane) (0.8 mmol) was added at 50° C. to a solution of 8,5-dichloro-5H-dibenzo[b,e][1,4]diazepine (160FE64) (106 mg, 0.4 mmol) and $PdCl_2(PPh_3)_2$ (18 mg, 0.04 mmol) in dry THF (2 ml). The reaction was shaken for 16 h and then quenched by the addition of aqueous saturated $NH_4Cl$-solution. The resulting mixture was extracted twice with ether and the combined ethereal phases were washed with brine and dried ($Na_2SO_4$). Filtration followed by concentration at reduced pressure of the organic phase gave a crude product. $BBr_3$ (100 µl) added at −30° C. was added to the crude product dissolved in $CH_2Cl_2$ (1 ml). The reaction temperature was then slowly increased to 0° C. TLC indicated complete conversion of the starting material and $Et_3N$, $H_2O$ and EtOAc were sequentially added to the reaction mixture. The organic phase was washed with brine and dried ($Na_2SO_4$). Filtration followed by concentration at reduced pressure gave a crude product, which was purified by HPLC to give 2.3 mg of the title compound (160FE67A). MS (ESI) 312 (MH$^+$). Purity for MH$^+$ (UV/MS) 99/96.

Example 103

5-Benzyl-8-chloro-11-(piperidin-4-yl)-5H-dibenzo[b,e][1,4]diazepine (160FE67B)

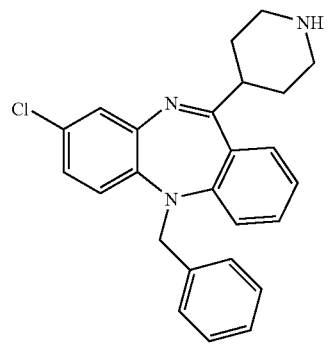

4.4 mg of the title compound (160FE67B) was isolated as a by-product in the synthesis of Example 102. MS (ESI) 402 (MH$^+$). Purity for MH$^+$ (UV/MS) 85/87.

Example 104

General Procedure 7 (GP7)

A mixture of a 2-aminobenzoic acid (1 eq.), a 2-fluoronitrobenzene (2 eq. or 3 eq.) and $K_2CO_3$ (3 eq.) in DMF was heated to 100° for 2 hour then allowed to obtain room temperature. The organic phase was extracted with 0.1 M aqueous NaOH-solution (3 x). The combined aqueous phases were acidified with 4 M aqueous HCl and extracted with EtOAc (3×). The combined organic phases were dried ($Na_2SO_4$) and concentrated. The residue was taken up in EtOH and a solution of $K_2CO_3$ (5 eq.) and $Na_2S_2O_4$ (5 eq.) in water was added and the resulting mixture was stirred for 1 h. The mixture was concentrated and the residue taken up in EtOAc. The mixture was acidified with aqueous HCl (2 M) and then the aqueous phase was extracted with EtOAc (3×) and the combined organic phases were concentrated.

The residue was taken up in xylene and the resulting mixture was stirred at 130° C. over night. The mixture was diluted with EtOAc, washed with saturated aqueous $NaHCO_3$-solution, dried ($Na_2SO_4$), concentrated, and flash chromatographed ($SiO_2$, heptane:EtOAc system)

Example 105

8-Bromo-5,10-dihydro-dibenzo[b,e][1,4]diazepine-11-one (166JO31)

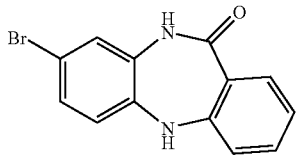

5-Bromo-2-fluoronitrobenzene (1.6 g, 7.4 mmol) and 2-aminobenzoic acid (0.50 g, 3.6 mmol) were reacted according to GP7 to give 331 mg of the title compound (166JO31). MS (ESI) 289 (MH$^+$). Purity for MH$^+$ (UV) 93%.

Example 106

5,10-Dihydro-dibenzo[b,e][1,4]diazepine-11-one (160FE15A)

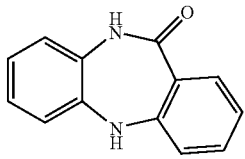

2-Fluoronitrobenzene (847 g, 6 mmol) and 2-aminobenzoic acid (274 mg, 2.0 mmol) were reacted according to GP7 to give 130 mg of the title compound (160FE15A).

Example 107

8-Fluoro-5,10-dihydro-dibenzo[b,e][1,4]diazepine-11-one (160FE15C)

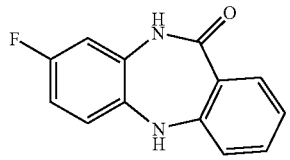

2,4-Difluoronitrobenzene (0.96 g, 6 mmol) and 2-aminobenzoic acid (274 mg, 2.0 mmol) were reacted according to GP7 to give 100 mg of the title compound (160FE15C).

Example 108

8,5-Dichloro-5H-dibenzo[b,e][1,4]diazepine (160FE64)

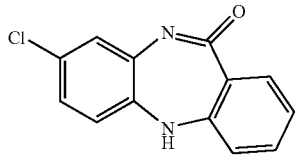

N,N-dimethylaniline (5.1 ml, 40 mmol) and phosphorus oxychloride (2.8 ml, 30 mmol) was added to a mixture of 8-chloro-5,10-dihydro-dibenzo[b,e][1,4]diazepine-11-one (2.45 g, 10 mmol) in dry toluene (20 ml). The mixture was shaken at 95° C. for 2 h. The temperature was then decreased and the excess N,N-dimethylaniline and phosphorus oxychloride were removed at reduced pressure using an oil pump. The remaining oil was dissolved in dioxane (20 ml) and aqueous Na$_2$CO$_3$-solution (10 ml, 2 M) was added. The two-phase mixture was shaken at 80° C. for 30 min. The temperature was then decreased and ether was added to the reaction mixture. The ethereal phase was washed with saturated aqueous NaCl-solution, dried (Na$_2$SO$_4$) and finally concentrated at reduced pressure. The obtained oil crystallized upon standing at room temperature. Recrystallization (heptane-ether) gave 1.8 g (69%) of the title compound (160FE64). $^1$H NMR (CDCl$_3$) δ 7.61 (dd, 1H, J=1.4, 7.8 Hz), 7.31 (dt, 1H, J=1.5, 8.0 Hz), 7.15 (d, 1H, J=2.5 Hz), 7.02 (m 2H), 6.66 (dd, 1H, J=1.0, 7.8 Hz), 6.58 (d, 1H, J=8.4 Hz), 4.94 (bs, 1H). $^{13}$C NMR (CDCl$_3$) δ 157.2, 152.4, 140.3, 138.9, 134.0, 131.9, 129.7, 128.5, 128.0, 127.0, 123.5, 121.0, 119.8.

Example 109

8-Chloro-11-methylsulfanyl-5H-dibenzo[b,e][1,4]diazepine (166JO50)

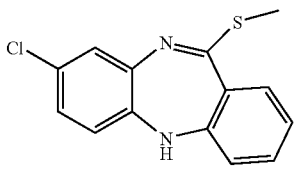

A mixture of 8-chloro-5,10-dihydro-dibenzo[b,e][1,4]diazepine-11-one (500 mg, 2.05 mmol) and 2,4-bis(4-methoxyphenyl)-1,3-dithia-2,4-diphosphetane-2,4-disulfide (480 mg, 1.19 mmol) in toluene (4 mL) was heated in a capped tube in a microwave oven (120° C., 30 minutes). The mixture was chromatographed (SiO$_2$, heptane:EtOAc, 2:1) to give 599 mg of the intermediate thiolactam. To a mixture of the intermediate thiolactam in THF (10 mL) was added MeI (633 µL, 10.3 mmol) and the resulting mixture was heated at reflux for 4 h. The mixture was concentrated to give 610 mg of the crude title compound (166JO50) (purity 50%).

Example 110

N,N-diethyl(2-bromobenzyl)amide (189JO10)

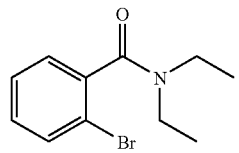

To a mixture of 2-bromo benzylchloride (3.5 g, 16 mmol) in CH$_2$Cl$_2$ (50 mL) at 0° C. was added diethylamine (3.2 mL, 32 mmol) drop-wise and the resulting mixture was allowed to obtain room temperature. After 30 minutes, water was added, the mixture was diluted with CH$_2$Cl$_2$, washed with saturated aqueous NaHCO$_3$-solution and saturated aqueous NH$_4$Cl-solution, dried (Na$_2$SO$_4$) and concentrated to give 3.9 g (95%) of the title compound (189JO10). $^1$H NMR (CDCl$_3$) δ 7.54 (m, 1H), 7.32 (m, 1H), 7.22 (m, 2H), 3.79 (m, 1H), 3.33 (m, 1H), 3.13 (m, 2H), 1.26 (t, 3H, J=7.2 Hz), 1.05 (t, 3H, J=7.0 Hz). $^{13}$C NMR (CDCl$_3$) δ 168.5, 139.0, 132.8, 130.0, 127.61, 127.59, 119.3, 42.8, 39.0, 14.0, 12.6

Example 111

2[(4-Chloro-2-methylphenyl)-(4-methoxybenzyl)-amino]-N,N-diethylbenzamide (189JO26)

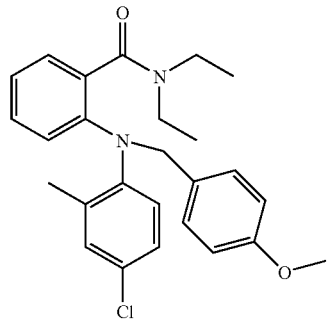

To a mixture of N,N-diethyl(2-bromobenzyl)amide (189JO10) (1.41 g, 5.50 mmol) and 4-chloro-2-methylaniline (1.01 g, 7.15 mmol) in deoxygenised toluene (14 mL) was added NaO$^t$Bu (0.74 g, 7.7 mmol), rac-BINAP (110 mg, 0.17 mmol) and Pd(OAc)$_2$ (18 mg, 0.08 mmol) and the resulting mixture was stirred under Ar for 14 h at 80° C. The mixture was filtered through celite, concentrated and flash chromatographed (SiO$_2$, heptane:EtOAc, 10:1-4:1) which gave unprotected intermediate ketone (1.50 g) containing about 15% impurities.

The mixture containing the intermediate was dissolved in DMF (20 mL). p-Methoxybenzyl chloride (0.90 mL, 6.6 mmol) was added and then NaH (0.23 g, 5.6 mmol, 60% in mineral oil) was added portions-wise. The resulting mixture was stirred at room temperature for 1 h, and then quenched by addition of saturated aqueous NaHCO$_3$-solution. The mixture was diluted with EtOAc, washed with saturated aqueous NaHCO$_3$-solution, dried (Na$_2$SO$_4$), concentrated and flash chromatographed (SiO$_2$, toluene:EtOAc 10:1) to give 1.66 g (68%) of the title compound (189JO26). $^1$H NMR (CDCl$_3$) δ 7.35 (m, 2H), 7.20 (m, 1H), 7.09-6.99 (m, 4H), 6.91 (m, 2H), 6.80 (m, 2H), 4.84/4.54 (Abq, 2H, J=16.2 Hz), 3.74 (s, 3H), 3.18 (m, 2H), 3.03 (m, 1H), 2.48 (m, 1H), 2.17 (s, 3H), 1.01 (t, 3H, J=7.2 Hz), 0.97 (t, 3H, J=7.0 Hz), $^{13}$C NMR (CDCl$_3$) δ 169.6, 158.7, 146.53, 146.51, 137.0, 131.3, 130.9, 130.4, 129.6, 129.3, 128.7, 127.8, 127.4, 126.3, 122.8, 121.4, 114.0, 57.1, 55.3, 43.3, 39.0, 19.1, 13.9, 12.9. MS (ESI) 437 (MH$^+$).

Example 112

2-Chloro-5-(4-methoxybenzyl)-5,11-dihydrodibenzo[b,f]azepin-11-one (189JO27)

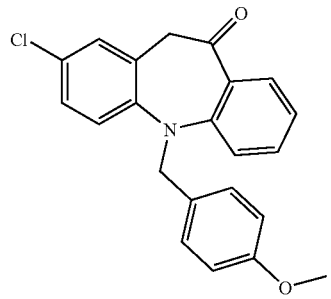

To a mixture of diisopropylamine (1.09 mL, 7.8 mmol) and N,N,N,N-tetramethylenediamine (1.17 mL, 7.8 mmol) in dry THF (19 mL) at −20° C. was added n-BuLi (5.54 mL, 1.4 M in hexane) and the resulting mixture was stirred at −20° C. for 5 minutes. Then a mixture of 2[(4-chloro-2-methylphenyl)-(4-methoxybenzyl)-amino]-N,N-diethylbenzamide (189JO26) (1.36 g, 3.1 mmol) in dry THF (38 mL) was added and the resulting mixture was stirred at −20° for 4 h. The reaction was quenched by addition of saturated aqueous NH$_4$Cl-solution. The mixture was diluted with EtOAc, washed with water, dried (Na$_2$SO$_4$), concentrated, and flash chromatographed (SiO$_2$, toluene:heptane, 7:1-1:0) to give 665 mg (59%) of the title compound (189JO27). $^1$H NMR (CDCl$_3$) δ 8.15 (dd, 1H, J=1.8, 8.0 Hz), 7.43 (m, 1H), 7.24 (m, 4H), 7.17 (d, 1H, J=8.6 Hz), 7.12 (dd, 1H, J=2.4, 8.6 Hz), 7.00 (dt, 1H, J=0.8, 7.0 Hz), 6.81 (m, 2H), 5.09 (s, 2H), 4.00 (s, 2H), 3.75 (s, 3H); $^{13}$C NMR (CDCl$_3$) δ 190.3, 159.1, 149.5, 146.2, 134.1, 132.4, 131.3, 131.1, 129.1, 129.0, 128.6, 127.3, 126.4, 123.4, 121.0, 118.5, 114.2, 55.5, 19.3. MS (ESI) 364 (MH$^+$).

Example 113

2-(4-Chloro-2-nitro-phenylsulfanyl)-benzoic acid methyl ester (189JO09)

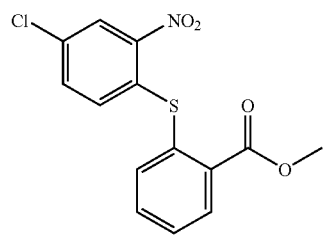

To a mixture of 5-chloro-2-nitrofluorobenzene (176 mg, 1 mmol) and methyl thiosalicylate (275 μL, 2 mmol) in DMF (5 mL) was added Cs$_2$CO$_3$ (652 mg, 2 mmol) and the resulting mixture was stirred at room temperature for 2 h. The mixture was diluted with CH$_2$Cl$_2$, washed with water, dried (Na$_2$SO$_4$), concentrated and flash chromatographed (SiO$_2$, heptane:toluene, 1:10-1:4) to give 300 mg (92%) of the title compound (189JO09). $^1$H NMR (CDCl$_3$) δ 8.15 (d, 1H J=2.4 Hz), 7.94 (m, 1H), 7.53-7.46 (m, 3H), 7.34 (dd, 1H, 2.4, 8.6 Hz), 6.95 (d, 1H, J=8.8 Hz), 3.82 (s, 3H).

Example 114

2-(2-Amino-4-chlorophenylsulfanyl)-benzoic acid methyl ester (189JO11)

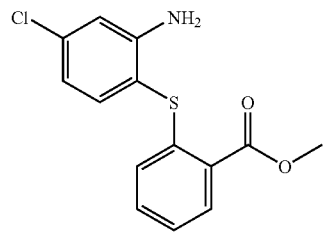

To a mixture of 2-(4-chloro-2-nitro-phenylsulfanyl)-benzoic acid methyl ester (189JO09) (232 mg, 0.72 mmol) in EtOH (5 mL) was added SnCl$_2$.2H$_2$O (812 mg, 3.6 mmol)

and the resulting mixture was stirred at 80° C. for 2 h and then concentrated. The residue was treated with ice, and then Na$_2$CO$_3$ was added until a pH of 10 was reached. EtOAc was added and the slurry was filtered through celite. The EtOAc-phase was washed with water and brine, dried (Na$_2$SO$_4$) and concentrated to give 149 mg (70%) of the title compound (189JO11). $^1$H NMR (CDCl$_3$) δ 8.02 (dd, 1H, J=1.6, 7.8 Hz), 7.39 (d, 1H, J=8.2 Hz), 7.29 (m, 1H), 7.15 (dt, 1H, J=1.2, 7.8 Hz), 6.87 (d, 1H, J=2.2 Hz), 6.80 (dd, 1H, J=2.2, 8.2 Hz), 6.76 (dd, 1H, J=1.2, 8.0 Hz), 3.96 (s, 3H).

Example 115

8-Chloro-10H-dibenzo[b,f][1,4]thiazepin-11-one (189JO13)

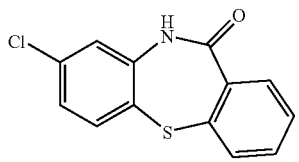

A mixture of 2-(2-amino-4-chlorophenylsulfanyl)-benzoic acid methyl ester (189JO11) (149 mg, 0.51 mmol) and AlMe$_3$ (355 µL, 0.71 mmol, 2 M in toluene) in CH$_2$Cl$_2$ (3 mL) was stirred at ambient temperature for six days, and then water was added carefully. The mixture was diluted with CH$_2$Cl$_2$, and was acidified with 2 M aqueous HCl. The organic phase was separated, dried (Na$_2$SO$_4$), concentrated and flash chromatographed (heptane:EtOAc, 5:1-3:1) to give 38 mg (29%) of the title compound (189JO13). MS (ESI) 262 (MH$^+$).

Example 116

2-(Chloro-2-nitro-phenoxy)-benzoic acid methyl ester (189JO29A)

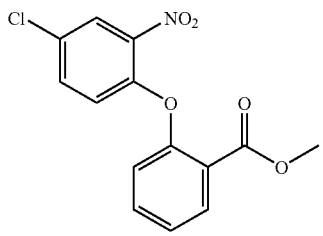

Cs$_2$CO$_3$ (1.30 g, 4 mmol) was added to a mixture of 5-chloro-2-nitrofluorobenzene (352 mg, 2 mmol) and methyl 2-hydroxybenzoate (0.52 mL, 4 mmol) in DMF (6 mL) and the resulting mixture was stirred at room temperature for 2 h. The mixture was diluted with CH$_2$Cl$_2$, washed with water, dried (Na$_2$SO$_4$), concentrated and flash chromatographed (SiO$_2$, heptane:EtOAc, 10:1-4:1) to give 505 mg (82%) of the title compound (189JO29A). $^1$H NMR (CDCl$_3$) δ 8.02 (dd, 1H, J=1.8, 7.8 Hz), 7.96 (d, 1H, J=1.9 Hz), 7.59 (dt, 1H, J=2.0, 7.6 Hz), 7.39 (dd, 1H, J=2.5, 9.0 Hz), 7.24 (dt, 1H, J=1.2, 7.6 Hz), 7.13 (dd, 1H, J=1.2, 8.0 Hz), 6.74 (d, 1H, J=9.0 Hz), 3.77 (s, 3H).

Example 117

8-Chloro-10H-dibenzo[b,f][1,4]oxazepin-11-one (189JO29C)

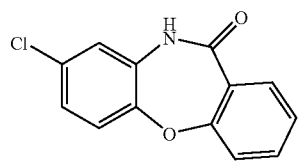

Pd (catalytic amount, 5% on carbon) was added to a solution of 2-(chloro-2-nitro-phenoxy)-benzoic acid methyl ester (189JO29A) (505 mg, 1.64 mmol) in EtOAc (20 mL) and the resulting mixture was hydrogenated (H$_2$, 1 atm.) for 48 h, then filtered through celite and concentrated. The residue was taken up in toluene (6 mL) and NaH (160 mg, 4.0 mmol, 60% in mineral oil) was added. The resulting mixture was stirred at 80° C. over night, and then quenched by addition of saturated aqueous NH$_4$Cl-solution. The resulting mixture was diluted with EtOAc, washed with water, dried (Na$_2$SO$_4$), concentrated and flash chromatographed (SiO$_2$, toluene:EtOAc, 4:1), which gave 171 mg (42%) of the title compound (189JO29C). $^1$H NMR (CDCl$_3$) δ 8.12 (bs, 1H), 7.95 (dd, 1H, J=1.8, 8.0 Hz), 7.54 (dt, 1H, J=1.8, 8.0 Hz), 7.29-7.19 (m, 3H), 7.08 (dd, 1H, J=2.3, 8.6 Hz), 7.04 (d, 1H, J=2.3 Hz). MS (ESI) 246 (MH$^+$).

Example 118

3-Chloro-5,11-dihydro-dibenzo[b,e]azepin-6-one (189JO59)

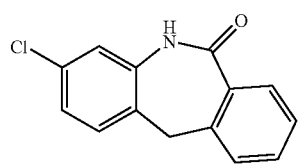

To a mixture of 5-chloro-2-methylphenyl isocyanate (100 µL, 0.73 mmol) in CCl$_4$ (2 mL) was added sulfuryl chloride (118 µL, 0.88 mmol) and 2,2'-azobis(isobutyronitrile) (catalytic amount) and the resulting mixture was refluxed for 20 h. The mixture was allowed to obtain room temperature, then diluted with CH$_2$Cl$_2$, washed with saturated aqueous NaHCO$_3$-solution, dried (Na$_2$SO$_4$) and concentrated. The mixture was taken up in benzene (2 mL) and a mixture of AlCl$_3$ (160 mg, 1.2 mmol) in benzene (1 mL) was added. The resulting mixture was stirred at 80° for 4 h, and then allowed to obtain room temperature. The mixture was filtered through a short column (SiO$_2$, heptane:EtOAc, 1:1) to give 25 mg (14%) of the title compound (189JO59). $^1$H NMR (CDCl$_3$) δ 8.18 (bs, 1H), 7.92 (dd, 1H, J=1.2, 7.8 Hz), 7.46 (dt 1H, J=1.4, 7.4 Hz), 7.34 (dt, 1H, J=1.2, 7.4 Hz), 7.23 (m, 2H), 7.07 (m, 2H), 3.92 (s 2H). MS (ESI) 244 (MH$^+$)

Example 119

8-Bromo-10H-dibenzo[b,f][1,4]oxazepin-11-one (189JO56)

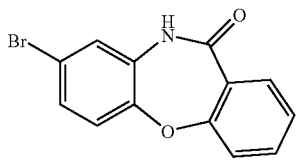

A mixture of a methyl 2-hydroxybenzoate (1.0 mL, 10.0 mmol), 5-bromo-2-fluoronitrobenzene (0.62 mL, 5.0 mmol) and $Cs_2CO_3$ (3.3 g, 10.0 mol) in DMF (12 mL) was stirred at 40° C. for 2 h. The mixture was diluted with EtOAc and washed with 2 M aqueous NaOH-solution. To the EtOAc-phase was added EtOH, $H_2O$, $K_2CO_3$ (2.8 g, 20 mmol) and $Na_2S_2O_4$ (3.5 g, 20 mmol) and the resulting mixture was stirred vigorously for 1 h. The aqueous phase was removed and the organic phase was washed with 1 M aqueous NaOH-solution and then concentrated. The residue was taken up in DMF (1 mL) and then toluene (4 mL) and NaH (60 mg, 1.5 mmol, 60% in mineral oil) were added and the resulting mixture was stirred at 80° C. over night, then quenched by addition of saturated aqueous $NH_4Cl$-solution. The resulting mixture was diluted with EtOAc, washed with 2 M aqueous NaOH-solution, dried ($Na_2SO_4$), concentrated, filtered through a short $SiO_2$-column, concentrated and crystallised from heptane:EtoAc to give 130 mg of the title compound (189JO56). MS (ESI) 290 (MH$^+$). Purity for MH$^+$ (UV/MS) 100/100.

Example 120

General Procedure 8 (GP8)

A BOC-protected diamine (1.8 eq.) was added to 8-chloro-11-methylsulfanyl-5H-dibenzo[b,e][1,4]diazepine (166JO50) (purity 50%, 1 eq.) in pyridine. The resulting mixture was heated in a capped tube at 110° C. for 66 h. The mixture was concentrated and then diluted with $CH_2Cl_2$:trifluoroacetic acid (2:1-ratio). The resulting mixture was stirred at ambient temperature over night, and then concentrated. The residue was taken up in $CH_2Cl_2$ and washed with saturated aqueous $NaHCO_3$-solution. The organic phase was applied onto a SCX-2 ion exchange column. The column was washed with MeOH, and then the product was eluted with $NH_3$ (7 N in MeOH), concentrated and purified on HPLC.

Example 121

(8-Chloro-5H-dibenzo[b,e][1,4]diazepin-11-yl)-(S)-1-pyrrolidin-2-yl-methyl-amine (166JO51)

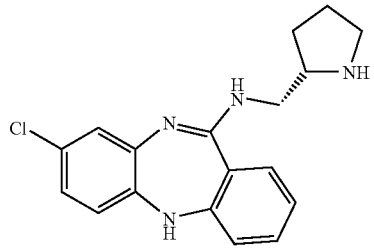

8-Chloro-11-methylsulfanyl-5H-dibenzo[b,e][1,4]diazepine (166JO50) (50 mg, 0.11 mmol) and (S)-(2-aminomethyl)-1-N-(tert-butoxycarbonylamino)-pyrrolidine (39 mg, 0.2 mmol) were reacted according to GP8 to give 3.0 mg of the title compound (166JO51). MS (ESI) 327 (MH$^+$). Purity for MH$^+$ (UV/MS) 100/92.

Example 122

1-(8-Chloro-5H-dibenzo[b,e][1,4]diazepin-11-yl)-piperidine-4-yl-amine (166JO55)

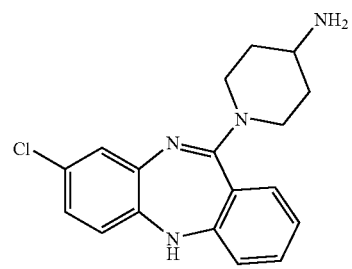

8-Chloro-11-methylsulfanyl-5H-dibenzo[b,e][1,4]diazepine (166JO50) (50 mg, 0.11 mmol) and 4-(tert-butoxycarbonylamino)-aminopiperidine (39 mg, 0.2 mmol) were reacted according to GP8 to give 6.5 mg of the title compound (166JO55). MS (ESI) 327 (MH$^+$). Purity for MH$^+$ (UV/MS) 100/99.

Example 123

1-(8-Chloro-5H-dibenzo[b,e][14]diazepin-11-yl)-pyrrolidin-3-yl-amine (166JO64)

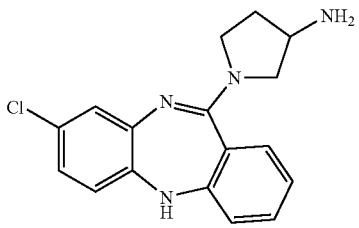

8-Chloro-11-methylsulfanyl-5H-dibenzo[b,e][1,4]diazepine (166JO50) (100 mg, 0.22 mmol) and 3-(tert-butoxycarbonylamino)pyrrolidine (73 mg, 0.4 mmol) were reacted according to GP8 to give 8.1 mg of the title compound (166JO64). MS (ESI) 313 (MH$^+$). Purity for MH$^+$ (UV/MS) 100/94.

Example 124

(8-Chloro-5H-dibenzo[b,e][14]diazepin-11-yl)-(R)-1-pyrrolidin-2-yl-methyl-amine (166JO70)

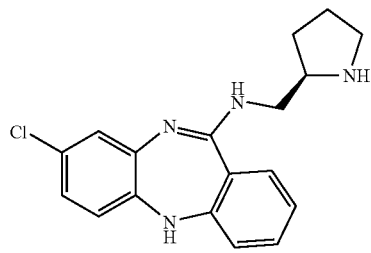

8-Chloro-11-methylsulfanyl-5H-dibenzo[b,e][1,4]diazepine (166JO50) (100 mg, 0.22 mmol) and (R)-(2-aminomethyl)-1-N-(tert-butoxycarbonylamino)-pyrrolidine (78 mg, 0.4 mmol) were reacted according to GP8 to give 7.6 mg of the title compound (166JO70). MS (ESI) 327 (MH⁺). Purity for MH⁺ (UV/MS) 100/90.

Example 125

(8-Chloro-5H-dibenzo[b,e][14]diazepin-11-yl)-pyrrolidin-3-yl-amine (166JO74)

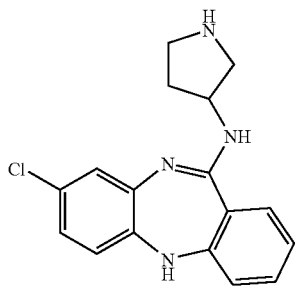

8-Chloro-11-methylsulfanyl-5H-dibenzo[b,e][1,4]diazepine (166JO50) (100 mg, 0.22 mmol) and 3-amino-1-N-(tert-butoxycarbonylamino)pyrrolidine (73 mg, 0.4 mmol) were reacted according to GP8 to give 7.7 mg of the title compound (166JO74). MS (ESI) 313 (MH⁺). Purity for MH⁺ (UV/MS) 100/90.

Example 126

8-Chloro-11-(2,5-diaza-bicyclo[2.2.1]hept-2-yl)-5H-dibenzo[b,e][1,4]diazepine (166JO39-2)

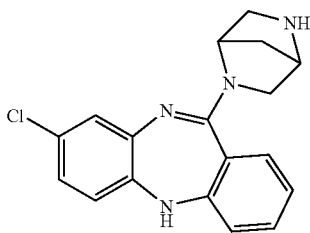

8-Chloro-11-methylsulfanyl-5H-dibenzo[b,e][1,4]diazepine (166JO50) (50 mg, 0.11 mmol) and N-(tert-butoxycarbonylamino)-2,5-diazabicyclo[2.2.1]heptane (34 mg, 0.2 mmol) were reacted according to GP8 to give 15 mg of the title compound (166JO39-2). MS (ESI) 324 (MH⁺). Purity for MH⁺ (UV/MS) 93/100.

Example 127

Acetidin-3-yl-(8-chloro-5H-dibenzo[b,e][1,4]diazepine-11-yl)amine (189JO65)

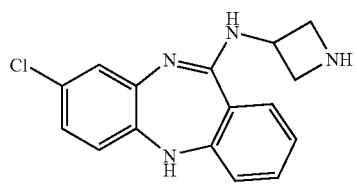

To 8,5-Dichloro-5H-dibenzo[b,e][1,4]diazepine (160FE64) (30 mg, 0.11 mmol) in dioxane (2.0 mL) was added 3-amino-azetidine-1-carboxylic acid tert-butyl ester (59 mg, 0.34 mmol) and Cs₂CO₃ (74 mg, 0.23 mmol) and the resulting mixture was heated in capped tube using microwave assisted heating (170° C., 40 minutes). The mixture was diluted with EtOAc, washed with water, dried (Na₂SO₄) and concentrated. The residue was taken up in CH₂Cl₂ (2 mL) and trifluoroacetic acid (1 mL) was added. The resulting mixture was stirred at ambient temperature over night, and then concentrated. The residue was taken up in CH₂Cl₂ and washed with saturated aqueous NaHCO₃-solution. The organic phase was applied onto a SCX-2 ion exchange column. The column was washed with MeOH, and then the product was eluted with NH₃ (7 N in MeOH), concentrated, and purified by HPLC to give 16 mg of the title compound (189JO65). MS (ESI) 299 (MH⁺). Purity for MH⁺ (UV/MS) 97/90.

Example 128

General Procedure 9 (GP9)

A mixture of a 3-aminomethyl ester (1 eq.), 5-bromo-2-fluoronitrobenzene (1 eq.) and K₂CO₃ (4 eq.) in DMF was heated to 60° C. for 1 hour, and then allowed to obtain room temperature. The mixture was diluted with CH₂Cl₂ and washed with saturated aqueous NH₄Cl-solution, dried (Na₂SO₄) and concentrated. The residue was taken up in EtOH and a mixture of K₂CO₃ (5 eq.) and Na₂S₂O₄ (5 eq.) in water was added and the resulting mixture was stirred vigorously for 1 h. The aqueous phase was extracted with EtOAc (3×) and the combined organic phases were dried (Na₂SO₄) and concentrated.

The residue was taken up in CH₃CN, H₂SO₄ (10 vol-%, 98%) was added, and the resulting mixture was stirred at 80° C. for 1 h. The mixture was diluted with CH₂Cl₂, washed with saturated aqueous NaHCO₃-solution, dried (Na₂SO₄), concentrated, flash chromatographed (SiO₂, heptane:EtOAc-system), and concentrated to give intermediate lactam.

The residue was taken up in dioxane and added to a mixture of TiCl₄ (1.1 eq., 1 M in toluene) and piperazine (5 eq.) in dioxane at 50° C. The resulting mixture was stirred at 100° C. over night, and then allowed to obtain room temperature. To the mixture was added aqueous HCl (2 M) until acidic solution and then the aqueous phase was extracted with EtOAc (2×). To the aqueous phase was added aqueous NaOH (2 M) until basic solution and the resulting suspension was extracted with EtOAc (3×). The combined organic phases were concentrated and flash chromatographed (SiO₂, CH₂Cl₂:MeOH, NH₃(7N in MeOH))-system.

Example 129

7-Bromo-4-(piperazin-1-yl)-2,3-dihydro-1H-benzo[b][1,4]diazepine (166JO47)

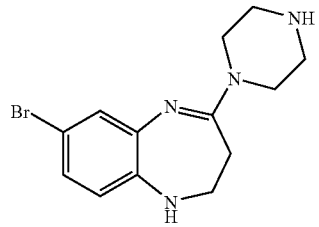

5-Bromo-2-fluoronitrobenzene (440 mg, 2.0 mmol) and methyl 3-amino propionate hydrochloride (920 mg, 3.0 mmol) were reacted according to GP9 to give 4.0 mg of the title compound (166JO47). MS (ESI) 309 (MH$^+$). Purity for MH$^+$ (UV/MS) 100/100.

Example 130

7-Bromo-2-methyl-(piperazin-1-yl)-2,3-dihydro-1H-benzo[b][1,4]diazepine (166JO95)

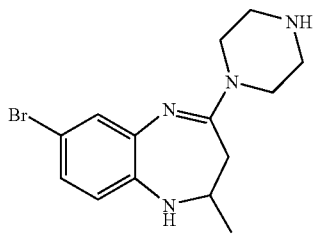

5-Bromo-2-fluoronitrobenzene (440 mg, 2.0 mmol) and methyl 3-amino butyrate (787 mg, 3.0 mmol) were reacted according to GP9 to give 12 mg of the title compound (166JO95). MS (ESI) 323 (MH$^+$). Purity for MH$^+$ (UV/MS) 100/100.

Example 131

7-Bromo-2-phenyl-4-(piperazine-1-yl)-2,3-dihydro-1H-benzo[b][1,4]diazepine (189JO20)

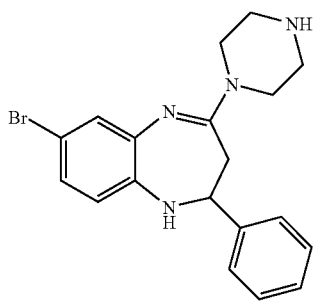

5-Bromo-2-fluoronitrobenzene (440 mg, 2.0 mmol) and ethyl 3-amino-3-phenylpropionate hydrochloride (394 mg, 1.5 mmol) were reacted according to GP9 to give 9.8 mg of the title compound (189JO20). MS (ESI) 385 (MH$^+$). Purity for MH$^+$ (UV/MS) 97/88.

Example 132

7-Bromo-10-(piperazin-1-yl)-1,2,3,3a,4,10a-hexahydro-benzo[b]cyclopenta[e][1,4]diazepine (166JO46)

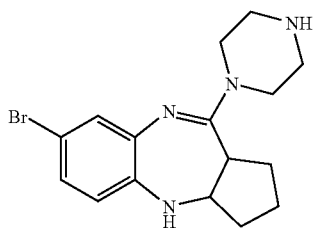

5-Bromo-2-fluoronitrobenzene (110 mg, 0.5 mmol) and cis-2-amino-1-cyclopentanecarboxylic acid hydrochloride (138 mg, 0.75 mmol) were reacted according to GP2 to give 3.0 mg of the title compound (166JO46). MS (ESI) 349 (MH$^+$). Purity for MH$^+$ (UV/MS) 99/88.

Example 133

General Procedure 10 (GP10)

A zinc reagent (0.4 mmol) was added at room temperature to a solution of 8,5-Dichloro-5H-dibenzo[b,e][1,4]diazepine (160FE64) (53 mg, 0.2 mmol) and PdCl$_2$(PPh$_3$)$_2$ (9 mg, 0.02 mmol) in dry THF (1 ml). The reaction was shaken until complete conversion (1-16 h, TLC) and then quenched by the addition of aqueous saturated NH$_4$Cl. The resulting mixture was extracted twice with ether and the combined ethereal phases were washed with brine and dried over Na$_2$SO$_4$. Filtration followed by concentration at reduced pressure of the organic phase gave a crude product, which was purified using column chromatography (heptane:EtOAc-system).

Example 134

8-Chloro-11-(4-fluorobenzyl)-5H-dibenzo[b,e][1,4]diazepine (160FE59)

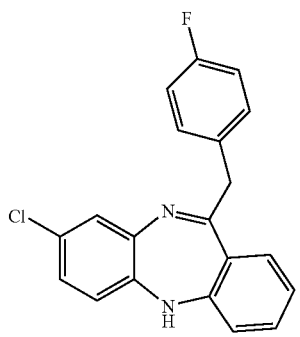

4-Fluorobenzylzinc chloride (0.8 ml, 0.5 M in THF, 0.4 mmol) and 8,5-dichloro-5H-dibenzo[b,e][1,4]diazepine (160FE64) (53 mg, 0.2 mmol) were reacted according GP10 to give 52 mg of the title compound (160FE59). MS (ESI) 337 (MH$^+$). Purity for MH$^+$ (UV/MS) 90/90.

Example 134

8-Chloro-11-(4-fluorophenyl)-5H-dibenzo[b,e][1,4]diazepine (160FE70)

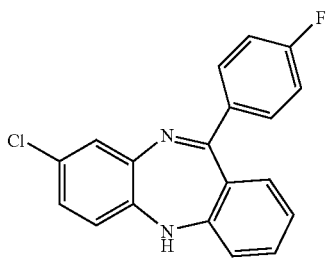

4-Fluorohenylzinc chloride (0.5 ml, 0.5 M in THF, 0.4 mmol) and 8,5-dichloro-5H-dibenzo[b,e][1,4]diazepine (160FE64) (26 mg, 0.1 mmol) were reacted according GP10 to give 23 mg of the title compound (160FE70). MS (ESI) 323 (MH$^+$). Purity for MH$^+$ (UV/MS) 98/100.

Example 135

General Procedure 11 (GP11)

Aqueous Na₂CO₃ (1 ml, 1M) was added at room temperature to a solution of the 8,5-dichloro-5H-dibenzo[b,e][1,4]diazepine (160FE64) (53 mg, 0.2 mmol) (26 mg, 0.1 mmol), Pd(PPh₃)₄ (10 mg), and the appropriate boronic acid reagent (0.12 mmol) in dioxane (3 ml). The mixture was then shaken at 80° C. until complete conversion of the imidoyl chloride (TLC). The temperature was decreased and ether and H₂O were added to the reaction mixture. The ether phase was washed with brine and dried over Na₂SO₄. Filtration followed by concentration at reduced pressure of the organic phase gave a crude product, which was purified using column chromatography (heptane:EtOAc-system).

Example 136

8-Chloro-11-(4-nonylphenyl)-5H-dibenzo[b,e][1,4]diazepine (160FE63)

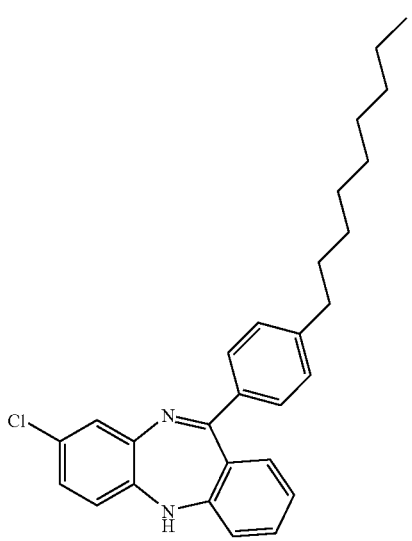

4-Nonylphenylboronic acid (30 mg, 0.12 mmol) and 8,5-dichloro-5H-dibenzo[b,e][1,4]diazepine (160FE64) (26 mg, 0.1 mmol) were reacted according GP11 to give 25 mg of the title compound (160FE63). MS (ESI) 431 (MH⁺). Purity for MH⁺ (UV/MS) 85/85.

Example 137

8-Chloro-11-(pyridin-4-yl)-5H-dibenzo[b,e][1,4]diazepine (160FE69A)

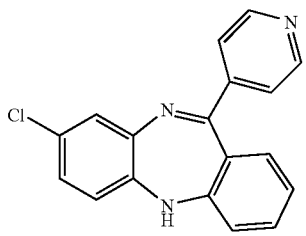

4 pyridyl-4-boronic acid (14 mg, 0.12 mmol) and 8,5-dichloro-5H-dibenzo[b,e][1,4]diazepine (160FE64) (26 mg, 0.1 mmol) were reacted according GP11 to give 9.3 mg of the title compound (160FE69A). MS (ESI) 306 (MH⁺). Purity for MH⁺ (UV/MS) 98/95.

Example 138

8-Chloro-11-(1H-pyrazol-4-yl)-5H-dibenzo[b,e][1,4]diazepine (160FE59)

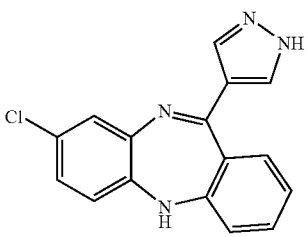

4-(4,4,5,5-Tetramethyl-1,3,2-dioxaborolan-2-yl)-1H-pyrazole (22 mg, 0.12 mmol) and 8,5-dichloro-5H-dibenzo[b,e][1,4]diazepine (160FE64) (26 mg, 0.1 mmol) were reacted according GP11 to give 8.7 mg of the title compound (160FE69B). MS (ESI) 295 (MH⁺). Purity for MH⁺ (UV/MS) 95/100.

Example 139

Functional Screen

Several compounds disclosed herein were evaluated for activity at muscarinic receptors using Receptor Selection and Amplification Technology (R-SAT) as described in U.S. Pat. No. 5,707,798, the disclosure of which is incorporated herein by reference in its entirety. The efficacy (eff) and potency (expressed as $pEC_{50}$) of these compounds are presented in Table 1 at M1, M2, and M3 receptors.

TABLE 1

| Name | M1 | | M2 | | M3 | |
|---|---|---|---|---|---|---|
| | eff | $pEC_{50}$ | eff | $pEC_{50}$ | eff | $pEC_{50}$ |
| 2,7-Dichloro-11-(piperazin-1-yl)-5H-dibenzo[b,e][1,4]diazepine (166JO85F1) | −2 | | −14 | | — | |
| 2-Chloro-11-(piperazin-1-yl)-5H-dibenzo[b,e][1,4]diazepine (166JO85F6) | −5 | | 8 | | — | |
| 2,8-Dichloro-11-(piperazin-1-yl)-5H-dibenzo[b,e][1,4]diazepine (166JO85F2) | 1 | | 24 | | — | |

TABLE 1-continued

| Name | M1 eff | M1 pEC$_{50}$ | M2 eff | M2 pEC$_{50}$ | M3 eff | M3 pEC$_{50}$ |
|---|---|---|---|---|---|---|
| 8-Bromo-2-chloro-11-(piperazin-1-yl)-5H-dibenzo[b,e][1,4]diazepine (166JO85F3) | 10 | | 29 | 5.5 | — | |
| 2-Chloro-11-(piperazin-1-yl)-8-trifluoromethyl-5H-dibenzo[b,e][1,4]diazepine (166JO85F7) | 10 | | 19 | | — | |
| 6-Chloro-11-(piperazin-1-yl)-8-trifluoromethyl-5H-dibenzo[b,e][1,4]diazepine (189JO77B) | — | | — | | — | |
| 7-Chloro-11-(piperazin-1-yl)-5H-dibenzo[b,e][1,4]diazepine (160FE35B) | 48 | 6.6 | 53 | 5.4 | — | |
| 8-Bromo-1-chloro-11-(piperazin-1-yl)-5H-dibenzo[b,e][1,4]diazepine (160FE36A) | 66 | 6.9 | 105 | 5.6 | 4 | |
| 8-Bromo-2-methyl-11-(piperazin-1-yl)-5H-dibenzo[b,e][1,4]diazepine (160FE40C) | 8 | | 44 | 5.4 | — | |
| 4,8-Dichloro-11-(piperazin-1-yl)-5H-dibenzo[b,e][1,4]diazepine (160FE41A) | 78 | 7.2 | 118 | 6.0 | 44 | 6.8 |
| 8-Chloro-2-methyl-11-(piperazin-1-yl)-5H-dibenzo[b,e][1,4]diazepine (160FE41B) | 14 | | 28 | 5.9 | — | |
| 8-Chloro-2-fluoro-11-(piperazin-1-yl)-5H-dibenzo[b,e][1,4]diazepine (160FE42A-F3) | 32 | 6.8 | 121 | 5.5 | — | |
| 3,8-Dichloro-11-(piperazin-1-yl)-5H-dibenzo[b,e][1,4]diazepine (160FE42B-F4) | 34 | 6.9 | 58 | 5.8 | — | |
| 2-Bromo-8-chloro-11-(piperazin-1-yl)-5H-dibenzo[b,e][1,4]diazepine (160FE43A-F6) | 6 | | 19 | | — | |
| 3,7-Dichloro-11-(piperazin-1-yl)-5H-dibenzo[b,e][1,4]diazepine (160FE58D1) | 15 | | 19 | | — | |
| 8-Bromo-3-chloro-11-(piperazin-1-yl)-5H-dibenzo[b,e][1,4]diazepine (160FE58D3) | 31 | 6.6 | 34 | 6.5 | — | |
| 3-Chloro-11-(piperazin-1-yl)-5H-dibenzo[b,e][1,4]diazepine (160FE58D6) | 16 | | 27 | 5.7 | — | |
| 3-Chloro-11-(piperazin-1-yl)-8-trifluoromethyl-5H-dibenzo [b,e][1,4]diazepine (160FE58D7) | 11 | | — | | — | |
| 7-Chloro-2-methyl-11-(piperazin-1-yl)-5H-dibenzo[b,e][1,4]diazepine (160FE58E1) | −3 | | 5 | | — | |
| 2-Methyl-11-(piperazin-1-yl)-5H-dibenzo[b,e][1,4]diazepine (160FE58E6) | 1 | | 9 | | — | |
| 2-Methyl-11-(piperazin-1-yl)-8-trifluoromethyl-5H-dibenzo [b,e][1,4]diazepine (160FE58E7) | 15 | | 14 | | — | |
| 8-Chloro-4-methyl-11-(piperazin-1-yl)-5H-dibenzo[b,e][1,4]diazepine (160FE74C) | 92 | 7.2 | 162 | 6.0 | 16 | |
| 1,8-Dichloro-11-(piperazin-1-yl)-5H-dibenzo[b,e][1,4]diazepine (203FE03) | — | | 84 | 5.7 | — | |
| 8-Bromo-5-methyl-11-(piperazin-1-yl)-5H-dibenzo[b,e][1,4]diazepine (166JO32) | 92 | 6.4 | 75 | 5.6 | — | |
| 7,8-Dichloro-11-(piperazin-1-yl)-5H-dibenzo[b,e][1,4]diazepine (166JO28) | 32 | 7.1 | 8 | | — | |
| 11-(Piperazin-1-yl)-8-trifluoromethyl-5H-dibenzo[b,e][1,4]diazepine (166JO23) | 53 | 6.5 | 131 | 5.5 | — | |
| 11-(Piperazin-1-yl)-5H-dibenzo[b,e][1,4]diazepine (160FE19A) | 38 | 6.1 | 70 | 5.6 | — | |
| 8-Fluoro-11-(piperazin-1-yl)-5H-dibenzo[b,e][1,4]diazepine (160FE19C) | 32 | 6.7 | 95 | 5.7 | — | |
| 11-(Piperazin-1-yl)-5H-dibenzo[b,e][1,4]diazepine-8-carbonitrile (160FE19D) | 49 | 6.6 | 106 | 6.0 | — | |
| 8-Bromo-11-(piperazin-1-yl)-5H-dibenzo[b,e][1,4]diazepine (160FE19E) | 63 | 7.2 | 121 | 6.3 | 13 | |
| 8-Methyl-11-(piperazin-1-yl)-5H-dibenzo[b,e][1,4]diazepine (160FE19F) | 49 | 6.8 | 98 | 6.0 | — | |
| 3-Fluoro-6-piperazin-1-yl-11H-dibenzo[b,e]azepine (160FE02) | 23 | | 55 | 6.1 | — | |
| 2-(Trifluoromethanesulfonyloxy)-11-(piperazin-1-yl)-5H-dibenzo[b,e][1,4]diazepine (160FE13A) | −8 | | 9 | | — | |
| 2-(Trifluoromethanesulfonyloxy)-11-(piperazin-1-yl)-5H-dibenzo[b,e][1,4]oxazepine (160FE13B) | −11 | | 4 | | — | |
| 8-Chloro-2-(trifluoromethanesulfonyloxy)-11-(piperazin-1-yl)-5H-dibenzo[b,e][1,4]diazepine (160FE13C) | −2 | | 16 | | — | |
| 8-(Trifluoromethanesulfonyloxy)-11-(piperazin-1-yl)-5H-dibenzo[b,e][1,4]diazepine (160FE13D) | 19 | | 62 | 5.6 | — | |
| 11-(Piperazin-1-yl)-dibenzo[b,f][1,4]thiazepin (160FE17A) | 4 | | 41 | 6.5 | — | |
| 11-(Piperazin-1-yl)-2,3-dihydro-1,4-benzodioxino[6,7-b][1,4]benzothiazepin (160FE17B) | 6 | | 28 | | — | |
| 8-Chloro-11-[1,4]diazepam-1-yl-5H-dibenzo[b,e][1,4]diazepine (160FE16A) | 37 | 7.0 | 82 | 6.2 | — | |
| N'-(8-Chloro-5H-dibenzo[b,e][1,4]diazepine-11-yl)-N,N-dimethyl-ethane-1,2-diamine (160FE16D) | 4 | | 11 | | — | |
| N'-(8-Chloro-5H-dibenzo[b,e][1,4]diazepine-11-yl)-N,N-diethyl-ethane-1,2-diamine (160FE16E) | 6 | | 9 | | — | |

TABLE 1-continued

| Name | M1 | | M2 | | M3 | |
|---|---|---|---|---|---|---|
| | eff | $pEC_{50}$ | eff | $pEC_{50}$ | eff | $pEC_{50}$ |
| 8-Chloro-11-(4-methyl-[1,4]diazepam-1-yl)-5H-dibenzo[b,e][1,4]diazepine (160FE16F) | 18 | | 50 | 5.9 | — | |
| 8-Chloro-2-methoxy-11-(piperazin-1-yl)-5H-dibenzo[b,e][1,4]diazepine (160FE20A) | 7 | | 7 | | — | |
| N'-(5H-dibenzo[b,e][1,4]diazepine-11-yl)-N,N-dimethyl-ethane-1,2-diamine (160FE20B) | 10 | | 20 | | — | |
| 11-[1,4]Diazepam-1-yl-5H-dibenzo[b,e][1,4]diazepine (160FE20C) | 18 | | 25 | | — | |
| N'-(8-Fluoro-5H-dibenzo[b,e][1,4]diazepine-11-yl)-N.N-dimethyl-ethane-1,2-diamine (160FE20D) | 7 | | 21 | | — | |
| 8-Fluoro-11-[1,4]diazepam-1-yl-5H-dibenzo[b,e][1,4]diazepine (160FE16A) | 25 | 6.7 | 67 | 6.6 | — | |
| N'-(8-Chloro-5H-dibenzo[b,e][1,4]diazepine-11-yl)-N-methyl-ethane-1,2-diamine (160FE22) | 5 | | 8 | | — | |
| 8-Chloro-11-(trans-2,5-dimethyl-piperazin-1-yl)-5H-dibenzo[b,e][1,4]diazepine (160FE33A) | 8 | | 24 | | — | |
| 8-Chloro-11-(3,5-dimethyl-piperazin-1-yl)-5H-dibenzo[b,e][1,4]diazepine (160FE33B) | 18 | | 97 | 5.6 | — | |
| 8-Chloro-11-(3-methyl-piperazin-1-yl)-5H-dibenzo[b,e][1,4]diazepine (160FE38) | 28 | 7.0 | 159 | 5.8 | 19 | |
| 8-Chloro-11-(3-phenyl-piperazin-1-yl)-5H-dibenzo[b,e][1,4]diazepine (160FE45) | 5 | | 23 | | — | |
| 8-Chloro-5-methyl-11-(piperazin-1-yl)-5H-dibenzo[b,e][1,4]diazepine (189JO25A) | 65 | 7.1 | 138 | 5.9 | 14 | |
| 8-Chloro-5-benzyl-11-(piperazin-1-yl)-5H-dibenzo[b,e][1,4]diazepine (160FE46-PIPBN) | 41 | 6.3 | 16 | | — | |
| 8-Iodo-11-(piperazin-1-yl)-5H-dibenzo[b,e][1,4]diazepine (166JO38) | 75 | 7.2 | 187 | 6.0 | — | |
| 2-Iodo-8-chloro-11-(piperazin-1-yl)-5H-dibenzo[b,e][1,4]diazepine (166JO54) | 3 | | 10 | | — | |
| 8-Phenyl-11-(piperazin-1-yl)-5H-dibenzo[b,e][1,4]diazepine (189JO53) | — | | 104 | 5.7 | — | |
| 8-Chloro-11-(piperidin-1-yl)-5H-dibenzo[b,e][1,4]diazepine (166JO69A) | 47 | 5.8 | 9 | | — | |
| 8-Chloro-11-(morpholin-4-yl)-5H-dibenzo[b,e][1,4]diazepine (166JO69B) | 11 | | 6 | | — | |
| 5-Allyl-8-chloro-11-(piperazin-1-yl)-5H-dibenzo[b,e][1,4]diazepine (166JO68) | 12 | | 46 | 5.8 | — | |
| 6-Chloro-11-(piperazin-1-yl)-5H-dibenzo[b,e][1,4]diazepine (189JO68) | — | | 71 | 5.4 | — | |
| 8-Chloro-5-piperazin-1-yl-11H-benzo[b]pyrido[2,3-e][1,4]diazepine (166JO63) | 51 | 5.5 | 7 | | — | |
| 2-Chloro-10-piperazin-1-yl-5H-dibenzo[b,f]azepin (189JO39) | 2 | | 3 | | — | |
| 8-Chloro-11-(piperazin-1-yl)-dibenzo[b,f][1,4]thiazepine (189JO16) | 11 | | 52 | 5.9 | — | |
| 8-Chloro-11-(piperazin-1-yl)-dibenzo[b,f][1,4]oxazepine (189JO31) | 52 | 7.0 | 58 | 6.0 | — | |
| 8-Chloro-11-(4-methyl-piperazin-1-yl)-dibenzo[b,f][1,4]oxazepine (189JO47) | 13 | | 46 | 5.8 | — | |
| 3-Chloro-6-piperazin-1-yl-11H-dibenzo[b,e]azepine (189JO60) | — | | 113 | 5.9 | — | |
| 8-Bromo-11-(piperazin-1-yl)-dibenzo[b,f][1,4]oxazepine (189JO48A) | — | | 70 | 5.9 | — | |
| 11-(Piperazin-1-yl)-dibenzo[b,f][1,4]oxazepine (189JO48B) | — | | 58 | 5.7 | | |
| 7-Chloro-11-(piperazin-1-yl)-dibenzo[b,f][1,4]oxazepine (189JO50A) | — | | 53 | 5.9 | — | |
| 8-Chloro-3-methoxy-11-(piperazin-1-yl)-dibenzo[b,f][1,4]oxazepine (189JO50B) | — | | 19 | | — | |
| 8-Bromo-3-methoxy-11-(piperazin-1-yl)-dibenzo[b,f][1,4]oxazepine (189JO50D) | — | | 21 | | — | |
| 3-Methoxy-11-(piperazin-1-yl)-dibenzo[b,f][1,4]oxazepine (189JO50E) | — | | 45 | 5.6 | — | |
| 7-Chloro-3-methoxy-11-(piperazin-1-yl)-dibenzo[b,f][1,4]oxazepine (189JO50F) | — | | 44 | 6.0 | — | |
| 8-Chloro-4-methyl-11-(piperazin-1-yl)-dibenzo[b,f][1,4]oxazepine (189JO50H) | — | | 71 | 6.2 | — | |
| 8-Bromo-4-methyl-11-(piperazin-1-yl)-dibenzo[b,f][1,4]oxazepine (189JO51A) | — | | 48 | 5.8 | — | |
| 4-Methyl-11-(piperazin-1-yl)-dibenzo[b,f][1,4]oxazepine (189JO51B) | — | | 22 | | — | |
| 2-Bromo-8-chloro-11-(piperazin-1-yl)-dibenzo[b,f][1,4]oxazepine (189JO51D) | — | | 13 | | — | |
| 2,8-Dibromo-11-(piperazin-1-yl)-dibenzo[b,f][1,4]oxazepine (189JO51E) | — | | 6 | | — | |
| 2-Bromo-11-(piperazin-1-yl)-dibenzo[b,f][1,4]oxazepine (189JO51F) | — | | 9 | | — | |
| 2-Bromo-7-chloro-11-(piperazin-1-yl)-dibenzo[b,f][1,4]oxazepine (189JO51G) | — | | 15 | | — | |

TABLE 1-continued

| Name | M1 eff | M1 pEC$_{50}$ | M2 eff | M2 pEC$_{50}$ | M3 eff | M3 pEC$_{50}$ |
|---|---|---|---|---|---|---|
| 11-(Piperazin-1-yl)-8-trifluoromethyl-dibenzo[b,f][1,4]oxazepine (189JO54A) | — | | 58 | 5.9 | — | |
| 4-Methyl-11-(piperazin-1-yl)-8-trifluoromethyl-dibenzo[b,f][1,4]oxazepine (189JO54C) | — | | 75 | 6.1 | — | |
| 8-Fluoro-11-(piperazin-1-yl)-dibenzo[b,f][1,4]oxazepine (189JO54E) | — | | 48 | 5.6 | — | |
| 8-Fluoro-3-methoxy-11-(piperazin-1-yl)-dibenzo[b,f][1,4]oxazepine (189JO54F) | — | | 49 | 5.6 | — | |
| 8-Fluoro-4-methyl-11-(piperazin-1-yl)-dibenzo[b,f][1,4]oxazepine (189JO54G) | — | | 50 | 5.8 | — | |
| 2-Bromo-8-fluoro-11-(piperazin-1-yl)-dibenzo[b,f][1,4]oxazepine (189JO54H) | — | | 21 | | — | |
| 8-Methyl-11-(piperazin-1-yl)-dibenzo[b,f][1,4]oxazepine (189JO58A) | — | | 76 | 5.5 | — | |
| 3-Methoxy-8-methyl-11-(piperazin-1-yl)-dibenzo[b,f][1,4]oxazepine (189JO58B) | — | | 45 | 5.5 | — | |
| 4,8-Dimethyl-11-(piperazin-1-yl)-dibenzo[b,f][1,4]oxazepine (189JO58C) | — | | 46 | 6.1 | — | |
| 3-Methoxy-11-(piperazin-1-yl)-8-trifluoromethyl-dibenzo[b,f][1,4]oxazepine (189JO62A) | — | | 17 | | — | |
| 2-Bromo-11-(piperazin-1-yl)-8-trifluoromethyl-dibenzo[b,f][1,4]oxazepine (189JO62B) | — | | 11 | | — | |
| 6-Chloro-11-(piperazin-1-yl)-dibenzo[b,f][1,4]oxazepine (189JO69) | — | | — | | — | |
| 2-Bromo-8-methyl-11-(piperazin-1-yl)-dibenzo[b,f][1,4]oxazepine (189JO63A) | — | | 17 | | — | |
| 7-Chloro-4-methyl-11-(piperazin-1-yl)-dibenzo[b,f][1,4]oxazepine (189JO63B) | — | | 28 | 6.4 | — | |
| 8-Phenyl-11-(piperazin-1-yl)-dibenzo[b,f][1,4]oxazepine (189JO64) | — | | 33 | 5.9 | — | |
| 8-Chloro-11-(piperidin-4-yl)-5H-dibenzo[b,e][1,4]diazepine (160FE67A) | 57 | 6.2 | 31 | 5.7 | — | |
| 5-Benzyl-8-chloro-11-(piperidin-4-yl)-5H-dibenzo[b,e][1,4]diazepine (160FE67B) | 12 | | 5 | | — | |
| (8-Chloro-5H-dibenzo[b,e][1,4]diazepin-11-yl)-(S)-1-pyrrolidin-2-yl-methyl-amine (166JO51) | 77 | 6.3 | 23 | | — | |
| 1-(8-Chloro-5H-dibenzo[b,e][1,4]diazepin-11-yl)-piperidine-4-yl-amine (166JO55) | 6 | | 95 | 5.6 | — | |
| 1-(8-Chloro-5H-dibenzo[b,e][1,4]diazepin-11-yl)-pyrrolidin-3-yl-amine (166JO64) | 8 | | 36 | 5.5 | — | |
| (8-Chloro-5H-dibenzo[b,e][1,4]diazepin-11-yl)-(R)-1-pyrrolidin-2-yl-methyl-amine (166JO70) | 4 | | 5 | | — | |
| (8-Chloro-5H-dibenzo[b,e][1,4]diazepin-11-yl)-pyrrolidin-3-yl-amine (166JO74) | 10 | | 18 | | — | |
| 8-Chloro-11-(2,5-diaza-bicyclo[2.2.1]hept-2-yl)-5H-dibenzo[b,e][1,4]diazepine (166JO39-2) | 34 | 6.6 | 49 | 5.6 | — | |
| Acetidin-3-yl-(8-chloro-5H-dibenzo[b,e][1,4]diazepine-11-yl)amine (189JO65) | — | | 17 | | — | |
| 7-Bromo-4-(piperazin-1-yl)-2,3-dihydro-1H-benzo[b][1,4]diazepine (166JO47) | 56 | 5.6 | 3 | | — | |
| 7-Bromo-2-methyl-(piperazin-1-yl)-2,3 dihydro-1H-benzo[b][1,4]diazepine (166JO95) | 16 | | 23 | | — | |
| 7-Bromo-2-phenyl-4-(piperazine-1-yl)-2,3-dihydro-1H-benzo[b][1,4]diazepine (189JO20) | 3 | | 19 | | — | |
| 7-Bromo-10-(piperazin-1-yl)-1,2,3,3a,4,10a-hexahydro-benzo[b]cyclopenta[e][1,4]diazepine (166JO46) | 50 | 5.8 | 12 | | — | |
| 8-Chloro-11-(4-fluorobenzyl)-5H-dibenzo[b,e][1,4]diazepine (160FE59) | 3 | | 7 | | — | |
| 8-Chloro-11-(4-fluorophenyl)-5H-dibenzo[b,e][1,4]diazepine (160FE70) | 13 | | 4 | | — | |
| 8-Chloro-11-(4-nonylphenyl)-5H-dibenzo[b,e][1,4]diazepine (160FE63) | 1 | | 8 | | — | |
| 8-Chloro-11-(pyridin-4-yl)-5H-dibenzo[b,e][1,4]diazepine (160FE69A) | 6 | | 6 | | — | |
| 8-Chloro-11-(1H-pyrazol-4-yl)-5H-dibenzo[b,e][1,4]diazepine (160FE59) | 9 | | 3 | | — | |

What is claimed is:

1. A method of treating cognitive impairment associated with Alzheimer's disease, schizophrenia or related idiopathic psychoses, Huntington's disease, Tourette's syndrome, anxiety, affective disorders, drug-induced psychoses, psychoses secondary to neurodegenerative disorders, major depression, bipolar disorder, depression with psychotic features, or sleep disorders, comprising administering to a subject exhibiting one or more symptoms of cognitive impairment a therapeutically effective amount of a compound of Formula I:

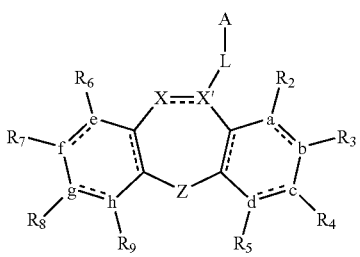

(I)

or a pharmaceutically acceptable salt thereof, wherein:
A has the structure:

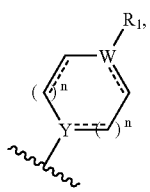

wherein each bond represented by a dashed and solid line in A represents a carbon-carbon single bond;
X is nitrogen;
X' is C;
Y is nitrogen;
W is nitrogen;
each n is 1;
$R_1$ is hydrogen;
L is absent;
a, b, c, and d are each carbon,
e, f, g, and h are each carbon,
$R_2$, $R_3$, $R_4$, and $R_5$, are each separately selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, $NO_2$, $NHCOR_{10}$,
or $R_2$ and $R_3$, or $R_3$ and $R_4$, or $R_4$ and $R_5$ taken together, along with the ring carbons to which they are attached, form a five-membered or six-membered cycloalkyl, heterocyclyl or heteroaryl ring, or a six-membered aryl ring moiety;
$R_6$, $R_7$, $R_8$, and $R_9$, are each separately selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, $NO_2$, $NHCOR_{10}$,
or $R_6$ and $R_7$, or $R_7$ and $R_8$, or $R_8$ and $R_9$ taken together, along with the ring carbons to which they are attached, form a five-membered or six-membered cycloalkyl, heterocyclyl or heteroaryl ring, or a six-membered aryl ring moiety;
Z is oxygen;
$R_{10}$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl optionally substituted aryl, optionally substituted arylalkyl, and perhaloalkyl; and
each bond represented by a dashed and solid line in Formula I represents a carbon-carbon double bond.

2. The method of claim 1, wherein each $R_2$ is independently selected from the group consisting of hydrogen, halogen, optionally substituted $C_{1-6}$ alkyl, and optionally substituted $C_{1-6}$ alkyloxy.

3. The method of claim 1, wherein $R_2$ is selected from the group consisting of hydrogen, methyl, methoxy, and chloro.

4. The method of claim 1, wherein $R_3$ is selected from the group consisting of hydrogen, halogen, optionally substituted $C_{1-6}$ alkyl, optionally substituted $C_{1-6}$ alkyloxy, and $NO_2$.

5. The method of claim 1, wherein $R_3$ is selected from the group consisting of hydrogen, methyl, methoxy, chloro, bromo, iodo, and $NO_2$.

6. The method of claim 1, wherein $R_4$ is selected from the group consisting of hydrogen, halogen, optionally substituted $C_{1-6}$ alkyl, perhaloalkyl, $SO_2R_{10}$, and $NO_2$.

7. The method of claim 1, wherein $R_4$ is selected from the group consisting of hydrogen, methyl, fluoro, chloro, bromo, trifluoromethyl, $SO_2CH_3$, and $NO_2$.

8. The method of claim 1, wherein $R_5$ is selected from the group consisting of hydrogen, halogen, and optionally substituted $C_{1-6}$ alkyl.

9. The method of claim 1, wherein $R_5$ is hydrogen or chloro.

10. The method of claim 1, wherein $R_6$ is hydrogen or optionally substituted $C_{1-6}$ alkyl.

11. The method of claim 1, wherein $R_7$ is selected from the group consisting of hydrogen, halogen, optionally substituted $C_{1-6}$ alkyl, perhaloalkyl, CN, $SO_2R_{10}$, and $NO_2$.

12. The method of claim 1, wherein $R_7$ is selected from the group consisting of hydrogen, methyl, chloro, fluoro, trifluoromethyl, $SO_2CH_3$, CN, and $NO_2$.

13. The method of claim 1, wherein $R_8$ is selected from the group consisting of hydrogen, halogen, optionally substituted $C_{1-6}$ alkyl.

14. The method of claim 1, wherein $R_8$ is selected from the group consisting of hydrogen, chloro, and bromo.

15. The method of claim 1, wherein $R_9$ is selected from the group consisting of hydrogen, halogen, optionally substituted $C_{1-6}$ alkyl, and perhaloalkyl.

16. The method of claim 1, wherein $R_9$ is selected from the group consisting of hydrogen, chloro, methyl, and trifluoromethyl.

17. The method of claim 1, wherein:
$R_1$ is hydrogen;
$R_2$, $R_3$, and $R_4$, are each hydrogen;
$R_6$, $R_8$, and $R_9$, are each hydrogen;
$R_5$ is selected from the group consisting of halogen, optionally substituted $C_{1-6}$ alkyl, optionally substituted $C_{2-6}$ alkenyl, optionally substituted $C_{2-6}$ alkynyl, perhaloalkyl, and CN; and
$R_7$ is selected from the group consisting of halogen, optionally substituted $C_{1-6}$ alkyl, optionally substituted $C_{2-6}$ alkenyl, optionally substituted $C_{2-6}$ alkynyl, perhaloalkyl, and CN.

18. The method of claim 17, wherein $R_5$ is selected from the group consisting of halogen and optionally substituted $C_{1-6}$ alkyl.

19. The method of claim 18, wherein $R_5$ is chloro.

20. The method of claim 17, wherein $R_7$ is selected from the group consisting of halogen, optionally substituted $C_{1-6}$ alkyl, perhaloalkyl, and CN.

21. The method of claim 17, wherein the compound is selected from the group consisting of:
 8-Chloro-4-methyl-11-(piperazin-1-yl)-dibenzo[b,f][1,4]oxazepine,
 8-Bromo-4-methyl-11-(piperazin-1-yl)-dibenzo[b,f][1,4]oxazepine,
 4-Methyl-11-(piperazin-1-yl)-8-trifluoromethyl-dibenzo[b,f][1,4]oxazepine,
 8-Fluoro-4-methyl-11-(piperazin-1-yl)-dibenzo[b,f][1,4]oxazepine, and
 4,8-Dimethyl-11-(piperazin-1-yl)-dibenzo[b,f][1,4]oxazepine.

22. The method of claim 1, wherein the compound is selected from the group consisting of:
 2-(Trifluoromethanesulfonyloxy)-11-(piperazin-1-yl)-5H-dibenzo[b,e][1,4]oxazepine,
 8-Chloro-11-(piperazin-1-yl)-dibenzo[b,f][1,4]oxazepine,
 11-(piperazin-1-yl)-dibenzo[b,f][1,4]oxazepine,
 7-Chloro-11-(piperazin-1-yl)-dibenzo[b,f][1,4]oxazepine,
 8-Chloro-3-methoxy-11-(piperazin-1-yl)-dibenzo[b,f][1,4]oxazepine,
 8-Bromo-3-methoxy-11-piperazin-1-yl)-dibenzo[b,f][1,4]oxazepine,
 3-Methoxy-11-(piperazin-1-yl)-dibenzo[b,f][1,4]oxazepine,
 7-Chloro-3-methoxy-11-(piperazin-1-yl)-dibenzo[b,f][1,4]oxazepine,
 4-Methyl-11-(piperazin-1-yl)-dibenzo[b,f][1,4]oxazepine,
 2-Bromo-8-chloro-11-(piperazin-1-yl)-dibenzo[b,f][1,4]oxazepine,
 2,8-Dibromo-11-(piperazin-1-yl)-dibenzo[b,f][1,4]oxazepine,
 2-Bromo-11-(piperazin-1-yl)-dibenzo[b,f][1,4]oxazepine,
 2-Bromo-7-chloro-11-(piperazin-1-yl)-dibenzo[b,f][1,4]oxazepine,
 11-(piperazin-1-yl)-8-trifluoromethyl-dibenzo[b,f][1,4]oxazepine,
 8-Fluoro-3-methoxy-11-(piperazin-1-yl)-dibenzo[b,f][1,4]oxazepine,
 2-Bromo-8-fluoro-11-(piperazin-1-yl)-dibenzo[b,f][1,4]oxazepine,
 8-Methyl-11-(piperazin-1-yl)-dibenzo[b,f][1,4]oxazepine,
 3-Methoxy-8-methyl-11-(piperazin-1-yl)-dibenzo[b,f][1,4]oxazepine,
 3-Methoxy-11-(piperazin-1-yl)-8-trifluoromethyl-dibenzo[b,f][1,4]oxazepine,
 2-Bromo-11-(piperazin-1-yl)-8-trifluoromethyl-dibenzo[b,f][1,4]oxazepine,
 6-Chloro-11-(piperazin-1-yl)-dibenzo[b,f][1,4]oxazepine,
 2-Bromo-8-methyl-11-(piperazin-1-yl)-dibenzo[b,f][1,4]oxazepine,
 7-Chloro-4-methyl-11-(piperazin-1-yl)-dibenzo[b,f][1,4]oxazepine, and
 8-Phenyl-11-(piperazin-1-yl)-dibenzo[b,f][1,4]oxazepine.

23. The method of claim 1, wherein the compound is selected from the group consisting of:
 8-Chloro-4-methyl-11-(piperazin-1-yl)-dibenzo[b,f][1,4]oxazepine,
 8-Fluoro-4-methyl-11-(piperazin-1-yl)-dibenzo[b,f][1,4]oxazepine,
 4-Methyl-11-(piperazin-1-yl)-8-trifluoromethyl-dibenzo[b,f][1,4]oxazepine,
 8-Bromo-11-(piperazin-1-yl)-dibenzo[b,f][1,4]oxazepine, and
 8-Fluoro-11-(piperazin-1-yl)-dibenzo[b,f][1,4]oxazepine.

24. The method of claim 1, wherein the compound is selected from the group consisting of:
 8-Fluoro-4-methyl-11-(piperazin-1-yl)-dibenzo[b,f][1,4]oxazepine, and
 8-Chloro-4-methyl-11-(piperazin-1-yl)-dibenzo[b,f][1,4]oxazepine.

25. The method of claim 1, wherein:
 $R_2$, $R_3$, and $R_4$, are each hydrogen;
 $R_6$, $R_7$, and $R_9$, are each hydrogen;
 $R_5$ is selected from the group consisting of halogen, optionally substituted $C_{1-6}$ alkyl, optionally substituted $C_{2-6}$ alkenyl, optionally substituted $C_{2-6}$ alkynyl, perhaloalkyl, and CN; and
 $R_8$ is selected from the group consisting of halogen, optionally substituted $C_{1-6}$ alkyl, optionally substituted $C_{2-6}$ alkenyl, optionally substituted $C_{2-6}$ alkynyl, perhaloalkyl, and CN.

26. The method of claim 1, wherein $R_5$ is selected from the group consisting of halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, $NHCONHR_{10}$, $SO_2NHR_{10}$, $SO_2R_{10}$, $OSO_2R_{10}$, $NO_2$, and $NHCOR_{10}$.

* * * * *

UNITED STATES PATENT AND TRADEMARK OFFICE
CERTIFICATE OF CORRECTION

| | |
|---|---|
| PATENT NO. | : 7,622,461 B2 |
| APPLICATION NO. | : 11/733476 |
| DATED | : November 24, 2009 |
| INVENTOR(S) | : Fredrik Ek et al. |

It is certified that error appears in the above-identified patent and that said Letters Patent is hereby corrected as shown below:

Title Page, at item 75, page 1, inventors, line 2, please delete "Bunkeflostrand, (SE)" and insert --Bunkeflo Strand, (SE)--.

Title Page, at item 75, inventors, line 3, please delete "Sanby, (SE)" and insert --Lund, (SE)--.

Title Page, at item 63, Related U.S. Application Data, line 2, please delete "2004" and insert --2004, now U.S. Pat. 7,550,454.--.

Title Page, at item 57, Abstract, line 3, please delete "thereof" and insert --thereof:--.

Title Page, at item 56, page 3, column 1, line 6, please delete "Pharrnacol" and insert --Pharmacol--.

Title Page, at item 56, page 3, column 1, line 20, please delete "Psychopharrnacol." and insert --Psychopharmacol.--.

Title Page, at item 56, page 5, column 1, line 71, please delete "substrituents" and insert --substituents--.

At column 1, line 10, please delete "2004: and insert --now Pat. No. 7,550,454,--.

At column 1, line 56, please delete "ACHE" and insert --AChE--.

At column 1, line 62, please delete "ACHE" and insert --AchE--.

At column 1, line 65, please delete "ACHE" and insert --AchE--.

Signed and Sealed this
Twenty-seventh Day of December, 2011

David J. Kappos
*Director of the United States Patent and Trademark Office*

At column 2, line 18-28 (Approx.),
Please delete " 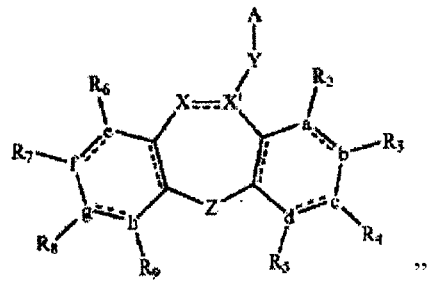 "
and insert -- 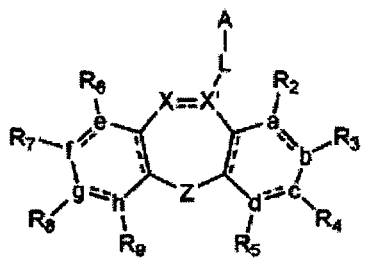 --.
At column 2, line 45-52 (Approx.),
Please delete " 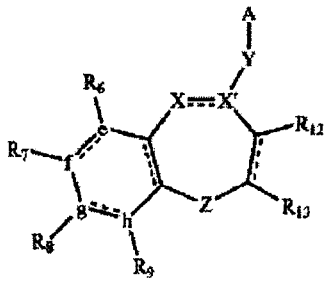 "
and insert -- 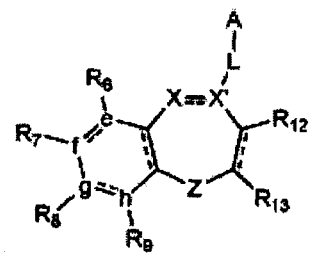 --.
At column 12, line 14, please delete "thereof," and insert --thereof;--.

CERTIFICATE OF CORRECTION (continued)
U.S. Pat. No. 7,622,461 B2

At column 14, line 2-12, Change " 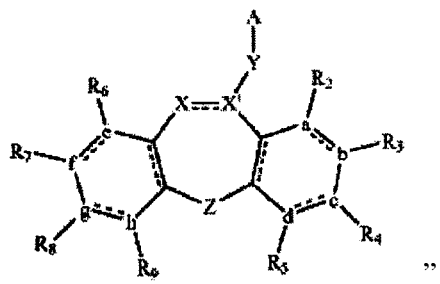 "

and insert -- 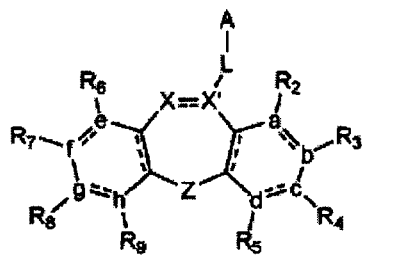 --.

At column 14, line 26-36,

Change " 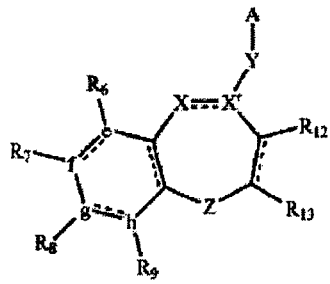 "

and insert -- 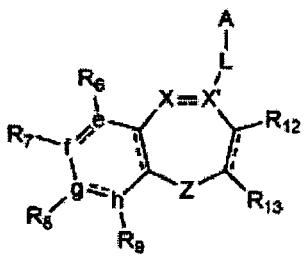 --.

At column 18, line 59, please delete "C-arnido" and insert -- "C-amido"--.

At column 19, line 51, please delete "1,4-oxathiane," and insert --1,4-oxathiin,--. (First occurrence)

At column 19, line 56, please delete "pyrrolidone," and insert --pyrrolidione,--. (Second Occurrence)

At column 37, line 57, please delete "thereof," and insert --thereof;--.

At column 84, line 67, please delete "system)" and insert --.--.

CERTIFICATE OF CORRECTION (continued)
U.S. Pat. No. 7,622,461 B2

At column 86, line 56, please delete "benzylchloride" and insert --benzoylchloride--.

At column 86, line 67, please delete "12.6" and insert --.--.

At column 90, line 67, please delete "(MH$^+$)" and insert --.--.

At column 106, line 1, please delete "alkynyl" and insert --,--.

At column 107, line 24, please delete "11-piperazin-1-yl)" and insert --11-(piperazin-1-y-)--.